US011230520B2

United States Patent
Grubbs et al.

(10) Patent No.: US 11,230,520 B2
(45) Date of Patent: *Jan. 25, 2022

(54) SILYLATIONS OF AROMATIC SUBSTRATES WITH BASE-ACTIVATED ORGANOSILANES

(71) Applicant: CALIFORNIA INSTITUTE OF TECHNOLOGY, Pasadena, CA (US)

(72) Inventors: Robert H. Grubbs, South Pasadena, CA (US); Alexey Fedorov, Wallisellen (CH); Anton Toutov, Pasadena, CA (US); Kerry N. Betz, Boulder, CO (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/142,751

(22) Filed: Jan. 6, 2021

(65) Prior Publication Data

US 2021/0122701 A1 Apr. 29, 2021

Related U.S. Application Data

(63) Continuation of application No. 15/889,295, filed on Feb. 6, 2018, now Pat. No. 10,927,065, which is a continuation of application No. 14/043,917, filed on Oct. 2, 2013, now Pat. No. 9,908,840.

(60) Provisional application No. 61/708,931, filed on Oct. 2, 2012, provisional application No. 61/818,573, filed on May 2, 2013, provisional application No. 61/865,870, filed on Aug. 14, 2013.

(51) Int. Cl.
| | |
|---|---|
| *C07C 209/28* | (2006.01) |
| *C07C 209/62* | (2006.01) |
| *C07C 37/50* | (2006.01) |
| *C07C 37/055* | (2006.01) |
| *C07C 1/22* | (2006.01) |
| *C07C 319/06* | (2006.01) |
| *C07F 7/08* | (2006.01) |

(52) U.S. Cl.
CPC .............. *C07C 209/28* (2013.01); *C07C 1/22* (2013.01); *C07C 37/055* (2013.01); *C07C 37/50* (2013.01); *C07C 209/62* (2013.01); *C07C 319/06* (2013.01); *C07F 7/081* (2013.01); *C07F 7/0814* (2013.01); *C07B 2200/05* (2013.01)

(58) Field of Classification Search
CPC ..... C07C 209/28; C07C 209/62; C07C 37/50; C07C 37/055; C07C 1/22; C07C 319/06; C07F 7/081; C07F 7/0814; C07B 2200/05
See application file for complete search history.

(56) References Cited

U.S. PATENT DOCUMENTS

| | | | |
|---|---|---|---|
| 4,360,686 A | 11/1982 | Wang et al. | |
| 4,363,925 A | 12/1982 | Acker et al. | |
| 5,516,908 A | 5/1996 | Freyne et al. | |
| 9,000,167 B2 | 4/2015 | Grubbs et al. | |
| 9,309,269 B2 | 4/2016 | Grubbs et al. | |
| 9,764,995 B2 | 9/2017 | Toutov et al. | |
| 9,809,607 B2 | 11/2017 | Toutov et al. | |
| 9,908,840 B2 | 3/2018 | Grubbs et al. | |
| 2004/0192912 A1 | 9/2004 | Pendri et al. | |
| 2011/0144321 A1 | 6/2011 | Chand et al. | |
| 2015/0166579 A1 | 6/2015 | Grubbs et al. | |
| 2016/0176772 A1 | 6/2016 | Toutov et al. | |

FOREIGN PATENT DOCUMENTS

| | | |
|---|---|---|
| CN | 1072681 A | 6/1993 |
| RU | 2200562 | 3/2003 |
| RU | 2398237 | 8/2010 |
| WO | 2014/055587 A1 | 4/2014 |

OTHER PUBLICATIONS

Aikawa, et al., "Highly Enantioselective Alkynylation of Trifluoropyruvate with Alkynylsilanes Catalyzed by the BINAP—Pd Complex: Access to a-Trifluoromethyl-Substituted Tertiary Alcohols", Org. Lett., Nov. 16, 2010, 12(24), 5716-5719.
Anastas, et al., "Origins, Current Status, and Future Challenges of Green Chemistry", Chem. Res. 2002, vol. 35(9), 686-694.
Andreev, et al., "Direct Electrophilic Silyiation of Terminal Alkynes", Organic Letters, Jan. 15, 2004, vol. 6(3), 421-424.
Babudri, et al., "A Straightforward Route to Polyenylsilanes by Palladium-Catalyzed or Nickel-Catalyzed Cross-Coupling Reactions", Tetrahedron, 1998, 54(7),1085-1094.
Ball et al.. Science, "Gold-Catalyed Direct Arylation", Sep. 28, 2012, vol. 337(102), 1644-1648.
Bekele et al., "Improved Synthesis of the Boe and Fmoc Derivatives of 4-(2'-Aminoethyl)-6-dibenzofuranpropionic Acid: An Unnatural Amino Acid That Nucleates (Beta)-Sheet Folding", Journal of Organic Chemistry, 1997, 62, 2259-2262.
Bergman, et al., Organometallic chemistry: C—H activation, Nature, Mar. 2007, vol. 446, 391-393.
Bideau et al., Chem. Commun., 2001, 1408-1409.

(Continued)

*Primary Examiner* — Timothy R Rozof
(74) *Attorney, Agent, or Firm* — BakerHostetler

(57) ABSTRACT

The present disclosure describes methods for silylating aromatic organic substrates, and associated chemical systems, said methods comprising or consisting essentially of contacting the aromatic organic substrate with a mixture of (a) at least one organosilane and (b) at least one strong base, under conditions sufficient to silylate the aromatic substrate.

40 Claims, 20 Drawing Sheets

(56) References Cited

OTHER PUBLICATIONS

Cheng, et al., "Rhodium-Catalyzed Intermolecular C—H Silyiation of Arenes with High Steric Regiocontrol", Science, Feb. 2014, 343(6173), 853-857.
Cheng, et al., "Synthesis of Conjugated Polymers for Organic Solar Cell Applications", Chem. Rev., Sep. 2009, vol. 109(11), 5868-5923.
Cheve et al., "De Novo Design, Synthesis and Pharmacological Evaluation of New Azaindole Derivatives as Dual Inhibitors af Abl and Src kinases", Med Chem Comm, 2012, 3, 7, 788-800.
Chinchilla, et al., "Recent Advances in Sonogashira Reactions", Chern. Soc. Rev., Mar. 18, 2011,40, 5084-5121.
Clark, et al., "Green Chemistry: Challenges and Opportunities", Green Chern., Feb. 1999, vol. 1, 1-8.
Collins, et al., "A Robustness Screen for the Rapid Assessment of Chemical Reaction", Nature Chem., Jun. 2013, 5, 597-601.
Curless, et al., "E—H (E=R3Si or H) Bond Activation by B(C6F5)3 and Heteroarenes; Competitive Debydrosilylation, Bydrosilyiation and Hydrogenation", Chern. Commun., Nov. 2013, 50, 5270-5272.
Denmark, et al., Palladium-Catalyzed Cross-Coupling Reactions of Silanolates: a Paradigm Shift in Silicon-Based Cross-Coupling Reactions. Chem. Eur., 2006, 2, 4954-4963.
Dervan et al., "Trimethylsilylpotassium. Deoxygenation of epoxides with inversion of stereochemistry", Journal of the American Chemical Society, Mar. 1976, vol. 98, 1265-1267.
Despotopoulou, et al., "Synthesis of Fully Substituted Pyrazoles via Regio- and Chemoselective Metalations", P. Org. Lett., Jul. 2009, 11(15), 3326-29.
Diez-Gonzalez et al., "Copper, Silver and Gold Complexes in Hydrosilyation Reactions", Accts. Chem Res., 2008, 41(2), 349-358.
Du, et al., "Semisynthesis of DB-6 7 and Other Silatecans from Camptotbecin by Thiol-Promoted Addition of Silyl Radicals", Bioorg. Med. Chem., Feb. 2003, 11(3), 451-458.
Dudziec, et al., "New Catalytic Route to Monoalkynyl-Functionalized Di and Trivinyl-Substituted Cyclosiloxanes and Divinylcyclosilazanes", Organometallics, Oct. 2008, vol. 27(21), 5598-5604.
Eabom, Cleavages of Aryl-Silicon and Related Bonds by Electrophiles, J. Organomet. Chem., Oct. 1975, vol. 100(1), 43-57.
Fedorov, et al., "Lewis-Base Silane Activation: From Reductive Cleavage of Aryl Ethers to Selective Ortho-Silylation", Chem. Sci., Feb. 2013, 4, 1640-1645.
Franz, et al., "Organosilicon Molecules with Medicinal Applications", J Med. Chem.,Oct. 2012, 56(2), 388-405.
Frick, et al., "Elektrophile Silylierung Elektronenreicher Heteroaromaten", Synthesis, Nov. 1984, 929-930.
Fujiki, "Optically Active Polysilanes. Ten Years of Progress and New Polymer Twist for Nanoscience and Nanotechnology", Polymer Journal, 2003, vol. 35(4), 297-344.
Furukawa, et al., "Development of a Sila-Friedel-Crafls Reaction and its Application to the Synthesis of Dibenzosilole Derivatives", J. Am. Chem. Soc., Sep. 2009, 131(40), 14192-14193.
Gleiter, et al., "Alkynes Between Main Group Element: From Dumbbells via Rods to Squares and Tubes", Chem. Rev., Apr. 14, 2010, 110, 4447-88.
Godula, et al., "C—H Bond Functionalization in Complex Organic Synthesis", Science, 2006, vol. 312, 67-72.
Haebich, etaL, "Preparation of Aryl-And Heteroaryltrimethylsilanes", Synthesis, 1979, Issue 11, 841-876.
Hameet, et al., "(NHC)Cul (NHC = N-Heterocyclic Carbene) Complexes as Efficient Catalysts for the Reduction of Carbonyl Compounds", Organometallics, 2004, 23(5), 1157-1160.
Hansen, et al., "Lithiated Benzothiophenes and Benzofurans Require 2-Silyl Protection to Avoid Anion Migration", Revue, 2004, 8, 1351-1354.
Huestis, et al., "Site-Selective Azaindole Arylation at the Azine and Azole Rings via N-Oxide Activation", Org Lett., Mar. 2009, 11(6), 1357-60.

Ishikawa, et al., "Dehydrogenative Coupling Between Hydrosilanes and Alkynes Catalyzed by Alkoxided, Alkylmetals, and Metalamides", Journ. Of Catalysis, Apr. 16, 1999, 185, 454-61.
Islam, et al., "On water", Phosphine-Free Palladium-Catalyzed Room Temperature C—H Arylation of Indoles., Chem. Eur. J., 2013, 19, 15093-15096.
Isogai, et al., "CUX2-Mediated [4+2] Benzannulation as a New Synthetic Tool for Stereoselective Construction of Haloaromatic Compounds", Tetrahedron, 65, Sep. 2009, 9575-82.
Itami, et al., "2-Pyridylsilyl Group: A Useful Multifunctional Group in Organic Synthesis", Synlett, Dec. 2005, 2, 157-180.
Itoh, "Disproportionation Reactions of Organohydrosilanes in the Presence of Base Catalysts", Journ. Of Organo Metalic Chem., 629, Feb. 2001, 1-6.
Itoh, et al., "Dehydrogenative Coupling Reactions Between Hydrosilanes and Monosubstituted Alkynes Catalyzed by Solid Bases", Journ. Of Organo Chem., 476,1994, C30-C31.
Kakiuchi, et al., "Ru3 (CO) 12-Catalyzed Silylation of Benzylic C—H Bonds in Arylpyridines and Arylpyrazoles with Hydrosilanes via C—H Bond Cleavage", J A.m. Chem. Soc., Sep. 2004, 126(40), 12792-12793.
Kanyiva et al., "Palladium-catalyzed direct C—H silylation and germanylation of benzamides and carboxamides", Organic Letters, Mar. 2014, vol. 16, 1968-1971.
Kaur et al., "(NHC)Cu1 (NHC = N-Heterocyclic Carbene) Complexes as Efficient Catalysts for the Reduction of Carbonyl Compounds", Organometallics, 2004, 23, 1157-1160.
Keaton, et al., "Titanium(II)-Mediated Cyclization of (Silyloxy)enynes: A Total Synthesis of (−)-7-Demethylpiericidin A1", JACS, Dec. 17, 2005, 408-409.
Kim, et al., "Regio- and Stereoselective Enyne Cross Metathesis of Silylated Internal Alkynes", JACS, Aug. 3, 2004, 10242-43.
Klare, et al., "Cooperative Catalyic Activation of Si—H bonds by a Polar Ru—S Bond: Regioselective Low-Temperature C—H Silyiation of Indoles Under Neutral Conditions by a Friedel-Crafts Mechanism", J. Ant Chem. Soc., Feb. 2011, 133(10), 3312-3315.
Kong, et al., "Highly Efficient Construction of Benzene Ring in Carbazoles by Palladium-Catalyzed Endo-Mode Oxidative Cyclization of 3-(3'-alkenyl)indoles", Org. Lett., 2006, 8, 1339-1342.
Konigs et al., "Base-Free Dehydrogenative Coupling of Enolizable Carbonyl Compounds With Silanes", Org. Lett., 2012, 14(11), 2842-2845.
Kuznetsov et al., "General and Practical One-Pot Synthesis of Dihydrobenzosiloles ram Styrenes", Org. Lett., 2012, 14(3), 914-917.
Kuznetsov, et al., "Fused Heteroaromatic Dihydrosiloles: Synthesis and Double-Fold Modification", Org. Lett., Apr. 2013, 15(10), 2498-2501.
Kyalo, et al., "Palladium-catalyzed Direct C—H Silyiation And Germanylation Of Benzamides And Carboxamides", Org. Lett, 2014, vol. 16, 1968-1971.
Langkopf, et al., "Uses of Silicon-Containing Compounds in the Synthesis of Natural Products", Chem. Rev., Jul. 1995, 95(5), 1375-1408.
Lee, et al., "Highly Selective and Practical Hydrolytic Oxidation of Organosilanes to Silanols Catalyzed by a Ruthenium Complex", J Am Chem. Soc., 2000, 122(48), 12011-12012.
Li, et al., "Green Chemistry for chemical Synthesis", Proc. Natl Acad. Sci., 2008,105,13197-13202.
Li, et al., "Green chemistry: The Development of Cross-Dehydrogenative Coupling (CDC) for Chemical Synthesis", Pure Appl., 2006, Chem. 78(5), 935-945.
Lu, et al., "Efficient Iridium-Catalyzed C—H Functionalization/ Silylation of Heteroarenes", Angew. Chem., Int. Ed., Aug. 2008, 47(39), 7508-7510.
Mahadevan, et al., "Ambident Heterocyclic Reactivity: The Alkylation of Pyrrolopyridines (azaindoles, diazaindenes)", Aug. 1993, 49(33), 7337-52.
Marsden, et al. Structure-Property Relationships of Donor Acceptor-Functionalized Tetrakis(phenylethynyl)benzenes and Bis(dehydrobenzoannuleno)benzenes, J Am. Chem. Soc , Feb. 2005, 2464-76.

(56) References Cited

OTHER PUBLICATIONS

Mita, et al., "Sequential Protocol for C(sp3_-H Carboxylation with CO2: Transition—Metal-Catalyzed Benzylic C—H Silylation and Fluoride-Medicated Carboxylation", Organic Letters, Jun. 19, 2012, vol. 14(13), 3462-3465.
Miyaura, "Organoboron Compounds", Top. Curr. Chem., Jan. 2002, 219, 11-59.
Miyaura, et al., "Palladium-Catalyzed Cross-Coupling Reactions of Organoboron Compounds", A. Chem. Rev. 1995, 95(7), 2457-2483.
Mu, et al. "Silicon-Based Building Blocks for One-Step 18F-Radiolabeling of Peptides for PET Imagin", Angew Chem., 2008, 47, 4922-25.
Nishihara, et al., "Palladium/Copper-Catalyzed Sila-Sonogashira Reactions of Aryl Iodides with Alkynylsilanes via a Direct C—Si Bond Activation", Tetrahedron Letters, 50, Jun. 2009, 4643-4646.
Oyamada, et al., "Scandium-Catalyzed Silylation of Aromatic C—H bonds", Angew. Chem. Int. Ed., Sep. 2011, 50, 10720-10723.
Park et al., "Transition Metal-Catalyzed Ortho-Functionalization in Organic Synthesis", Bull. Korean Chem. Soc., 2005, vol. 26, No. 6, 871-877.
Park, et al., "Gold-Catalyzed Intramolecular Allylation of Silyl Alkynes Induced by Silane Alcoholysis" JACS, 128, 10664-10665, Jul. 28, 2006, 10664-65.
Rahaim, et al., "Zinc-Catalyzed Silylation of Terminal Alkynes", J. Org. Chem., Mar. 11, 2008, vol. 73, 2912-2915.
Rychnovsky et al., "Synthesis of Optically Pure Arylsilylcarbinols and Their Use as Chiral Auxiliaries in Oxacarbenium Ion Reactions", Journal of Organic Chemistry, 2003, 68, 10135-10145.
Sakakura, et al., "Catalytic C—H Activation. Silylation of Arenes with Hydrosilane or Disilane by RhCl (CO)(PMe)2 Under Irradiation", Chem. Lett., 1987, 16(12), 2375-2378.
Scheuermann, "Beyond Traditional Cross Couplings: The Scope of the Cross Dehydrogenative Coupling Reaction", Chem. Asian J., Dec. 2009, vol. 5, 436-451.
Seiple, et al., "Direct C—H Arylation of Electron-Deficient Heterocycles with Arylboronic Acids", J. Am. Chem. Soc., Sep. 2010, 132(38), 13194-13196.
Seregin, et al., "Direct Transition Metal-Catalyzed Functionalization of Heteroaromatic Compounds", Chem. Soc. Rev., Mar. 2007, 36, 1173-1193.
Shimizu, et al., "Dehydrogenative Silylation of Terminal Alkynes by Iridium Catalyst", Tet. Lett., 2000, vol. 41, 907-910.
Shippey et al., "Trimethylsilyl anions. Direct synthesis of trimethylsilybenzenes", Journal of Organic Chemistry, 1977, vol. 42, 2654-2655.
Showell, et al., "Chemistry Challenges in Lead Optimization: Silicon Isosteres in Drug Discovery", Drug Discov., Jun. 2003, 8(12), 551-556.
Song, et al., "Organometallic Methods for the Synthesis and Functionalization of Azaindoles", Chem. Soc. Rev., Feb. 2007, 36, 1120-1132.
Starkov, et al., "Catalytic Electrophilic Halogenation of Siyl-Protected and Terminal Alkynes: Trapping Gold (I) Acetylides vs. a Bronsted Acid-Promoted Reaction", Adv. Synth. Catal., Nov. 2012, 354, pp. 3217-3224.
Sugita, et al., "A Novel Reduction of Zinc(II) Chloride with Samarium Metal and its Application to Silylation of 1-Alkynes. Synlett", 1996, vol. 7, 637-639.
Tamao, et al., "Silole Derivatives as Efficient Electron Transporting Materials", J. Am. Chem. Soc., Nov. 1996, 118(47), 11974-11975.
Ting, et al., "Arylfuoroborates and Alkylfluorosilicates as Potential PET Imaging Agents: High-Yielding Aqueous Biomolecular 18F-Labeling", J. Am. Chem. Soc., Sep. 2005, 127(38), 13094-13095.
Toutov, et al., Silylation of C—H Bonds in Aromatic Heterocycles by an Earth-Abundant Metal Catalyst", Nature, Feb. 2015, 518, 80-84.".
Tsuchimoto, et al., "Dehydrogenative Silylation of Terminal Alkynes with Hydrosilanes under Zinc-Pyridine Catalysis", Adv. Synth. Catal., 2012, vol. 354, 2959-2964.
Ulrich, et al., Elektrophile Sillyberung Elektronenenreicher Heteroaromaten", Synthesis, Nov. 1984, 929-930.".
Voronkov, et al., "Dehydrocondensation of Trialkylsilanes with Acetylene and Monosubstituted Acetylenes", J. Organomet. Chem., 1984, vol. 264, 39-8.
Wang, et al., "Transition-Metal-Free Synthesis of Alternating Thiophene-Perfluoroarene Copolymers", J. Am. Chern. Soc., Feb. 2006,128(8), 2536-2537.
Wang, et al., "Unique a-Bond Metathesis of Silylalkynes Promoted by an ansa-Dimethylsilyl and Oxo-Bridged Uranium Metallocene", J. Am. Chem. Soc., Jun. 2006, vol. 128(29), 9350-9351.
Watanabe et al. "Simple and convenient method for preparing functionalized network organopolysilanes" Journal of Materials Chemistry, 1991, vol. 1, pp. 483-484.
Weickgenannt, et al., "Potassium tert-Butoxide-Catalyzed Dehydrogenative Si-0 Coupling: Reactivity Patten and Mechanism of an Underappreciated Alcohol Protection", Chem. Asian J., Jan. 2009,4(3), 406-410.
Whisler, et al., "Beyond Thermodynamic Acidity: A Perspective on the Complex-Induced Proximity Effect (CIPE) in Deprotonation Reactions", Angew. Chem., Int Ed., Apr. 2004, 43(17), 2206-2225.
Yamaguchi, et al., "Heterogeneously Catalyzed Aerobic Cross-Dehydrogenative Coupling of Terminal Alkynes and Monohydrosilanes by Gold Supported on OMS-2", Angew Chem., 2013, 52, 5627-30.
Zhang, et al.,"Thiophene-Based Conjugated Oligomers for Organic Solar Cells", J. Mater. Chem., Sep. 2011, 21, 17590-17600.
Zhao, et al., "Directed Ortho Metalation-Based Methodology. Halo-, Nitroso-, and Baro-Induced ipso-Desilylation. Link to an in situ Suzuki Reaction", Org. Lett., May 2005, 7(13), 2523-2526+F54.
Zhao, et al., "Directed Ortho Metalation-Based Methodology. Halo-, Nitroso-, and Boro-Induced ipso-Desilylation. Link to an in situ Suzuki Reaction", Org. Lett., May 2005, 7(13), 2523-2526.
U.S. Appl. No. 15/889,295, filed Feb. 6, 2018.
U.S. Appl. No. 14/043,917, filed Oct. 2, 2013.

Magnetic Field / G f1 (ppm)

SILYLATIONS OF AROMATIC SUBSTRATES WITH BASE-ACTIVATED ORGANOSILANES

CROSS REFERENCE TO RELATED APPLICATIONS

This application is a continuation of U.S. patent application Ser. No. 15/889,295, filed Feb. 6, 2018 that is a continuation of U.S. patent application Ser. No. 14/043,917, filed Oct. 2, 2013, that issued as U.S. Pat. No. 9,908,840 on Mar. 6, 2018, that claims priority to U.S. Patent Application Ser. Nos. 61/708,931, filed Oct. 2, 2012, 61/818,573, filed May 2, 2013, and 61/865,870, filed Aug. 14, 2013, the contents of each of which is incorporated by reference in its entirety for all purposes.

TECHNICAL FIELD

One aspect of the present disclosure is directed at processing materials derived from biomass, including biomass (e.g. lignin, sugar), biomass liquifaction, biopyrolysis oil, black liquor, coal, coal liquifaction, natural gas, or petroleum process streams. In this way, the present disclosure is directed to systems and methods for reductively cleaving C—O, C—N, and C—S bonds in aromatic compounds, such as those found in such process streams. In another aspect, the present disclosure is also directed at methods for silylating substrates comprising aromatic moieties.

BACKGROUND

In the past few decades, the growing demand for energy combined with declining fossil fuel reserves has created a tremendous surge in interest for efficient manufacturing of fuels and bulk chemicals from renewable bioresources. The natural heterobiopolymer lignin has developed into a major target for cost-efficient biomass conversion because the repeating aromatic ether structural units could offer high energy content products and potential access to useful derivatives for fine chemical applications. However, at present, utilization of lignin is clearly limited since current technology does not allow for efficient decomposition into its constituent building blocks with the desired selectivity. One of the major challenges associated with such a process is the need to reductively cleave the different types of strong aromatic C—O bonds present in lignin (FIG. 1), which is also a relevant problem for the liquefaction of coal.

Additional challenges are faced in the processing of coal and petroleum products, where increasing environmental regulations require the virtual elimination of sulfur from feedstreams. Combustion of sulfur leads to sulfur oxides with are environmentally undesirable in their own rights, but also tend to poison precious metal catalysts used, for example, in catalytic converters. There is a high interest in technologies which not only depolymerize biomass, but which act to reduce or eliminate residual sulfur from these feedstock matrices.

Ni catalysts are known to provide selective reductive transformations involving aryl-oxygen bonds, but only at loadings of 5-20%, and at these levels the use of Ni and other transition-metal catalysts are problematic, both from an economic and environmental perspective. Further, such catalysts are not reported to be useful on C—N or C—S bonds. And while it would be beneficial to have a general methodology for aromatic C—O bond cleavage that does not employ nickel or other transition metal catalysts, the only known alternative approaches for metal free ether cleavage at relatively low temperatures rely on excess alkali metals or electrocatalytic processes that tend to be costly, unsustainable and impractical.

Separately, the ability to silylate organic moieties has attracted significant attention in recent years, owing to the utility of the silylated materials in their own rights, or as intermediates for other important materials used, for example, in agrichemical, pharmaceutical, and electronic material applications. Further, the ability to functionalize polynuclear aromatic compounds with oganosilanes provides opportunities to take advantage of the interesting properties of these materials.

Historically, the silylation of aromatic compounds has been achieved via free radical processes involving thermally, photochemically, or by otherwise derived radical sources. More recently, the transition metal mediated aromatic C—H silylation has been described, with different systems described based on, for example, Co, Rh, Ir, Fe, Ru, Os, Ni, Pd, and Pt catalysts. But for certain electronic applications, the presence of even low levels of such residues can adversely affect the performance of the silylated materials. Similarly, in certain pharmaceutical applications, limits on residual transition metals are fairly strict, and the ability to avoid them entirely offers benefits during post-synthesis work-up.

The present disclosure is directed at solving at least some of the problems in both of these areas.

SUMMARY

Various embodiments of the present disclosure provide chemical systems for reducing C—O, C—N, and C—S bonds, each system comprising a mixture of (a) at least one organosilane and (b) at least one strong base, said system being substantially free of a transition-metal compound, and said system optionally comprising at least one molecular hydrogen donor compound, molecular hydrogen, or both.

Other embodiments provide methods of reducing C—X bonds in a an organic substrate, where X is O, N, or S, each method comprising contacting a quantity of the substrate comprising at least one C—O, C—N, or C—S bond with a chemical system comprising a mixture of (a) at least one organosilane and (b) at least one strong base, under conditions sufficient to reduce the C—X bonds of at least a portion of the quantity of the substrate; wherein said chemical system is substantially free of a transition-metal compound, and said chemical system optionally comprising at least one molecular hydrogen donor compound, molecular hydrogen, or both.

Various other embodiments of the present disclosure provide systems for silylating organic compounds, each system comprising a mixture of (a) at least one organosilane and (b) at least one strong base, said system being optionally free of a transition-metal compound.

Other embodiments provide methods, each method comprising contacting an organic substrate comprising an aromatic moiety with a mixture of (a) at least one organosilane and (b) at least one strong base, under conditions sufficient to silylate the substrate; wherein said mixture and substrate are optionally free of a transition-metal compound.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 4-17 are $^1$H and $^{13}$C-NMR spectra or HSQC spectra of some of the compounds prepared by the methods described herein. Unless otherwise states, spectra were taken for compounds dissolved in CDCl$_3$ at 300 MHz ($^1$H) and 126 MHz ($^{13}$C). Peaks marked with asterisks are deemed to be associated with impurities in the respective sample.

FIG. 4 are (A)$^1$H and (B)$^{13}$C-NMR spectra of toluene and its triethylsilylation products.

FIG. 5 are (A)$^1$H and (B)$^{13}$C-NMR spectra of mesitylene and its triethylsilylation product.

FIG. 6 are (A)$^1$H and (B)$^{13}$C-NMR spectra of o-triethylsilyldiphenyl ether.

FIG. 7 are the HSQC spectra of (A) 2-methoxynaphthalene and (B) the product of its reaction with triethylsilane, as described in Example 6.2.2; characterized as triethyl-(3-methoxynaphthalen-2-yl)silane.

FIG. 9 are the HSQC spectra of (A) thioanisole (B) the product of its reaction with triethylsilane, as described in Example 6.2.4.

FIG. 10 is the HSQC spectra of the reaction product of N-methylindole with triethylsilane, as described in Example 6.3.1, characterized as 1-methyl-2-(triethylsilyl)-1H-indole FIG. 11 is the HSQC spectra of the reaction product of N-methylindole with triethylsilane, as described in Example 6.3.2, characterized as 1-methyl-3-(triethylsilyl)-1H-indole.

FIG. 12 is the HSQC spectra of the reaction product of 1-methyl-H-pyrrolo[2,3-b]pyridine with triethylsilane, as described in Example 6.3.6, characterized as 1-methyl-2-(triethylsilyl)-1H-pyrrolo[2,3-b]pyridine.

FIG. 13 is the HSQC spectra of the reaction product of 1,2-dimethylindole with triethylsilane, as described in Example 6.3.7.

FIG. 14 is the HSQC spectra of the reaction product of 1-phenylpyrrole with triethylsilane, as described in Example 6.3.9, characterized as 9,9-diethyl-9H-benzo[d]pyrrolo[1,2-a][1,3]azasilole.

FIG. 15 is the HSQC spectra of the reaction product of benzofuran with triethylsilane, as described in Example 6.3.10, characterized as benzofuran-2-yltriethylsilane.

FIG. 17 is the HSQC spectra of the reaction product of dibenzothiophene with triethylsilane, as described in Example 6.3.13, characterized as 4-(triethylsilyl)dibenzopthiophene.

DETAILED DESCRIPTION OF ILLUSTRATIVE EMBODIMENTS

Figure 1A:
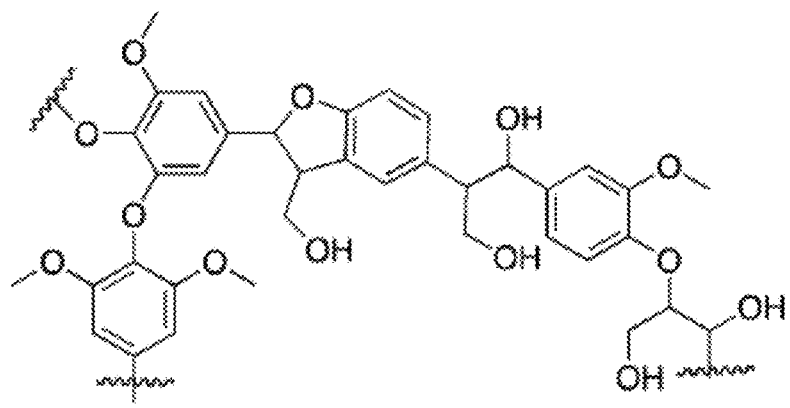
FIGS. 1A and 1B illustrate examples of C—O bonds such as are present in hardwood lignins.

The present disclosure is founded on a set of reactions, each of which relies on simple mixtures of organosilanes and strong bases, which together form in situ reductive systems (the structure and nature of which is still completely unknown) able to activate C—O, C—N, and C—S bonds in the liquid phase, or silylate aromatic substrates, without the necessary presence of transition metal catalysts, UV radiation or electrical discharges. These reactions are relevant as an important advance in developing practical methods for the decomposition of biomass-based feedstreams into aromatic feedstocks and fuels. Importantly this reaction is of great interest since it produces only environmentally benign silicates as the byproduct and avoids toxic metal waste streams as would be observed with nearly all other approaches proposed in the literature towards this end. In the case of sulfur compounds, a double C—S activation protocol has been observed under the reaction conditions leading to a formal removal of the sulfur atom from the substrate molecule. This remarkable observation is also relevant to the desulfurization of sulfur-containing contaminants in crude oil streams which is of great interest and high value. In other aspects, these reactions are relevant as an important advance in developing practical methods for the preparation of silylated products important for pharmaceutical and electronics applications. The remarkable facility and regiospecificity exhibited by at least some of these systems provides a useful tool in the kit of chemists in these fields.

The present disclosure may be understood more readily by reference to the following description taken in connection with the accompanying Figures and Examples, all of which form a part of this disclosure. It is to be understood that this disclosure is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the disclosure herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the disclosure which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the disclosure that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments directed to the reductive cleavage of aromatic C—O, C—N, and C—S bonds and provided in terms of "consisting essentially of," the basic and novel characteristic(s) is the operability of the methods (or the systems used in such methods or the compositions derived therefrom) as a transition metal-free method of effecting the reductive cleavage of C—O, C—N, or C—S bonds. For those embodiments directed to silylation reactions provided in terms of "consisting essentially of," the basic and novel characteristic(s) is the facile operability of the methods (or the systems used in such methods or the compositions derived therefrom) to silylate aromatic organic moieties.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety).

Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2, 7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl," and "aralkyl" are as defined above.

The terms "cyclic" and "ring" refer to alicyclic or aromatic groups that mayor may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which a double bond may or may not be contained within the ring structure.

The terms "halo," "halide," and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene"and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_1$-$C_{24}$ aryl)substituted carbamoyl (—(CO)—N ($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—

NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_1$-$C_{24}$ aryl) substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_1$-$C_{24}$ aryl)-substituted thiocarbamoyl, carbamido (—NH—(CO)—NH$_2$), cyano(—C≡N), cyanato (—O—C=N), thiocyanato (—S—C=N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_1$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$OH), sulfonate(SO$_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl-SO$_2$—N(H) alkyl), $C_1$-$C_{24}$ dialkylaminosulfonyl-SO$_2$—N(alkyl)$_2$, $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—PO$_2$), and phosphine (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_1$-$C_{24}$ aryl (preferably $C_1$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline.

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The present disclosure includes embodiments related chemical systems and methods for reducing C—O, C—N, and C—S bonds. Specific embodiments provide chemical systems for reducing C—O, C—N, and C—S bonds, each system comprising a mixture of (a) at least one organosilane and (b) at least one strong base; said system optionally comprising at least one molecular hydrogen donor compound, molecular hydrogen, or both, and said system preferably being substantially free of a transition-metal compound. While certain embodiments provide that transition metals, including those capable of catalyzing silylation reactions, may be present within the systems or methods described herein at levels normally associated with such catalytic activity, the presence of such metals (either as catalysts or spectator compounds) is not required and in many cases is not desirable. As such, in preferred embodiments, the system and methods are "substantially free of transition-metal compounds." As used herein, the term "substantially free of a transition-metal compound" is intended to reflect that the system is effective for its intended purpose of reducing C—O, C—N, and C—S bonds even in the absence of any exogenous (i.e., deliberately added or otherwise) transition-metal catalyst(s). Unless otherwise stated, then, the term "substantially free of a transition-metal compound" is defined to reflect that the total level of transition metal within the reducing system, independently or in the presence of organic substrate, is less than about 50 ppm, as measured by ICP-MS as described in Example 2 below. Additional embodiments also provide that the concentration of transition metals is less than about 100 ppm, 50 ppm, 30 ppm, 25 ppm, 20 ppm, 15 ppm, 10 ppm, or 5 ppm to about 1 ppm or 0 ppm. As used herein, the term "transition metal" is defined to include Co, Rh, Ir, Fe, Ru, Os, Ni, Pd, Pt, Cu, or combinations thereof. In further specific independent embodiments, the concentration of Ni, as measured by ICP-MS, is less than 25 ppm, less than 10 ppm, less than 5 ppm, or less than 1 ppm.

Also, as used herein, the terms "reducing (as in C—O, C—N, and C—S bonds)" or "reductive cleavage" refer to a chemical transformation where the O, N, or S moieties are replaced by less electronegative groups, for example and including H, D, or Si.

While it may not be necessary to limit the system's exposure to water and oxygen, in some embodiments, the chemical system and the methods are done in an environment substantially free of water, oxygen, or both water and oxygen. Unless otherwise specified, the term "substantially free of water" refers to levels of water less than about 500 ppm and "substantially free of oxygen" refers to oxygen levels corresponding to partial pressures less than 1 torr. Where stated, additional independent embodiments may provide that "substantially free of water" refers to levels of water less than 1.5%, 1%, 0.5%, 1000 ppm, 500 ppm, 250 ppm, 100 ppm, 50 ppm, 10 ppm, or 1 ppm and "substantially free of oxygen" refers to oxygen levels corresponding to partial pressures less than 50 torr, 10 torr, 5 torr, 1 torr, 500 millitorr, 250 millitorr, 100 millitorr, 50 millitorr, or 10 millitorr.

While not intending to be bound by the correctness of any proposed mechanism of interaction (especially since its role is yet unknown), it appears that the presence of hydrogen during the reducing process is important for the reductive cleavages to proceed, even if only to the extent that hydrogen appears to be generated during the reduction process (see infra), and its presence seems to improve (if not be necessary for) or its absence detracts from the reductive cleavages described herein. Interesting, the addition of molecular hydrogen donor compounds also has a positive effect on the system in reducing C—O, C—N, and C—S bonds (see, e.g., Example 5.9, Table 2, Entry 18), while hydride donors (including, e.g., borohydrides, aluminum or tin hydrides) apparently do not (e.g., see Example 5.12, Table 4, Entries 3, 5-7). Exemplary hydrogen donor compounds may include compounds such as 1,3-cyclohexadiene, 1,4-cyclohexadiene, 1,2-cyclohexadiene, 1,4-cyclohexadiene 1,2-dihydronaphthalene, 1,4-dihydronaphthalene, 1,2-dihydroquinoline, 3,4-dihydroquinoline, 9,10-dihydroanthracene, or tetralin.

The mechanism by which the system and methods operate is not yet understood, and the inventors are not bound by the correctness or incorrectness of any particular theory as to mode of mechanism, but some observations point to the possibility that the active reductant silicon species may be an organosilicate. Further, as described herein, the reductive cleavage is also often accompanied by the presence of silylation of the organic substrate, though at this point it is unclear whether such species are intermediates, co-products, or both. But it does appear that the presence of hydrogen donors and hydrogen itself plays in an important role in determining the extent of conversion and the relative amounts of cleavage and silylation; see Example 5.9, Table 2.

The importance of hydrogen or hydrogen donors can be seen in the results of a series of experiments in which the presence of hydrogen or hydrogen donors were specifically manipulated. As described in Example 3 below, many experiments were conducted in sealed glass containers. Headspace analysis of these sealed reaction mixtures indicated the formation of $H_2$. To ascertain its importance, additional experiments were conducted where the reaction was opened to an atmosphere of argon, whereupon a dramatic decrease in reductive cleavage product formation occurred that was offset by increased silylation (Example 5.9, Table 2, compare Entries 4-6). This result suggested that dihydrogen might be important to prevent decomposition of the active reducing species. In a search to further modulate the selectivity by shutting down radical pathways, experiments were conducted using 1,4-cyclohexadiene as a non-polar hydrogen donor co-solvent, resulting in the exclusive formation of 2 with 95% yield (Example 5.9, Table 2, Entry 18). These results demonstrate the ability to tune the selectivity of the reaction by altering the reaction conditions.

As used herein, the term "organosilane" refers to a compound or reagent having at least one silicon-hydrogen (Si—H) bond. The organosilane may further contain a silicon-carbon, a silicon-oxygen, a silicon-nitrogen bond, or a combination thereof, and may be monomeric, or contained within an oligomeric or polymeric framework, including being tethered to a heterogeneous or homogeneous support structure. In certain embodiments, these organosilane may comprise at least one compound of Formula (I) or Formula (II):

$$(R)_{4-m}Si(H)_m \quad\quad (I)$$

$$R-[SiH(R)-O-]_n-R \quad\quad (II)$$

where: m is 1, 2, or 3, preferably 1;

n is in a range of from about 5 to about 500, from about 10 to about 100 or from about 25 to about 50; and R is independently optionally substituted $C_{1-12}$ alkyl or heteroalkyl, $C_{5-20}$ aryl or heteroaryl, $C_{6-30}$ alkaryl or heteroalkaryl, $C_{6-30}$ aralkyl or heteroaralkyl, —O—$C_{1-12}$ alkyl or heteroalkyl, —O—$C_{5-20}$ aryl or heteroaryl, —O—$C_{6-30}$ alkaryl or heteroalkaryl, —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon. Exemplary, non-limiting organosilanes include $(R)_3SiH$, where R is $C_{1-6}$ alkyl, particularly triethylsilane and tributylsilane, mixed aryl alkyl silanes, such as $PhMe_2SiH$, and polymeric materials, such as polymethylhydrosiloxane (PMHS).

As used herein, the term "strong base" refers to a compound having a strong affinity for hydrogen atoms especially, but not only, in non-aqueous media. In specific independent embodiments, the at least one strong base comprises an alkali or alkaline metal hydride or alkoxide. It should be appreciated, then, that this definition is not strictly limited to the classic conjugate acid-base model—since the conjugate acid of hydride would be dihydrogen. One measure of this "strong affinity" may be that the strong base, if reacted with water, would react to the practically complete formation of hydroxide therefrom. Other "strong bases" may be considered as including alkyl lithium compounds or amide ions, for example potassium bis(trimethylsilyl) amide.

There appears to be a hierarchy of activity related to the counterion of the strong base, such that the use of cesium and potassium hydrides and alkoxides are preferred. Exemplary hydrides useful in the present disclosure include potassium hydride. Similarly, the effect of temperature on the effectiveness of reaction with hydrides may be seen in Example 5.9, Table 2, entries 13 and 24, where the reaction of dibenzofuran with KH conducted at 100° C. results in low conversion rates and low levels of formation of the monocleaved product, biphenyl-2-ol, whereas conducting a similar experiment at 165° C. resulted in essentially quantitative conversion to predominantly that product.

Useful alkoxides include those comprising a $C_{1-12}$ linear or branched alkyl moietird or a $C_{5-10}$ aromatic or heteroaromatic moieties, for examples methoxide, ethoxide, propoxide, butoxide, 2-ethyl-hexyloxide, or benzyloxide. Each of these appears to give comparable reactivity (see, e.g., Example 5.9, Table 2, compare Entries 17, 25-26, and 28). Further, the choice of the counter cation also impacts the effectiveness of the activity of the chemical system, such that potassium or cesium alkoxides are preferred. More specifically, potassium methoxide, ethoxide, and tert-butoxide and cesium 2-ethyl-hexyl alkoxide have been shown to be particularly effective in this role. By comparison, the reaction of $Et_3SiH$ with lithium or sodium tert-butoxide provides no conversion of dibenzofuran to the bisphenyl-2-ol (see, e.g., Example 5.9, Table 2, Entries 29-31) suggesting that the counter ion plays a critical role in the generation of the active reductant species and, possibly, in activation of the substrate ether. Similarly, conducting reactions with potassium tert-butoxide in the presence of sufficient 18-crown-6 to act as a potassium chelator resulted in nearly complete inhibition of the reaction (Table 4, Example 5.12, Entry 2).

While the relative amounts of organosilane and strong base is not believed to be particularly important, so long as both are present in sufficient quantities, in certain embodiments, the organosilane and the at least one strong base are present together at a molar ratio, with respect to one another, in a range of from about 20:1 to about 1:2. In other embodiments, these ratios may be on the order of about 5:1 to about 1:2, from about 3:1 to about 1:3, or from about 3:2 to about 2:3. In still other embodiments, the system has been shown to be effective when the organosilane is used as a solvent for the reductions. Also, the intended organic substrate for the chemical reductions may be used as the solvent. In certain embodiments, the chemical system may be seen as including an organic substrate containing oxygen, nitrogen, sulfur, or a combination thereof, including where the organic substrate is contained within a biomass (e.g. lignin, sugar), biomass liquifaction, biopyrolysis oil, black liquor, coal, coal liquifaction, natural gas, or petroleum batch or process stream.

The reducing system may further comprise a solvent other than the organosilane. As shown thus far, preferred solvents appear to be those that are aprotic. Also, the reductive cleavage reactions appear also to favor higher temperatures, though are not necessarily limited to this constraint (for example, cesium ethyl-hexyl alkoxide has been shown to reduce C—O bonds with triethylsilane at ambient room temperature). Accordingly, solvents having boiling points (at one atmosphere pressure) in a range bounded at the lower end by a value of about 25° C., 50° C., 75° C., 100° C., 125° C., 150° C., 175° C., or 200° C., and bounded at the upper end by a value of about 450° C., 425° C., 400° C., 375° C., 350° C., 325° C., 300° C., 275° C., or 250° C. appear to be preferred. One exemplary, non-limiting, boiling point range, then, is from about 80° C. to about 350° C. Exemplary, non-limiting solvents include benzene, toluene, xylene, mesitylene, naphthalene, methyl cyclohexane, and dioxane.

As will be described further below, these chemical reducing systems are capable of reductively cleaving C—O, C—N, or C—S bonds. It certain embodiments, these are alkyl C—O, C—N, or C—S bonds or aromatic C—O, C—N, or C—S bonds. In the context of alkyl or aromatic C—O, C—N, or C—S bonds, the terms "alkyl" and "aromatic" refer to the nature of the carbon to which the oxygen, nitrogen, or sulfur atoms are bonded. As used herein, the general term "aromatic" refers to the ring moieties which satisfy the Hückel 4n+2 rule for aromaticity, and includes both aryl (i.e., carbocyclic) and heteroaryl structures, including aryl, aralkyl, alkaryl, heteroaryl, heteroaralkyl, or alkheteroaryl moieties. Further, aromatic C—O, C—N, or C—S bonds can be configured to be endocyclic within the ring system (e.g., pyridine, furan, pyrrole, or thiophene) or exocyclic to the aromatic ring structure (e.g., as in anisole).

To this point, the disclosure has been described in terms of the chemical systems capable of reducing C—O, C—N, C—S bonds, or silylating aromatic compounds or moieties, or a combination thereof, but it should also be apparent that the disclosure also includes the methods of carrying out these transformations.

Methods for Reducing C—O, C—N, C—S Bonds

That is, various additional embodiments include those methods where an organic substrate comprising C—O, C—N, C—S bonds, or a combination thereof, are contacted with any of the chemical systems described above under conditions sufficient to reduce at least a portion of these bonds. That is, certain embodiments provide methods of reducing C—X bonds in an organic substrate, where X is O, N, or S, said method comprising contacting a quantity of the substrate comprising at least one C—O, C—N, or C—S bond with a chemical system comprising a mixture of (a) at least one organosilane and (b) at least one strong base, under conditions sufficient to reduce the C—X bonds of at least a portion of the quantity of the substrate; wherein said chemical system is preferably substantially free of a transition-metal compound, and said chemical system optionally comprising at least one molecular hydrogen donor compound, molecular hydrogen, or both. In this context, the terms "reducing" and "reductive cleavage" carry the same definition as described above; i.e., comprising chemical transformations wherein at least some portion of the O, N, or S moieties are replaced by less electronegative groups, for example and including H, D, or Si. The specific nature of these chemical transformations is described herein.

In either case, in the context of the methods, the term "substantially free of a transition-metal compound" carries the same connotations and related embodiments as described supra for the chemical system; i.e., reflecting that the methods are effectively conducted in the absence of any deliberately added transition-metal catalyst(s). Unless otherwise stated, when describing a method or system, the term is defined to reflect that the total level of transition metal, as measured by ICP-MS as described in Example 2 below, is less than about 50 ppm. Additional embodiments also provide that the concentration of transition metals is less than about 100 ppm, 50 ppm, 30 ppm, 25 ppm, 20 ppm, 15 ppm, 10 ppm, or 5 ppm to about 1 ppm or 0 ppm. As used herein, the term "transition metal" is defined to mean Co, Rh, Ir, Fe, Ru, Os, Ni, Pd, Pt, Cu, or combinations thereof. In further independent embodiments, the concentration of Ni, as measured by ICP-MS, is less than 25 ppm, less than 10 ppm, less than 5 ppm, or less than 1 ppm. Noting here that certain embodiments of the chemical system may comprise the at least one organosilane, and strong base, and optionally further comprise at least one molecular hydrogen donor, at least one substrate, additional solvent, or a combination thereof, it should be appreciated that independent embodiments provide that the levels of transition metals are maintained below the levels just described, when considering each of these mixture combinations.

In the context of the cleavage methods, the term "substantially free of water and/or oxygen" carries the same connotations and related embodiments as described above for the system itself. Similarly, the same organosilanes, strong bases, solvents, proportions, and operating conditions described as useful for the system apply to the methods of using the systems. Additionally, as shown in the Examples, the system has shown to be useful when operated such that the organosilane and C—X bonds in the substrate are present in a ratio of from about 1:2 to about 10:1 and where the strong base and C—X bonds in the substrate are present in a range of from about 1:2 to about 10:1. A review of the results shown in Example 5.9, Table 2 provides a helpful indicator as to the effect of the ratios within these limits, and each ratio or combination thereof represents an individual embodiment of this disclosure.

In those methods which have been described in terms of being conducted "under conditions sufficient to reduce the C—X bonds of at least a portion of the quantity of the substrate," such conditions include heating the contacted organic substrate and chemical system to a temperature in a range of from about 25° C. to about 450° C. In independent embodiments, this heating can be done at at least one temperature in a range from about 25° C., about 50° C., about 75° C., about 100° C., about 150° C., or about 200° C. to about 450° C., about 400° C., about 350° C., about 300° C., about 250° C., about 200° C., or about 150° C., including the temperatures exemplified herein. It is preferred, but not required, that this heating is done in a solvent at a temperature below the boiling point of the solvent, and preferably, but not necessarily, in a solvent at a temperature below the boiling point of the solvent at one atmosphere pressure.

The term "to reduce the C—X bonds of at least a portion of the quantity of the substrate" refers to the condition where the cleavage of an individual C—X bond proceeds to less than quantitative yield, to the condition where the cleavage of an individual C—X bond proceeds to quantitative yield, to the condition where multiple C—X bonds exist in the substrate (individual compound or mixture thereof) and only one type of C—X bonds are cleaved, or a combination thereof. For purposes of this description, unless otherwise stated, the reaction conditions are considered sufficient if at least 5% of at least one C—X bond (where x=O, N, or S) is cleaved by the reaction. Higher yields are preferred, especially when dealing with individual compounds, so additional independent embodiments provide the reaction conditions are considered sufficient if at least 10%, at least 20%, at least 30%, at least 40%, at least 50%, at least 60%, at least 70%, at least 80%, at least 90%, or at least 95% of at least one C—X bond is cleaved by the reaction. In related embodiments, the method may produce a product in which at least one of the C—X bonds is reduced by an amount ranging from a lower value of about 10%, about 20%, about 30%, about 40%, about 50%, or about 60% and an upper value of about 100%, about 95%, about 90%, about 80%, about 70%, about 60%, about 50%, or about 40%, relative to the amount originally present in the substrate compound.

Figure 1B:
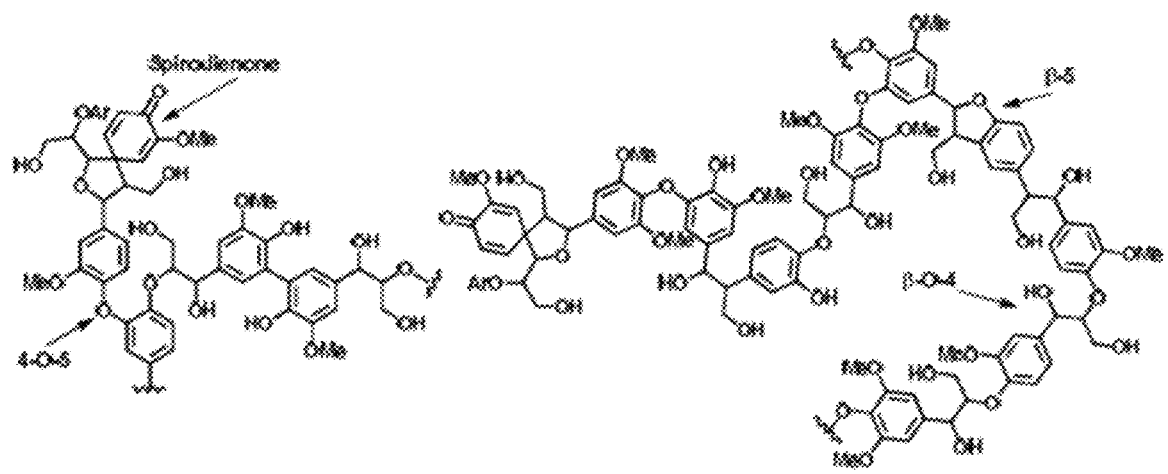
Figure 1C:
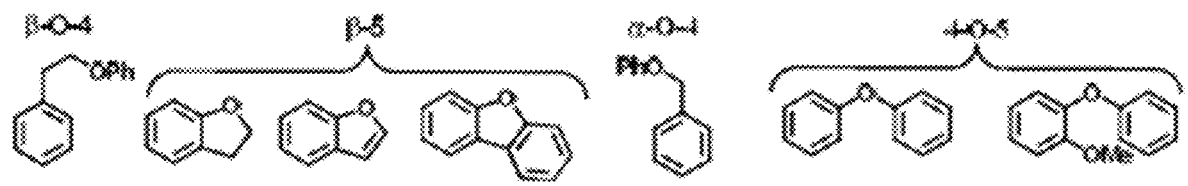
FIG. 1C illustrates some of the model compounds discussed in this application for critical C—O linkages.

Such high yields of any individual linkage may not be necessary where the substrate is an extended array of interconnected aromatics, such as found in lignin (see, e.g., FIG. 1), coal, or petroleum products, in which case success may be measured by the reduction in molecular weight of the initial substrates.

The methods also cleave different C—X bonds to different efficiencies, under otherwise nominally the same conditions. For example, as seen in Example 5.11, Schemes 1 and 2, aliphatic and aromatic C—O bonds behave differently, when contained within the same substrate. Further, whereas C—O and C—N bonds, by and large, produce products having residual alcohol or amine linkages, the same reaction conditions applied to substrates having C—S bonds generally result in products from which the S has been completely removed. Such desulfurization occurs even in substrates which are historically difficult to desulfurize (e.g., hindered dibenzothiophenes).

The methods appear to be operable on organic aromatic substrates, wherein the organic substrate comprises at least one C—O bond, at least one C—N bond, at least one C—S bond, or a combination of such C—O, C—N, or C—S bonds. While the methods have been validated using a variety of aromatic or heteroaromatic substrates, the C—O, C—N, or C—S bonds which are cleaved are not necessarily aromatic C—O, C—N, or C—S bonds. In some embodiments, at least one of the C—O, C—N, or C—S bonds comprises an aromatic carbon. Within this set, the aromatic C—O, C—N, or C—S bonds may be endocyclic or exocyclic to an aromatic ring. The terms "endocyclic" and "exocyclic" refer to the position of the O, N, or S with respect to the aromatic ring system. For example, "endocyclic" refers to a bond in which both the carbon and the respective oxygen, nitrogen, or sulfur atoms are contained within the aromatic ring; furan, pyrrole, and thiophene contain endocyclic C—O, C—N, and C—S bonds, respectively. Accordingly, the organic substrate may comprise an optionally substituted heteroaryl moiety which includes, but are not limited to, a furan, pyrrole, thiophene, benzofuran, benzopyrrole, benzothiophene, 2,3-dihydrobenzofuran, xanthene, 2,3-dihydrobenzopyrrole, 2,3-dihydrobenzothiophene, dibenzofuran, dibenzopyrol, dibenzothiophene, or hindered dibenzofuran, dibenzopyrrole, or dibenzothiophene structure. The term "hindered dibenzofuran, dibenzopyrrole, or dibenzothiophene structure" refers to the presence of optionally substituted aryl, alkyl, or alkoxy substituents in the 2,6 positions of the dibenzofuran, dibenzopyrrole, or dibenzothiophene. 2,6-Dimethyl dibenzothiophene is one important example of a hindered dibenzothiophene.

By contrast, the term "exocyclic" refers to a bond in which both the carbon is contained within the aromatic rings system, but the respective oxygen, nitrogen, or sulfur atoms are not, and (in the case of nitrogen) vice versa. For example, phenol, phenylamine (aniline), 1-methyl-1H-pyrrole, and benzenethiol contain exocyclic aromatic C—O, C—N, and C—S bonds, respectively. Exemplary organic substrates comprise, but are not limited to, optionally substituted phenyl ethers, phenyl amines, phenyl sulfides, naphthyl ethers, naphthyl amines, or naphthyl sulfides moiety, N-alkyl or N-aryl pyrroles, or combinations thereof.

As stated above, the methods are also operable on organic aromatic substrates, wherein the C—O, C—N, or C—S bonds which are cleaved are aliphatic (alkyl)C—O, C—N, or C—S bonds. Typically, but not necessarily, the aliphatic (alkyl)C—O, C—N, or C—S bonds are those in which the heteroatom is also joined by an aromatic C—O, C—N, or C—S bond anisole (Ph-O—CH$_3$) and 1-methyl-1H-pyrrole are but two examples. Interestingly, and for reasons not entirely understood, the effect of the aromatic moiety on bond cleavage has also been observed to extend beyond its neighboring effect on the heteroatom. For example, in two examples:

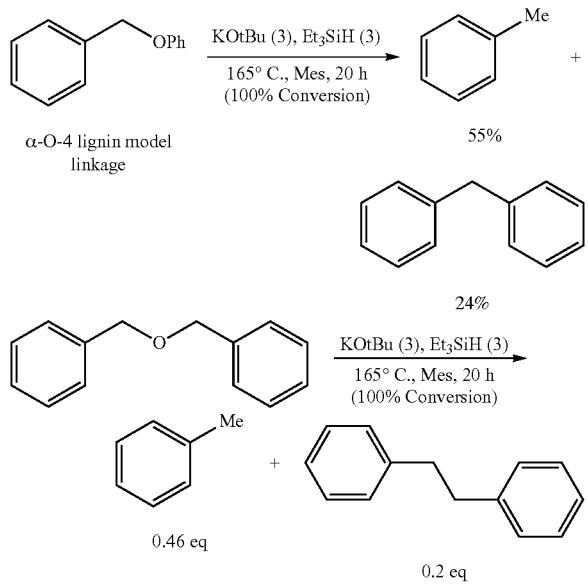

Additional embodiments provide that these methods may be applied to organic substrates batchwise or in a flowing stream, either individually, or as part of a mixture. Indeed, it is particularly attractive to apply these methods where the organic substrate is contained within a petroleum, coal, natural gas, biomass (e.g. lignin, sugar), biopyrolysis oil, biomass liquifaction, or black liquor batch or process stream, or where such batch or process stream provides the solvent for the reaction.

It is recognized that the systems and reactions which provide for the cleavage of the cleavage of the C—O, C—N, C—S bonds can also provide silylation of the aromatic substrates or even the aromatic solvents. This latter silylation feature is the subject of a co-filed and co-pending U.S. patent application Ser. No. 14/043,929, filed Oct. 2, 2013, entitled "Transition-Metal-Free C—H Silylation of Aromatic Compounds", now U.S. Pat. No. 9,000,167, which issued Apr. 7, 2015, which is also incorporated by reference in its entirety for all purposes. As used herein, the term "silylating" refers to the forming of carbon-silicon bonds, in a position previously occupied by a carbon-hydrogen bond, generally a non-activated C—H bond. The ability to replace directly a C—H bond with a C—Si bond, under the conditions described herein, is believed to be unprecedented. The mechanism by which the system and methods operate is not yet understood, for example, whether the silylation is an intermediate step or a co-product or by-product of the cleavage reactions, but it does appear that the relative contribution of each manifold can be manipulated by the reaction conditions. For example, other factors being similar or equal, it appears that higher temperatures and longer reaction times favor the cleavage of C—O, C—N, C—S bonds over the silylation reactions. Similarly, absence of hydrogen and hydrogen donor molecules and use of substoichiometric quantities of the strong base (relative to the organosilane) appear to favor the silylation reactions and disfavor the C—X cleavages.

Methods for Silylating Aromatic Compounds or Moieties

Various additional embodiments include those methods where an organic substrate comprising an aromatic moiety is contacted with any of the chemical systems described above under conditions sufficient to silylate at least a portion of the substrate. That is, certain embodiments provide methods, each method comprising contacting an organic substrate comprising an aromatic moiety with a mixture of (a) at least one organosilane and (b) at least one strong base, under conditions sufficient to silylate the substrate; wherein said mixture and substrate are optionally substantially free of a transition-metal compound. These embodiments are generally done in the liquid phase, without UV irradiation or electric or plasma discharge conditions.

In some embodiments, the conditions sufficient to silylate the organic substrate comprise heating the substrate with a mixture of (a) the at least one organosilane and (b) the at least one strong base at a temperature in a range of about 10° C. to about 165° C. In some cases, the temperatures may be applied in a range of from about 20° C., about 30° C., about 40° C., about 50° C., about 60° C., or about 80° C. to about 165° C., about 150° C., about 125° C., about 100° C., or to about 80° C. Any of the temperatures described in the Examples may be considered independent embodiments. Typical operating reaction times may range from about 2 hours, from about 4 hours, from about 6 hours, or from about 10 hours to about 28 days, to about 14 days, to about 7 days, to about 4 days, to about 3 days, to about 48 hours, to about 24 hours, to about 12 hours, or to about 6 hours.

As described elsewhere herein, those features described as relevant for the chemical systems for silylating aromatic compounds and aromatic moieties are also relevant for the methods of silylating these aromatic compounds and aromatic moieties. For example, in various embodiments, the methods provide that the system is substantially free of water, oxygen, or both water and oxygen, where these terms are described elsewhere herein.

In related embodiments, at least one organosilane comprises an organosilane of Formula (I) or Formula (II):

where m is 1, 2, or 3 (preferably 1);

n is 10 to 100; and each R is independently optionally substituted $C_{1-12}$ alkyl or heteroalkyl, optionally substituted $C_{5-20}$ aryl or heteroaryl, optionally substituted $C_{6-30}$ alkaryl or heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or heteroaryl, optionally substituted —O—$C_{6-30}$ alkaryl or heteroalkaryl, or optionally substituted —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

In still other embodiments, the organosilane is $(R)_3SiH$, where R is independently $C_{1-6}$ alkyl, preferably $Et_3SiH$ or $Et_2MeSiH$. The at least one strong base may comprise an alkali or alkaline earth metal hydride, as described above, for example, potassium hydride. The at least one strong base may comprise an alkali or alkaline earth metal alkoxide, as described above, for example, where the at least one alkoxide comprises a $C_{1-12}$ linear or branched alkyl moiety or a $C_{5-10}$ aryl or heteroaryl moiety, preferably methoxide, ethoxide, propoxide, butoxide, or 2-ethyl-hexyl alkoxide. The alkali metal cation is preferably potassium or cesium. In most preferred embodiments, the organosilane is triethylsilane, trimethyl silane, diethylmethylsilane, diethylsilane, dimethylsilane, dimethylethylsilane, ethyldimethylsilane, dimethylphenylsilane, diethylphenylsilane and the strong base is potassium tert-butoxide. Other combinations or exemplified reactants provide additional embodiments in this regard.

In certain embodiments, the organosilane (or monomer equivalent) and the at least one strong base are present together at a molar ratio, with respect to one another, in a range of from about 20:1 to about 1:1. In certain embodiments the at least one strong base and organic substrate are present together at a molar ratio, with respect to one another, in a range of from about 0.01:1 to about 5:1 But preferably the base is sub-stoichiometric—i.e., in a ratio of 0.01:1 to 0.9:1—with respect to the organic substrate. That is, the methods may be considered to be catalytic with respect to the strong base.

Additionally, in the context of the silylation methods, the term "substantially free of a transition-metal compound" carries the same connotations and related embodiments as described supra for the chemical system; i.e., reflecting that the methods are effectively conducted in the absence of any deliberately added transition-metal catalyst(s). Unless otherwise stated, when describing a method or system, the term is defined to reflect that the total level of transition metal, as measured by ICP-MS as described in Example 2 below, is less than about 50 ppm. Additional embodiments also provide that the concentration of transition metals is less than about 100 ppm, 50 ppm, 30 ppm, 25 ppm, 20 ppm, 15 ppm, 10 ppm, or 5 ppm to about 1 ppm or 0 ppm, relative to the weight of the total system (i.e., both respect to the silylation system and the silylation system and the organic substrate). As used herein, the term "transition metal" is defined to mean Co, Rh, Ir, Fe, Ru, Os, Ni, Pd, Pt, Cu, or combinations thereof. In further independent embodiments, the concentration of Ni, as measured by ICP-MS, is less than 25 ppm, less than 10 ppm, less than 5 ppm, or less than 1 ppm. Noting here that certain embodiments of the chemical system may comprise the at least one organosilane, and strong base, it should be appreciated that independent embodiments provide that the levels of transition metals are maintained below the levels just described, when considering each of these mixture combinations.

Further embodiments provide that the methods further comprise using sub-stoichiometric amounts (relative to the substrate) of N-based compounds including (preferably N-based chelants), for example, optionally substituted tetraalkylethylenediamine (e.g., tetramethylethylenediamine), optionally substituted 1,7-phenanthroline derivatives, optionally substituted 1,10-phenanthroline derivatives, optionally substituted 2,2'-bipyridine derivatives, and optionally substituted 4-dimethylaminopyridine derivatives.

The methods are fairly flexible with respect to substrates, and accommodate both those containing both aryl and heteroaryl moieties. Exemplary substrates comprising aryl moieties include those comprising optionally substituted benzene (including mesitylene and toluene), biphenyl, naphthalene, anthracene, or higher polyaromatic ring structures. These pure hydrocarbon substrates generally require more forcing conditions to silylate the ring carbons than do heteroaryl systems. See Example 6.1. Nevertheless, the ability to functionalize these hydrocarbon ring structures is an important feature of these methods and systems.

Where the aryl or heteroaryl moiety comprises an alpha-methyl or methylene C—H bond, as in an optionally substituted $C_{1-6}$ alkyl group (as exemplified by methyl groups of toluene, mesitylene, 1,2 dimethylindole, or 2,5-dimethylthiophene in the Examples), it appears that the reaction proceeds to form alpha silanes at temperatures lowered than required to silylate the ring carbons. As used herein, the term "alpha carbon" refers to the first carbon positioned exocyclic to the aromatic moiety, and "alpha" as in "alpha methyl or methylene" is intended to refer to the methyl or methylene on the first exocyckic carbon directly attached to the aromatic ring. The term "alpha silane" refers a silane bonded to the alpha carbon. The term "alpha" is considered to encompass benzylic carbons for 6 membered aryl aromatics. Methods resulting in such silylations are within the scope of the present disclosure.

Other exocyclic ring substituents, including those having an exocyclic aromatic C—X bond, generally react according to the methods described herein. The term "exocyclic" refers to the position of the O, N, or S with respect to the aromatic ring system. For example, the term "exocyclic" refers to a bond in which the carbon is contained within the aromatic rings system, but the respective oxygen, nitrogen, or sulfur atoms are not and, (in the case of nitrogen), vice versa. For example, phenol, dimethylaniline, 1-methyl-1H-pyrrole, and benzenethiol contain exocyclic aromatic C—O, C—N, and C—S bonds, respectively. Exemplary organic substrates comprise, but are not limited to, optionally substituted phenyl ethers, phenyl amines, phenyl sulfides, naphthyl ethers, naphthyl amines, or naphthyl sulfides moiety, N-alkyl or N-aryl pyrroles, or combinations thereof.

Where X is O or N, the reaction favors silylation of the ring ortho or at the carbon adjacent to the carbon containing the exocyclic C—X bond. Electron-rich systems or electron-donating groups or substituents appear to be generally more reactive than electron-poor systems or electron-withdrawing groups or substituents; the latter may require more forcing conditions than the former, but note that more forcing conditions derived from higher temperatures may result in driving the C—X cleavage manifold. Anisole and 2-methoxynaphthalene show a particular preference to the ortho position, and this selectivity provides the basis for embodiments comprising the selective ortho silylation of such substrates. See, e.g., Examples 6.2.1 and 6.2.2. Interesting, and by contrast, those substrates having an exocyclic aromatic C—X bond, where X is S-alkyl provides a different reactivity, showing a proclivity to silylate the alkyl group rather than the aromatic ring system. See, e.g., Example 6.2.4. This reactivity pattern provides a basis for those embodiments comprising the β-silylation of such substrates.

In certain embodiments, the methods are applied to an organic substrate comprising a heteroaryl moiety. Non-limiting heteroaryl moieties include those comprising an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, dibenzothiophene. In more preferred embodiments, the substrate comprises a moiety comprising an optionally substituted furan, pyrrole, thiophene, pyrazole, imidazole, benzofuran, benzopyrrole, benzothiophene, indole, azaindole dibenzofuran, xanthene, dibenzopyrrole, or dibenzothiophene moiety. Independent embodiments provide that the methods yield silylated products substituted as described herein.

In other specific embodiments, the methods are operable on substrates comprising the following moieties:

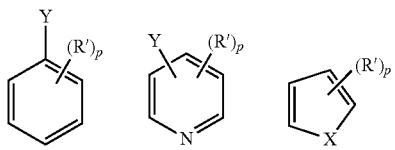

where X is N—R", O, or S;
Y is H, N(R")$_2$, O—R", or S—R"
p is 0 to 4, 0 to 3, 0 to 2, or 0 to 1;
R' is a functional group "Fn," as described above, or (R')$_p$ is a fused alicyclic, heteroalicyclic, aryl or heteroaryl moiety; and
R" is an amine protecting group or an optionally substituted alkyl, aryl, heteroaryl, alkaryl or alk-heteroaryl, preferably optionally substituted C$_1$-C$_6$ alkyl, phenyl, tolyl, benzyl, or phenethyl.

In certain more specific embodiments, the methods are operable on organic substrates comprising the following moieties:

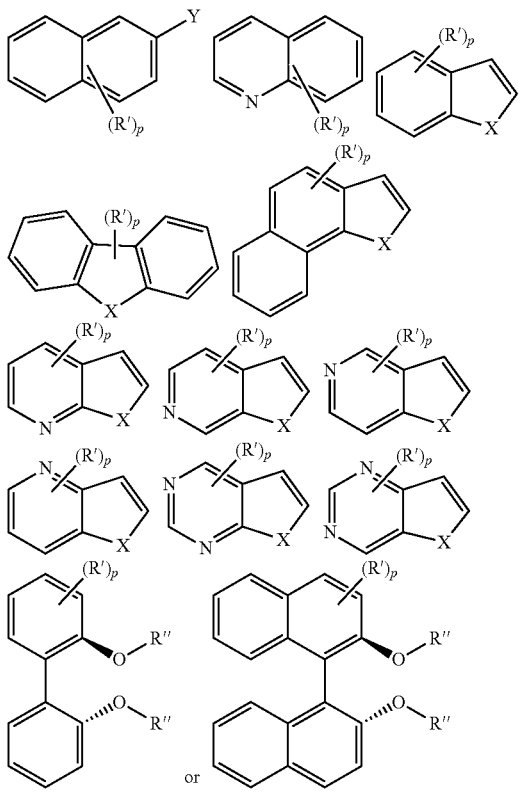

where X, Y, R', R" and p are as defined above. Note that the designation

in each case, is intended to allow for substitution on either aromatic ring.

Heteroaryl moieties appear to react according to the inventive methods under conditions that are milder than their aryl cogeners, such that, in mixed aryl-heteroaryl systems, reactions generally proceed to silylate the heteroaryl ring preferentially. For example, as shown in Examples 6.3.1 to 6.4.7 and 6.4.11 to 6.3.13, silylation is shown to occur preferentially in the heterocylic portion of the molecule. However, and as shown in Example 6.3.10, where an aryl moiety is proximately positioned to a (presumed first) silylated heteroaryl, the silylation of that aryl moiety occurs at much milder conditions than those required for the aryl-only system (cf. Examples 6.2.3 and 6.3.10). This ability to form silylated ring structures from heteroaryl precursors, is another useful feature and embodiment of the present disclosures.

Also, 5-membered heteroaryl moieties appear to react according to the inventive methods under conditions that are milder than even 6-membered heteroaryl moieties. For example, as shown in Example 6.3.6, N-methyazalindole is shown to silylate preferentially in the 5-membered heterocylic portion of the molecule. And both rings silylate under conditions much milder than found for pyridine.

The silylation reactions with substrates comprising 5-membered heteroaryl moieities also provide remarkably clean and apparently tunable regioselectivities. Substrates comprising 5-membered heteroaryl rings containing at least N can silylate at the C-2 or C-3 position, depending on time and temperature. While not intending to be bound by the correctness or incorrectness of any particular theory, it appears that silylation at the C-2 position may represent the kinetic result of the reaction, whereas silylation at the C-3 position may be thermodynamically favored. While described in terms of "kinetic" and "thermodynamic" pathways, it is not clear that silylation at a C-3 position necessarily proceeds through a C-2 intermediate. Indeed, experiments using 1,2 dimethyl indole and 2,5-dimethyl thiophene, where the C-2 positions are blocked by methyl groups, reaction proceeded to silylate the alpha-methyl group preferentially, with no evidence for silylation in the C-3 position.

Unless otherwise stated, reference to silylation at a specific position is intended to connote a regioselectivity or regiospecificity of a product at that position of greater than about 80%. But other embodiments provide that the regiospecificity at that position is greater than about 50%, greater than about 75%, greater than about 90%, or greater than about 95%.

The products of the inventive methods are useful in a range of agrichemical, pharmaceutical, and electronics applications, as described infra. They also provide useful intermediates for subsequent syntheses. The use of aromatic silanes, such as those described herein, are useful synthons for the preparation of biaryl/biaromatic compounds, for example, using the Hiyama coupling methods generally recognized in the art. The skilled artisan would be well able to combine the teachings of these Hiyama coupling methods with those presented here, without undue experimentation, to prepare biaryl/biaromatic compounds, and such preparations are considered within the scope of the present disclosure. Also, Ball and colleagues (Ball et al., Science 28 Sep. 2012: Vol. 337 no. 6102 pp. 1644-1648, which is incorporated by reference herein for its teaching of the catalysts, methods, and substrates) have more recently described another method, using gold catalysts, to couple trialkyl silanes, such as those described herein, to form biaryl/ biaromatic compounds. Again, the skilled artisan would be well able to combine the teachings of the Ball coupling, including at least the second aryl compounds taught or suggested in the Ball reference, again without undue experimentation, to prepare biaryl compounds, and such methods and preparations are considered within the scope of the present disclosure. In such embodiments, a silylated product of the present disclosure, whether isolated or generated in situ, is further reacted under conditions (including the presence of a suitable transition metal catalyst) sufficient to couple the silylated product with a second aromatic compound to prepare the biaryl product. As intended herein, the second aromatic compound comprises an optionally substituted aromatic moiety, including optionally substituted aryl and heteroarly moieties, where the terms "optionally substituted," "aromatic," "aryl," and "heteroaryl" carry the same definitions as already described herein.

The conversion of aromatic silanes, such as those described herein, are also known to be convertible to aromatic hydroxy compounds, using the well-known Fleming-Tamao oxidation methods. The skilled artisan would be well able to combine the teachings of these Fleming-Tamao oxidations with those presented here, again without undue experimentation, to prepare hydroxylated aromatic compounds, and such methods and preparations are considered within the scope of the present disclosure. In such embodiments, the aromatic silylated products of the present disclosure, whether isolated or generated in situ, are further reacted under conditions (including the presence of a suitable transition metal catalyst) sufficient to convert the silylated product to hydroxylated aromatic products.

Also, the ability of the present disclosure to silylate alpha-carbon substituents (or -silyl groups in the case of exocyclic sulfur) also provides that those products may be used as synthons for the Peterson olefination reaction. The known ease of deprotonating the alpha-methylene proton, when adjacent to the silane silicon (the "alpha silicon effect") to yield an alpha-silyl carbanion can form a convenient precursor for this olefination reaction. The skilled artisan would be well able to combine the teachings of these Peterson olefination reaction with those presented here, again without undue experimentation, to replace the alpha silyl groups with alpha olefins, and such methods and preparations are considered within the scope of the present disclosure. In such embodiments, the aromatic silylated products of the present disclosure, whether isolated or generated in situ, are further reacted under conditions sufficient (including the presence of a suitable transition metal catalyst) to convert the silylated product to aromatic alpha-olefin products.

The following listing of embodiments in intended to complement, rather than displace or supersede, the previous descriptions.

Embodiment 1. A chemical system for reducing C—O, C—N, and C—S bonds, said system comprising a mixture of (a) at least one organosilane and (b) at least one strong base, said system preferably being substantially free of a transition-metal compound, and said system optionally comprising at least one molecular hydrogen donor compound, molecular hydrogen, or both.

Embodiment 2. The system of Embodiment 1, further comprising at least one molecular hydrogen donor compound, hydrogen, or both.

Embodiment 3. The system of Embodiment 1 or 2, that is capable of reductively cleaving C—O, C—N, or C—S bonds.

Embodiment 4. The system of any one of Embodiments 1 to 3, that is capable of reductively cleaving aromatic C—O, C—N, or C—S bonds.

Embodiment 5. The system of Embodiment 4, wherein the C—O, C—N, or C—S bonds are exocyclic to an aromatic ring moiety.

Embodiment 6. The system of Embodiment 4, wherein the C—O, C—N, or C—S bonds are endocyclic to an aromatic ring moiety.

Embodiment 7. The system of any one of Embodiments 1 to 3, that is capable of reductively cleaving aliphatic C—O, C—N, or C—S bonds.

Embodiment 8. The system of any one of Embodiments 1 to 7, that is substantially free of water, oxygen, or both water and oxygen.

Embodiment 9. The system of any one of Embodiments 1 to 8, wherein at least one organosilane comprises an organosilane of Formula (I) or Formula (II):

$$(R)_{4-m}Si(H)_m \quad (I)$$

$$R-[SiH(R)-O-]_n-R \quad (II)$$

where: m is 1, 2, or 3; n is 10 to 100; and R is independently optionally substituted $C_{1-12}$ alkyl or heteroalkyl, $C_{5-20}$ aryl or heteroaryl, $C_{6-30}$ alkaryl or heteroalkaryl, $C_{6-30}$ aralkyl or heteroaralkyl, —O—$C_{1-12}$ alkyl or heteroalkyl, —O—$C_{5-20}$ aryl or heteroaryl, —O—$C_{6-30}$ alkaryl or heteroalkaryl, —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Embodiment 10. The system of Embodiment 9, wherein the organosilane is $(R)_3SiH$, where R is $C_{1-6}$ alkyl.

Embodiment 11. The system of any one of Embodiments 1 to 10, wherein the at least one strong base comprises an alkali or alkaline metal hydride or alkoxide.

Embodiment 12. The system of any one of Embodiments 1 to 11, wherein the at least one strong base comprises an alkali or alkaline metal hydride.

Embodiment 13. The system of Embodiment 12, wherein the at least one strong base comprises potassium hydride.

Embodiment 14. The system of any one of Embodiments 1 to 11, wherein the at least one strong base comprises an alkali or alkaline metal alkoxide.

Embodiment 15. The system of Embodiment 14, wherein the at least one alkoxide comprises a $C_{1-12}$ linear or branched alkyl moiety or a $C_{5-10}$ aromatic or heteroaromatic moiety.

Embodiment 16. The system of Embodiment 15, wherein the at least one alkoxide comprises methoxide, ethoxide, propoxide, butoxide, or 2-ethyl-hexyl alkoxide.

Embodiment 17. The system of any one of Embodiments 11 to 16, wherein the alkali or alkaline metal hydride or alkoxide base is a potassium or cesium alkoxide.

Embodiment 18. The system of any one of Embodiments 1 to 17, where the organosilane is triethylsilane and the strong base is potassium t-butoxide.

Embodiment 19. The system of any one of Embodiments 1 to 18, wherein the organosilane and the at least one strong base are present together at a molar ratio, with respect to one another, in a range of from about 20:1 to about 1:2.

Embodiment 20. The system of any one of Embodiments 1 to 19, further comprising an organic compound, said compound being a solvent, a substrate, or both a solvent and a substrate.

Embodiment 21. The system of Embodiment 20, wherein the organic compound is an organic solvent having a boiling point at one atmosphere pressure in a range of from about 25° C. to about 450° C.

Embodiment 22. The system of Embodiment 20 or 21, wherein the organic compound is an organic substrate containing oxygen, nitrogen, sulfur, or a combination thereof.

Embodiment 23. The system of Embodiment 22, wherein the organic substrate is contained within a biomass (e.g. lignin, sugar), biomass liquifaction, biopyrolysis oil, black liquor, coal, coal liquifaction, natural gas, or petroleum process stream.

Embodiment 24. The system of any one of Embodiments 1 to 23, wherein the transition-metal compound is present at less than 10 ppm, relative to the weight of the total system.

Embodiment 25. The system of any one of Embodiments 1 to 24, wherein the hydrogen donor compound comprises 1,3-cyclohexadiene, 1,4-cyclohexadiene, 1,2-cyclohexadiene, 1,4-cyclohexadiene 1,2-dihydronaphthalene, 1,4-dihydronaphthalene, 1,2-dihydroquinoline, 3,4-dihydroquinoline, 9,10-dihydroanthracene, or tetralin.

Embodiment 26. A method of reducing C—X bonds in a an organic substrate, where X is O, N, or S, said method comprising contacting a quantity of the substrate comprising at least one C—O, C—N, or C—S bond with a chemical system comprising a mixture of (a) at least one organosilane and (b) at least one strong base, under conditions sufficient to reduce the C—X bonds of at least a portion of the quantity of the substrate; wherein said chemical system is preferably substantially free of a transition-metal compound, and said chemical system optionally comprising at least one molecular hydrogen donor compound, molecular hydrogen, or both.

Embodiment 27. The method of Embodiment 26, further comprising at least one molecular hydrogen donor compound, hydrogen, or both.

Embodiment 28. The method of Embodiment 26 or 27, wherein the organic substrate comprises at least one C—O bond, and optionally at least one C—N bond, C—S bond, or both C—N and C—S bonds.

Embodiment 29. The method of Embodiment 26 or 27, wherein the organic substrate comprises at least one C—N bond, and optionally at least one C—O bond, C—S bond, or both C—O and C—S bonds.

Embodiment 30. The method of Embodiment 26 or 27, wherein the organic substrate comprises at least one C—S bond, and optionally at least one C—O bond, C—N bond, or both C—O and C—N bonds.

Embodiment 31. The method of anyone of Embodiments 26 to 30, further comprising at least one molecular hydrogen donor compound, molecular hydrogen itself, or both.

Embodiment 32. The method of any one of Embodiments 26 to 31, wherein at least one of the C—O, C—N, or C—S bonds is an aromatic C—O, C—N, or C—S bond.

Embodiment 33. The method of Embodiment 32, wherein at least one of the C—O, C—N, or C—S bonds is exocyclic to an aromatic ring moiety.

Embodiment 34. The method of any one of Embodiments 33, wherein at least one of the C—O, C—N, or C—S bonds is endocyclic to an aromatic ring moiety.

Embodiment 35. The method of any one of Embodiments 26 to 34, wherein the substrate comprises an optionally substituted phenyl ether, phenyl amine, phenyl sulfide, naphthyl ether, naphthyl amine, or naphthyl sulfide moiety, or combination thereof.

Embodiment 36. The method of any one of Embodiments 26 to 35, wherein the substrate comprises a furan, pyrrole, thiophene, benzofuran, benzopyrrole, benzothiophene, 2,3-dihydrobenzofuran, 2,3-dihydrobenzopyrrole, 2,3-dihydrobenzothiophene, dibenzofuran, xanthene, dibenzopyrol, dibenzothiophene, or hindered dibenzofuran, dibenzopyrrole, or dibenzothiophene moiety.

Embodiment 37. The method of any one of Embodiments 26 to 32 wherein at least one of the C—O, C—N, or C—S bonds is an aliphatic C—O, C—N, or C—S bond.

Embodiment 38. The method of any one of Embodiments 26 to 37, that is substantially free of water, oxygen, or both water and oxygen.

Embodiment 39. The method of any one of Embodiments 26 to 38, wherein at least one organosilane comprises an organosilane of Formula (I) or Formula (II):

$$(R)_{4-m}Si(H)_m \quad (I)$$

$$R-[SiH(R)-O-]_n-R \quad (II)$$

where m is 1, 2, or 3; n is 10 to 100; and R is independently optionally substituted $C_{1-12}$ alkyl or heteroalkyl, $C_{5-20}$ aryl or heteroaryl, $C_{6-30}$ alkaryl or heteroalkaryl, $C_{6-30}$ aralkyl or heteroaralkyl, —O—$C_{1-12}$ alkyl or heteroalkyl, —O—$C_{5-20}$ aryl or heteroaryl, —O—$C_{6-30}$ alkaryl or heteroalkaryl, —O—$C_{6-30}$ aralkyl or heteroaralkyl, and, if substituted the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Embodiment 40. The method of Embodiment 39, wherein the organosilane is $(R)_3SiH$, where R is $C_{1-6}$ alkyl.

Embodiment 41. The method of any one of Embodiments 26 to 40, wherein the at least one strong base comprises an alkali or alkaline metal hydride or alkoxide.

Embodiment 42. The method of any one of Embodiments 26 to 41, wherein the at least one strong base comprises an alkali or alkaline metal hydride.

Embodiment 43. The method of Embodiment 42, wherein the at least one strong base comprises potassium hydride.

Embodiment 44. The method of any one of Embodiments 26 to 43, wherein the at least one strong base comprises an alkali or alkaline metal alkoxide.

Embodiment 45. The method of Embodiment 44, wherein the at least one alkoxide comprises a $C_{1-12}$ linear or branched alkyl moiety or a $C_{5-10}$ aromatic or heteroaromatic moiety.

Embodiment 46. The method of Embodiment 45, wherein the at least one alkoxide comprises methoxide, ethoxide, propoxide, butoxide, or 2-ethyl-hexyl alkoxide.

Embodiment 47. The method of any one of Embodiments 39 to 46, wherein the alkali or alkaline metal hydride or alkoxide base is a potassium or cesium alkoxide.

Embodiment 48. The method of any one of Embodiments 26 to 47, where the organosilane is triethylsilane and the strong base is potassium t-butoxide.

Embodiment 49. The method of any one of Embodiments 26 to 48, wherein the organosilane and the at least one strong base are present together at a molar ratio, with respect to one another, in a range of from about 20:1 to about 1:2.

Embodiment 50. The method of any one of Embodiments 26 to 49, wherein the organosilane and C—X bonds in the substrate are present in a ratio of from about 1:2 to about 10:1.

Embodiment 51. The method of anyone of Embodiments 26 to 50, wherein the strong base and C—X bonds in the substrate are present in a range of from about 1:2 to about 10:1.

Embodiment 52. The method of anyone of Embodiments 26 to 49, wherein the organosilane is present in sufficient quantity to act as a solvent for the method.

Embodiment 53. The method of anyone of Embodiments 26 to 51, further comprising an organic solvent.

Embodiment 54. The method of Embodiment 53, said organic solvent having a boiling point at one atmosphere pressure in a range of from about 25° C. to about 450° C.

Embodiment 55. The method of any one of Embodiments 26 to 54, said method comprising heating the organic substrate and chemical system to a temperature in a range of from about 25° C. to about 450° C.

Embodiment 56. The method of any one of Embodiments 26 to 55, wherein the transition-metal compound is present at less than 10 ppm, relative to the weight of the total system.

Embodiment 57. The method of any one of Embodiments 26 to 56, wherein the hydrogen donor compound comprises 1,3-cyclohexadiene, 1,4-cyclohexadiene, 1,2-cyclohexadiene, 1,4-cyclohexadiene 1,2-dihydronaphthalene, 1,4-dihydronaphthalene, 1,2-dihydroquinoline, 3,4-dihydroquinoline, 9,10-dihydroanthracene, or tetralin.

Embodiment 58. The method of any one of Embodiments 26 to 57, wherein the organic substrate is contained within a biomass (e.g. lignin, sugar), biomass liquifaction, biopyrolysis oil, black liquor, coal, coal liquifaction, natural gas, or petroleum process stream.

Embodiment 59. The method of any one of Embodiments 26 to 58, wherein said method is conducted within a biomass (e.g. lignin, sugar), biomass liquifaction, biopyrolysis oil, black liquor, coal, coal liquifaction, natural gas, or petroleum process stream.

Embodiment 60. The method of any one of Embodiments 26 to 59, wherein the method produces a product in which at least one of the C—X bonds are reduced in an amount ranging from about 40% to 100%, relative to the amount originally present in the substrate compound.

Embodiment 61. A chemical system for silylating an organic substrate comprising an aromatic moiety, said system comprising a mixture of (a) at least one organosilane and (b) at least one strong base, said system preferably being substantially free of transition-metal compounds.

Embodiment 62. The system of Embodiment 61, wherein the transition-metal compound is present at less than 10 ppm, relative to the weight of the total system.

Embodiment 63. The chemical system of Embodiment 61 or 62, further comprising an optionally substituted tetraalkylethylenediamine (e.g., tetramethylethylenediamine), an optionally substituted 1,7-phenanthroline derivative, an optionally substituted 1,10-phenanthroline derivative, an optionally substituted 2,2'-bipyridine derivatives, or an optionally substituted 4-dimethylaminopyridine derivative.

Embodiment 64. The system of any one of Embodiments 61 to 63, that is substantially free of water, oxygen, or both water and oxygen.

Embodiment 65. The system of any one of Embodiments 61 to 64, wherein at least one organosilane comprises an organosilane of Formula (I) or Formula (II):

$$(R)_{4-m}Si(H)_m \quad (I)$$

$$R\text{—}[SiH(R)\text{—}O\text{—}]_n\text{—}R \quad (II)$$

where: m is 1, 2, or 3; n is 10 to 100; and each R is independently optionally substituted $C_{1-12}$ alkyl or heteroalkyl, optionally substituted $C_5$-20 aryl or heteroaryl, optionally substituted $C_{6-30}$ alkaryl or heteroalkaryl, optionally substituted $C_{6-30}$ aralkyl or heteroaralkyl, optionally substituted —O—$C_{1-12}$ alkyl or heteroalkyl, optionally substituted —O—$C_{5-20}$ aryl or heteroaryl, optionally substituted —O—$C_{6-30}$ alkaryl or heteroalkaryl, or optionally substituted —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Embodiment 66. The system of Embodiment 65, wherein the organosilane is $(R)_3SiH$, where R is $C_{1-6}$ alkyl.

Embodiment 67. The system of any one of Embodiments 61 to 66, wherein the at least one strong base comprises an alkali or alkaline earth metal hydride or alkoxide.

Embodiment 68. The system of any one of Embodiments 61 to 67, wherein the at least one strong base comprises an alkali or alkaline earth metal hydride.

Embodiment 69. The system of Embodiment 68, wherein the at least one strong base comprises potassium hydride.

Embodiment 70. The system of any one of Embodiments 61 to 67, wherein the at least one strong base comprises an alkali or alkaline earth metal alkoxide.

Embodiment 71. The system of Embodiment 70, wherein the at least one alkoxide comprises a $C_{1-12}$ linear or branched alkyl moiety or a $C_{5-10}$ aromatic or heteroaromatic moiety.

Embodiment 72. The system of Embodiment 71, wherein the at least one alkoxide comprises methoxide, ethoxide, propoxide, butoxide, or 2-ethyl-hexyl alkoxide.

Embodiment 73. The system of any one of Embodiments 67 to 72, wherein the alkali or alkaline earth metal hydride or alkoxide base is a potassium or cesium alkoxide.

Embodiment 74. The system of any one of Embodiments 61 to 73, where the organosilane is triethylsilane and the strong base is potassium tert-butoxide.

Embodiment 75. The system of any one of Embodiments 61 to 74, wherein the organosilane and the at least one strong base are present together at a molar ratio, with respect to one another, in a range of from about 20:1 to about 1:1.

Embodiment 76. The system of any one of Embodiments 61 to 75, further comprising an organic aromatic compound, said compound being a solvent, a substrate, or both a solvent and a substrate.

Embodiment 77. The system of Embodiment 76, wherein the organic compound comprises an optionally substituted benzene, biphenyl, naphthalene, or anthracene ring structure.

Embodiment 78. The system of Embodiment 76 or 77, wherein the organic aromatic compound comprises a heteroaryl moiety.

Embodiment 79. The system of Embodiment 78, wherein the organic aromatic compound comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 80. The system of Embodiment 78 or 79, wherein the organic aromatic compound comprises an optionally substituted furan, pyrrole, thiophene, pyrazole, imidazole, benzofuran, benzopyrrole, benzothiophene, indole, azaindole, dibenzofuran, xanthene, dibenzopyrrole, dibenzothiophene, or a hindered dibenzofuran, dibenzopyrrole, or dibenzothiophene moiety.

Embodiment 81. The system of any one of Embodiments 76 to 80, wherein the organic aromatic compound comprises at least one of the following moieties:

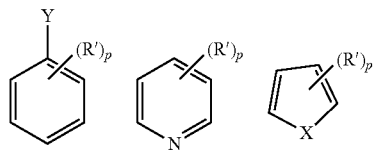

where X is N—R", O, or S;

Y is H, N(R")$_2$, O—R", or S—R"

p is 0 to 4, 0 to 3, 0 to 2, or 0 to 1;

R' is a functional group "Fn," as described above, or (R')$_p$ is an optionally substituted fused alicyclic, heteroalicyclic, aryl or heteroaryl moiety; and R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

Embodiment 82. The system of any one of Embodiments 76 to 81, wherein the substrate comprises at least one of the following moieties:

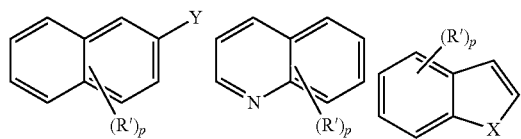

-continued

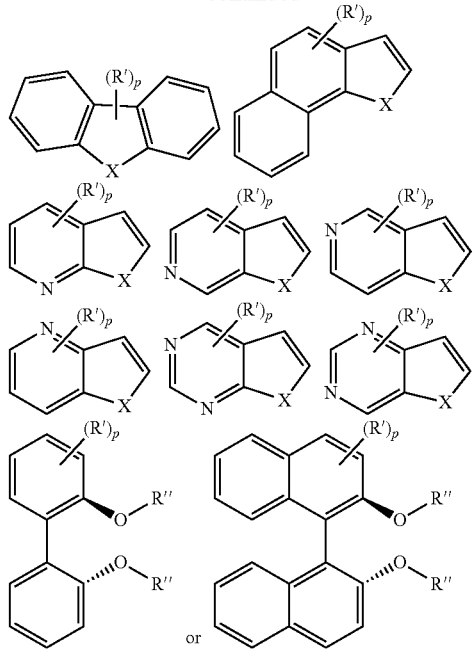

where X, Y, R', R" and p are as defined above. Note that the designation

in each case, is intended to allow for substitution on either aromatic ring.

Embodiment 83. The system of method of any one of Embodiments 76 to 81, wherein the aromatic organic compound comprises at least one alpha-methyl or methylene C—H bond, said method resulting in the formation of an alpha silane.

Embodiment 84. A method of silylating a substrate comprising an aromatic moiety, said method comprising contacting a quantity of the organic substrate with a system of any one of Embodiments 1 to 83.

Embodiment 85. A method comprising contacting an organic substrate comprising an aromatic moiety with a mixture of (a) at least one organosilane and (b) at least one strong base, under conditions sufficient to silylate the substrate; wherein said mixture and substrate are preferably substantially free of transition-metal compounds.

Embodiment 86. The method of Embodiment 85, wherein the transition-metal compound is present at less than 10 ppm, relative to the weight of the total system.

Embodiment 87. The method of Embodiments 85 or 86, wherein the mixture further comprises an optionally substituted tetraalkylethylenediamine (e.g., tetramethylethylenediamine), an optionally substituted 1,7-phenanthroline derivative, an optionally substituted 1,10-phenanthroline derivative, an optionally substituted 2,2'-bipyridine derivatives, or an optionally substituted 4-dimethylaminopyridine derivative.

Embodiment 88. The method of any one of Embodiments 85 to 27, that is substantially free of water, oxygen, or both water and oxygen.

Embodiment 29. The method of any one of Embodiments 85 to 88, wherein at least one organosilane comprises an organosilane of Formula (I) or Formula (II):

$$(R)_{4-m}Si(H)_m \quad (I)$$

$$R-[SiH(R)-O-]_n-R \quad (II)$$

where m is 1, 2, or 3 (preferably 1);
n is 10 to 100; and
and each R is independently optionally substituted $C_{1-12}$ alkyl or heteroalkyl, optionally substituted $C_{5-20}$ aryl or heteroaryl, optionally substituted $C_{6-30}$ alkaryl or heteroalkaryl, optionally substituted $C_{6-30}$ aralkyl or heteroaralkyl, optionally substituted —O— $C_{1-12}$ alkyl or heteroalkyl, optionally substituted —O—$C_{5-20}$ aryl or heteroaryl, optionally substituted —O—$C_{6-30}$ alkaryl or heteroalkaryl, or optionally substituted —O—$C_{6-30}$ aralkyl or heteroaralkyl, and, if substituted, the substituents may be phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group, where the metalloid is Sn or Ge, where the substituents may optionally provide a tether to an insoluble or sparingly soluble support media comprising alumina, silica, or carbon.

Embodiment 90. The method of any one of Embodiments 85 to 89, wherein the organosilane is $(R)_3SiH$, where R is independently $C_{1-6}$ alkyl.

Embodiment 91. The method of any one of Embodiments 25 to 90, wherein the at least one strong base comprises an alkali or alkaline earth metal hydride or alkoxide.

Embodiment 92. The method of any one of Embodiments 85 to 91, wherein the at least one strong base comprises an alkali or alkaline earth metal hydride.

Embodiment 93. The method of Embodiment 32, wherein the at least one strong base comprises potassium hydride.

Embodiment 34. The method of any one of Embodiments 85 to 93, wherein the at least one strong base comprises an alkali or alkaline earth metal alkoxide.

Embodiment 95. The method of Embodiment 94, wherein the at least one alkoxide comprises a $C_{1-12}$ linear or branched alkyl moiety or a $C_{5-10}$ aryl or heteroaryl moiety.

Embodiment 96. The method of Embodiment 95, wherein the at least one alkoxide comprises methoxide, ethoxide, propoxide, butoxide, or 2-ethyl-hexyl alkoxide.

Embodiment 97. The method of any one of Embodiments 91 to 96, wherein the alkali or alkaline earth metal hydride or alkoxide is a potassium or cesium alkoxide.

Embodiment 98. The method of any one of Embodiments 85 to 97, where the organosilane is triethylsilane and the strong base is potassium tert-butoxide.

Embodiment 99. The method of any one of Embodiments 85 to 88, wherein the organosilane and the at least one strong base are present together at a molar ratio, with respect to one another, in a range of from about 20:1 to about 1:1.

Embodiment 100. The method of any one of Embodiments 85 to 99, wherein the at least one strong base and substrate are present together at a molar ratio, with respect to one another, in a range of from about 0.01:1 to about 5:1, preferably in a range of from about 0.01:1 to about 0.9:1.

Embodiment 101. The method of any one of Embodiments 85 to 100, wherein the organic substrate comprises an optionally substituted benzene, biphenyl, naphthalene, or anthracene ring structure.

Embodiment 102. The method of any one of Embodiments 85 to 101, wherein the organic substrate comprises an exocyclic aromatic C—X bond, where X is N, O, or S.

Embodiment 103. The method of any one of Embodiments 85 to 102, wherein the organic substrate comprises an exocyclic aromatic C—X bond and the silylation occurs ortho to the exocyclic C—X bond, where X is N, O, or S.

Embodiment 104. The method of any one of Embodiments 85 to 103, wherein the organic substrate comprises a heteroaryl moiety.

Embodiment 105. The method of any one of Embodiments 85 to 104, wherein the substrate comprises an optionally substituted furan, pyrrole, thiophene, pyrazole, imidazole, triazole, isoxazole, oxazole, thiazole, isothiazole, oxadiazole, pyridine, pyridazine, pyrimidine, pyrazine, triazone, benzofuran, benzopyrrole, benzothiophene, isobenzofuran, isobenzopyrrole, isobenzothiophene, indole, isoindole, indolizine, indazole, azaindole, benzisoxazole, benzoxazole, quinoline, isoquinoline, cinnoline, quinazoline, naphthyridine, 2,3-dihydrobenzofuran, 2,3-dihydrobenzopyrrole, 2,3-dihydrobenzothiophene, dibenzofuran, xanthene, dibenzopyrol, or dibenzothiophene moiety.

Embodiment 106. The method of any one of Embodiments 85 to 105, wherein the substrate comprises an optionally substituted furan, pyrrole, thiophene, pyrazole, imidazole, benzofuran, benzopyrrole, benzothiophene, indole, azaindole, dibenzofuran, xanthene, dibenzopyrrole, or a dibenzothiophene.

Embodiment 107. The method of any one of Embodiments 85 to 106, wherein the organic aromatic substrate comprises at least one of the following moieties:

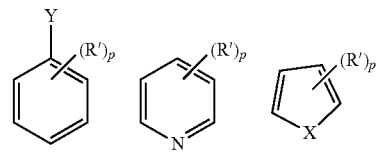

where X is N—R", O, or S;
Y is H, N(R")$_2$, O—R", or S—R"
p is 0 to 4, 0 to 3, 0 to 2, or 0 to 1;
R' is a functional group "Fn," as described above, or (R')$_p$ is an optionally substituted fused alicyclic, heteroalicyclic, aryl or heteroaryl moiety; and
R" is an amine protecting group or an optionally substituted alkyl, aryl, heteroaryl, alkaryl or alk-heteroaryl, preferably optionally substituted $C_1$-$C_6$ alkyl, phenyl, tolyl, benzyl, or phenethyl.

Embodiment 108. The method of any one of Embodiments 85 to 107, wherein the substrate comprises at least one of the following moieties:

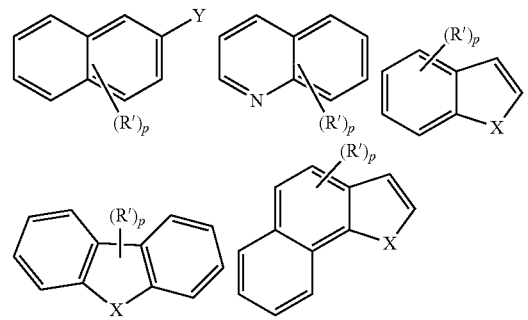

-continued

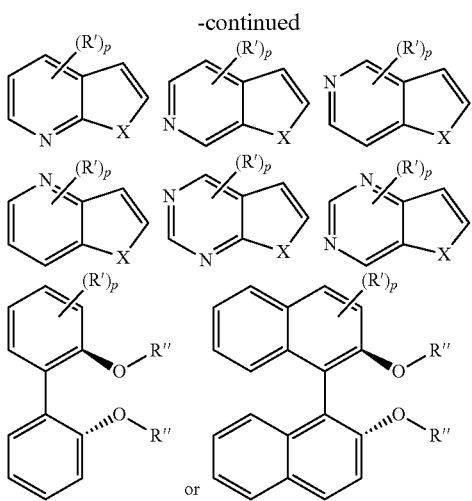

where X, Y, R', R" and p are as defined above. Note that the designation

in each case, is intended to allow for substitution on either aromatic ring.

Embodiment 109. The method of any one of Embodiments 85 to 108, wherein the organic substrate comprises a heteroaryl moiety of structure:

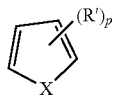

and the silylation occurs at the C-2 position of the heteroaryl ring.

Embodiment 110. The method of anyone of Embodiments 85 to 109, wherein the organic substrate comprises a heteroaryl moiety of structure:

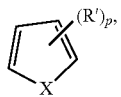

and the silylation occurs at the C-3 position of the heteroaryl ring.

Embodiment 111. The method of any one of Embodiments 85 to 110, wherein the aromatic substrate comprises at least one alpha-methyl or methylene C—H bond, said method resulting in the formation of an alpha silane.

Embodiment 112. The method of any one of Embodiments 25 to 111, wherein the aromatic substrate is polymeric.

Embodiment 113. The method of any one of Embodiments 85 to 112, wherein the aromatic silylated product is further reacted under conditions sufficient to couple the silylated product with a second aromatic compound to prepare a biaryl product.

Embodiment 114. The method of any one of Embodiments 85 to 112, wherein the aromatic silylated product is further reacted under conditions sufficient to convert the silylated product to an aromatic hydroxylated product.

Embodiment 115. The method of any one of Embodiments 85 to 112, wherein the aromatic silylated product is further reacted under conditions sufficient to convert the silylated product to an aromatic alpha-olefin product.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1: General Information

All reactions were carried out in dry glassware under an argon atmosphere using standard Schlenk line techniques or in a Vacuum Atmospheres Glovebox under a nitrogen atmosphere unless specified otherwise. Mesitylene (puriss, ≥99.0% (GC)) was degassed by three freeze-pump-thaw cycles prior to use. All other solvents were purified by passage through solvent purification columns and further degassed with argon. Tetrahydrofuran was purified by passage through a solvent purification column then further distilled over sodium-potassium alloy and degassed with argon. All other solvents were purified by passage through solvent purification columns and further degassed with argon. NMR solvents for air-sensitive experiments were dried over $CaH_2$ and vacuum transferred or distilled into a dry Schlenk flask and subsequently degassed with argon. Triethylsilane (99%) and deuterotriethylsilane (97 atom % D) were purchased from Sigma-Aldrich and degassed by three freeze-pump-thaw cycles prior to use and other commercially available liquid reagents were treated analogously. Di-4-(methyl)phenyl ether, 1-naphthol, 2-naphthol, 4-tert-butylanisole, 4-methylanisole, 1,3-diphenoxybenzene, 2-methoxynaphthalene, and 1.0M tetrabutylammonium fluoride THE solution were purchased from Sigma-Aldrich and used as received. Phenyldimethylsilane (≥98%), ethyldimethylsilane(98%) and diethylsilane (99%) were purchased from Sigma-Aldrich and distilled over $CaH_2$ and degassed by three freeze-pump-thaw cycles prior to use. Other commercially available liquid reagents were treated analogously. 1-methylindole (≥97%), benzofuran (99%), thianaphthene (98%), 1-methoxynaphthalene (≥98%), anisole (99%) and thioanisole (99%) were purchased from Sigma-Aldrich and were distilled prior to use. 2-methoxynaphthalene was recrystallized twice from boiling $Et_2O$. 1-phenylpyrrole (99%) was dissolved in $Et_2O$ and passed through activated alumina. The ether was removed in vacuo and the solid residue was recrystallized twice from a 3:1 mixture of absolute EtOH/water. 1-phenyl pyrrole (99%), diphenyl ether (≥99%), dibenzothiophene (≥99%) were purchased from Sigma-Aldrich and used as received. 4-methoxypyridine (97%) and 2,6-dimethoxypyridine (98%) were purchased from Sigma-Aldrich, passed several times through neutral, activated alumina and subjected to 3 freeze-pump-thaw cycles prior to use. 1-methyl-7-azaindole was prepared following the procedure of Cheve, G. et al., Medchemcomm 2012, 3, 788. Sublimed grade KO-t-Bu (99.99%) was purchased from Sigma-Aldrich and subjected to vacuum sublimation (30 mTorr, 160° C.) prior to use. Di-4-(methyl)phenyl ether, 1-naphthol, 2-naphthol, 4-tert-butylanisole, 4-methylanisole, 1,3-diphenoxybenzene, 2-methoxynaphthalene, and 1.0M tetrabutylammonium fluoride THF solution were purchased from Sigma-Aldrich and used as received. 4-(Methoxy)dibenzofuran, (2) di-4-(tert-butyl)phenyl ether (3), naphthyl ethers (3), 4-(phenyl)phenyl phenyl ether, 2-ethoxynaphthalene, 2-Neopentyloxynaphthalene, 2-tert-butyloxynaphthalene were synthesized according to the literature procedures. Standard NMR spectroscopy experiments were conducted on a Varian Mercury ($^1$H, 300 MHz) spectrometer, a Varian Inova 400 MHz spectrometer, a Varian 500 MHz spectrometer equipped with an AutoX probe, or a Varian 600 MHz spectrometer equipped with a Triax Probe. Chemical shifts are reported in ppm downfield from Me$_4$Si by using the residual solvent peak as an internal standard. Spectra were analyzed and processed using MestReNova Ver. 7. GC-FID analyses were obtained on an Agilent 6890N gas chromatograph equipped with a HP-5 (5%-phenyl)-methylpolysiloxane capillary column (Agilent). GC-MS analyses were obtained on an Agilent 6850 gas chromatograph equipped with a HP-5 (5%-phenyl)-methylpolysiloxane capillary column (Agilent). High-resolution mass spectra (EI and FAB) were acquired by the California Institute of Technology Mass Spectrometry Facility. EPR spectra were recorded on a Bruker EMS spectrometer.

Example 2: ICP-MS Analysis

ICP-MS analysis was conducted using the California Institute of Technology MS facility with 100 mg samples of dibenzofuran, triethylsilane, mesitylene and potassium tert-butoxide, which were added to 50 mL DigiTUBE digestion tubes (SCP Science) followed by addition of 3.0 mL of Plasma Pure nitric acid (SCP Science) to each digestion tube and heating to 75° C. for 36 hours. After digestion, each sample was diluted using Nanopure/Milli Q water to 50 mL and sample analysis performed on an HP 4500 ICPMS spectrometer. Semiquantitative analysis was performed using a 10 ppm solution of lithium, yttrium, cerium and thallium for calibration. Each sample was analyzed twice and the average measurements are given. (Table 1).

TABLE 1

ICP-MS Analysis of Various Metals in Reagents and Reaction Mixture

| | Reagent (unit: ppm) | | | | |
|---------|-------------|--------|---------|------------|-------------------|
| Element | Dibenzofuran | KOt-Bu | Et$_3$SiH | Mesitylene | Reaction Mixture |
| Fe | 0.15 | 4.92 | 0.67 | 0.11 | 5.80 |
| Ru | 0.00 | 0.07 | 0.00 | 0.01 | 3.13 |
| Os | 0.01 | 0.01 | 0.01 | 0.00 | 0.20 |
| Co | 0.00 | 0.01 | 0.00 | 0.00 | 0.26 |
| Rh | 0.00 | 0.00 | 0.00 | 0.00 | 1.07 |
| Ir | 0.00 | 0.01 | 0.00 | 0.09 | 0.40 |
| Ni | 0.12 | 0.06 | 0.06 | 0.38 | 0.79 |
| Pd | 0.00 | 0.04 | 0.00 | 0.01 | 0.88 |
| Pt | 0.00 | 0.07 | 0.00 | 0.01 | 1.74 |
| Cu | 0.03 | 10.42 | 0.04 | 0.09 | 7.59 |

Example 3: General Procedure

In a glovebox, a 4 mL screw cap vial was loaded with the corresponding substrate (0.1 mmol, 1 equiv.), base (0.5-5 equiv.) and a magnetic stirring bar, followed by syringe addition of the solvent (1 mL) and triethylsilane (1-5 equiv.). The reaction vial was sealed with a Teflon-lined screw cap and heated at a given temperature and time inside the glovebox. After cooling to room temperature, dark red to black reaction mixture was diluted with diethyl ether (3 mL) and carefully quenched with 1 ml of 1 N aqueous HCl. Tridecane (internal standard for GC) was added, the organic layer was separated and the aqueous layer was extracted with ether (3 mL) until TLC controls show no UV-active compounds present in the extracts. The combined organic layers were passed through a short pad of Celite and subjected to GC/FID, GC/MS and $^1$H-NMR analyses. Unless stated otherwise, in preparative experiments only products with the overall yield exceeding 2% were isolated and characterized. In the case of naphthyl alkyl ethers, a different workup procedure was used. After cooling, the reaction was diluted with dichloromethane (5 mL) and carefully quenched with 2 mL of 1 N aqueous HCl. Tridecane was added, and the mixture was transferred to a separatory funnel. The organic phase was separated, and the aqueous layer was extracted with dichloromethane (3 mL). The combined organic layers were dried over anhydrous MgSO$_4$ and filtered. For all reactions, the products were identified using GC/MS and GC/FID and NMR by comparison with the authentic samples. Trace soluble side products observed in naphthyl alkyl ether reductions included naphthalene, 1,2,3,4-tetrahydronaphthalene, and 5,6,7,8-tetrahydro-2-naphthol.

Example 4: Synthesis and Characterization of Selected Compounds

Example 4.1: 4-(Triethylsilyl)dibenzofuran (3)

The title compound was prepared by analogy to the protocol for the synthesis of 4-(trimethylsilyl)dibenzofuran by Kelly and co-workers; Bekele, H., et al., J Org. Chem., 1997, 62, 2259. Data for (3): Colorless oil. $^1$H-NMR (500 MHz, CDCl$_3$): δ 7.99-7.96 (m, 2H$_{ar}$), 7.59 (d-like, J=10 Hz, 1H$_{ar}$), 7.54 (dd, J=2, 5 Hz, 1H$_{ar}$), 7.48-7.44 (m, 1H$_{ar}$), 7.37-7.33 (m, 2H$_{ar}$), 1.03 (m, 15H, 3CH$_2$CH$_3$). $^{13}$C-NMR (126 MHz, CDCl$_3$) δ 161.30, 156.05, 133.57, 126.92, 122.52, 122.48, 121.58, 120.68, 111.75, 7.63, 3.59. HRMS: [C$_{18}$H$_{22}$OSi] calculated 282.1440; measured 282.1444.

Example 4.2: 4,6-Bis(triethylsilyl)dibenzofuran (4)

To a solution of dibenzofuran (2.00 g, 11.9 mmol, 1 equiv.) and tetramethylethylenediamine (11.1 mL, 29.7 mmol, 2.5 equiv.) in tetrahydrofuran (50 ml) t-butyllithium (17.5 mL of 1.7 M solution in pentane, 29.8 mmol, 2.5 equiv.) was slowly added at −78° C. under argon. The mixture was allowed to reach ambient temperature and stirring was continued for 4 h prior to addition of chlorotriethylsilane (10.1 mL, 60 mmol, 5 equiv.). The resulting mixture was stirred at ambient temperature for another 16 h. After quenching the reaction with the saturated ammonium chloride solution (40 mL) and extraction with diethyl ether (3×30 mL), the combined organic layers were dried over anhydrous sodium sulfate, filtered and the filtrate concentrated in vacuo. Crude reaction mixture was purified by chromatography on silica (hexanes) and product obtained was recrystallized from a mixture of methanol and isopropanol (1:1) to afford 4,6-bis(triethylsilyl)dibenzofuran (1.28 g, 2.45 mmol, 28%) as colorless needles. Data for (4): Colorless needles. M.p.=59-61° C. $^1$H-NMR (300 MHz, CDCl$_3$) δ 7.97 (dd, J=3, 9 Hz, 2H$_{ar}$), 7.54 (dd, J=3, 9 Hz, 2H$_{ar}$), 7.33 (t, J=9 Hz, 2H$_{ar}$), 1.07-0.95 (m, 30H, 6 CH$_2$CH$_3$). $^{13}$C-NMR (126 MHz, CDCl$_3$) δ 160.90, 133.48, 122.87, 122.34, 121.57, 120.03, 7.66, 3.52. HRMS: [C$_{24}$H$_{36}$OSi$_2$] calculated 396.2305; measured 396.2321.

Example 4.3: 3-(Triethylsilyl)biphenyl-2-ol (5)

The title compound was prepared via cleavage of 3 (vide infra). Data for (5): White solid. M.p.=44-46° C. $^1$H-NMR (300 MHz, CDCl$_3$) δ 7.52-7.40 (m, 5H$_{ar}$), 7.36 (dd, J=3, 9 Hz, 1H$_{ar}$), 7.23 (dd, J=3, 6 Hz, 1H$_{ar}$), 6.98 (t, J=9 Hz, 1H$_{ar}$), 5.41 (s, 1H, OH), 1.02-0.96 (m, 9H, CH$_3$), 0.91-0.83 (m, 6H, CH$_2$). $^{13}$C-NMR (75 MHz, CDCl$_3$) δ 157.25, 137.51, 135.97, 131.30, 129.58, 129.39, 128.01, 127.17, 123.04, 120.40, 7.79, 3.69. HRMS: [C$_{18}$H$_{24}$OSi] calculated 284.1596; measured 284.1583.

Example 4.4: (3'-Triethylsilyl)biphenyl-2-ol (6)

The title compound was prepared via cleavage of 3 (vide infra). Data for (6): Colorless oil. $^1$H-NMR (500 MHz, CDCl$_3$): δ 7.57-7.56 (m, 1H$_{ar}$), 7.54-7.52 (m, 1H$_{ar}$), 7.49-7.44 (m, 2H$_{ar}$), 7.28-7.24 (m, 2H$_{ar}$), 7.02-6.99 (m, 2H$_{ar}$), 5.24 (s, 1H, OH), 0.98 (t, J=10 Hz, 9H, CH$_3$), 0.82 (q, J=15 Hz, 6H, CH$_2$). $^{13}$C NMR (126 MHz, CDCl$_3$): δ 153.44, 139.07, 136.12, 134.71, 133.76, 130.23, 129.36, 129.08, 128.53, 128.44, 120.80, 115.72, 7.43, 3.31. HRMS: [C$_{18}$H$_{24}$OSi] calculated 284.1596; measured 284.1585.

Example 4.5: 3,3'-Bis(triethylsilyl)biphenyl-2-ol (7)

The title compound was prepared according to General Procedure by heating dibenzofuran (1, 840 mg, 5.0 mmol, 1 equiv.) with KOt-Bu (1.12 g, 10 mmol, 2 equiv.) and Et$_3$SiH (4.0 ml, 25 mmol, 5 equiv.) in 20 ml of toluene for 20 hours at 100° C. After acidic aqueous work up, the crude reaction mixture was purified by chromatography on silica using hexanes and hexanes-ether (10:1) to give, among other isolated products, 20 mg (0.05 mmol, 1%) of 7. Data for (7): oily solid $^1$H-NMR (300 MHz, CDCl$_3$): δ 7.53-7.44 (m, 2H$_{ar}$), 7.46-7.44 (m, 2H$_{ar}$), 7.36 (dd, J=1.5, 7.5 Hz, 1H$_{ar}$), 7.23 (dd, J=1.5, 7.5 Hz, 1H$_{ar}$), 6.98 (t, J=7 Hz, 1H$_{ar}$), 5.42 (s, 1H, OH), 1.01-0.96 (m, 18H, 6CH$_3$) 0.91-0.77 (m, 15H, 6CH$_2$). $^{13}$C NMR (75 MHz, CDCl$_3$): δ 157.37, 139.45, 136.61, 135.87, 135.09, 133.86, 131.38, 129.57, 128.71, 127.55, 122.97, 120.36, 7.80, 7.57, 3.69, 3.46. HRMS: [C$_{24}$H$_{38}$OSi$_2$] calculated 398.2461; measured 396.2470.

Example 4.6: o-Triethylsilyldiphenyl Ether o-Triethylsilyldiphenyl ether was prepared using the modified procedure by Fink on a 30 mmol scale based on diphenyl ether. After addition of Et$_3$SiCl, the reaction mixture was stirred at 40° C. for 4 hours followed by aqueous work up and vacuum distillation to obtain the title compound as colorless oil in 88% yield. $^1$H-NMR (500 MHz, CDCl$_3$: δ 7.47 (dd, J=7.0, 1.5 Hz, 1H$_{ar}$), 7.35-7.31 (m, 2H$_{ar}$), 7.30-7.25 (m, 1H$_{ar}$), 7.10-7.06 (m, 1H$_{ar}$), 7.02-6.97 (m, 2H$_{ar}$), 6.79 (d, J=8.0, 1H$_{ar}$), 0.95 (t-like, J=8.5 Hz, 9H), 0.83 (qlike, J=8.0 Hz, 6H). $^{13}$C-NMR (126 MHz, CDCl$_3$): δ 162.33, 157.39, 136.57, 135.08, 129.86, 129.82, 127.76, 123.34, 123.08, 122.86, 119.04, 117.22, 7.71, 3.55. HRMS: [C$_{18}$H$_{24}$SiO] calculated 284.1596, measured 284.1587.

Example 5: Selected Reactions

Example 5.1: Preparative Scale Cleavage of Dibenzofuran and Deuteration Experiments

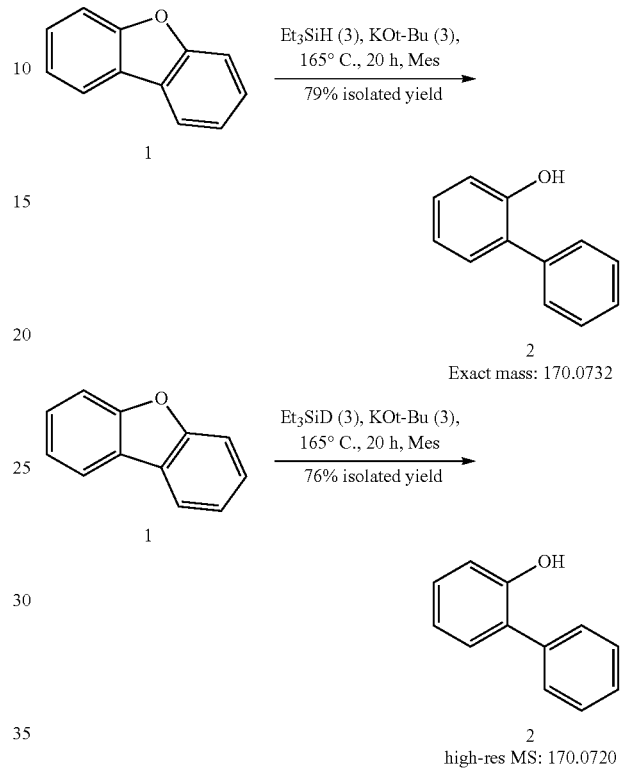

The reaction was conducted according to the General Procedure by heating dibenzofuran (1, 250 mg, 1.49 mmol, 1 equiv.), KOt-Bu (500 mg, 4.46 mmol, 3 equiv.) and Et$_3$SiH (713 microliters, 4.46 mmol, 3 equiv.) in 4.4 mL of mesitylene for 20 hours at 165° C. After dilution with diethyl ether (5 mL), the organic phase was first washed with water (1 mL), and then with 2.5N KOH solution (3×20 mL). The basic aqueous fractions were collected and washed through once with CH$_2$C$_2$ (25 ml) to remove any undesired organics. The resulting basic aqueous fractions were then acidified with concentrated HCl until a pH of 1 and then subsequently extracted with CH$_2$C$_2$ (3×25 mL). The organic fractions were collected and concentrated under reduced pressure to give pale yellow crystals. Purification by chromatography on silica gel with hexanes/ethyl acetate (gradient elution: 0% to 5% ethyl acetate) afforded biphenyl-2-ol (2, 198 mg, 1.16 mmol, 79%) as a colorless solid. $^1$H and $^{13}$C NMR spectral assignments of 1 were consistent with those of the authentic sample.

The identical procedure applied to the reductive cleavage of dibenzofuran but now with Et$_3$SiD gave undeuterated biphenyl-2-ol with 76% isolated yield. HRMS. [C$_{12}$H$_{10}$O] calculated 170.0732; measured 170.0720.

Repeating the aforementioned experiment with Et$_3$SiH and Mes-d$_{12}$ gave deuterated biphenyl-2-ol in 73% isolated yield. HRMS. [C$_{12}$H$_4$D$_6$O] calculated 176.1108; measured 176.1115; FWHM ~4 Da. The identical procedure applied to the reductive cleavage of dibenzofuran but now with Et$_3$SiD and Mesd$_{12}$ gave deuterated biphenyl-2-ol with 79% isolated yield. HRMS: [$C_{12}H_4D_6O$] calculated 176.1108; measured 176.1108; FWHM 4 Da.

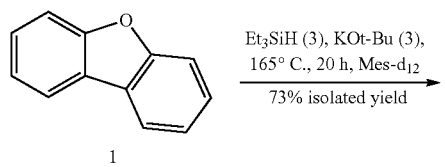

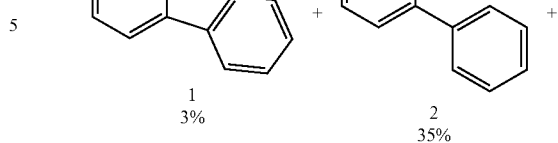

2-D
high-res MS: 176.1115

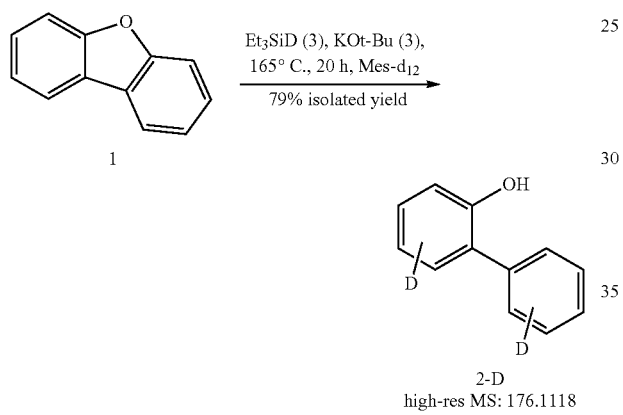

2-D
high-res MS: 176.1118

Very little deuterium incorporation into 2 occurred when dibenzofuran was reacted with Et$_3$SiD in mesitylene at 165° C. In line with this, identical base peaks in high-resolution MS spectra of biphenyl-2-ol prepared either from Et$_3$SiH or Et$_3$SiD in Mes-d$_{12}$ indicated that rapid H/D exchange with the solvent occurred under the reaction conditions. Interestingly, as proton, carbon and HSQC spectra of deuterated 2 suggested, while all of the protons underwent partial H/D exchange, only for the ortho-OH position did this process reach completion.

Example 5.2: Reactions of 4-(Triethylsilyl)dibenzofuran

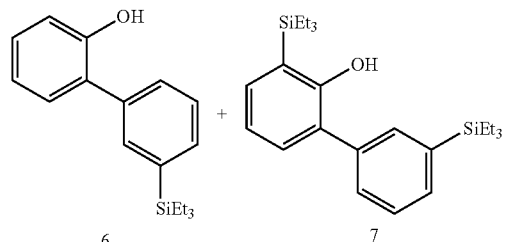

The reaction was conducted according to the General Procedure by heating 4-Et$_3$Si-dibenzofuran (3, 141 mg, 0.5 mmol, 1 equiv.), KOt-Bu (112 mg, 1 mmol, 2 equiv.) and Et$_3$SiH (401 microliters, 2.5 mmol, 5 equiv.) in 2 ml of toluene for 20 hours at 100° C. After acidic aqueous work up, the crude reaction mixture was purified by chromatography on silica using hexanes and hexanes-ether (10:1) to isolate 2-phenylphenol (2, 30 mg, 0.177 mmol, 35%), 2-triethylsilyl-6-phenylphenol (5, 37 mg, 0.134 mmol, 26%), 2-(3-triethylsilylphenyl)phenol (6, 17 mg, 0.063 mmol, 12%). Quantities of unconsumed 3 as well as products 1, 4 and 7 were obtained using post-chromatography GC-FID analysis of the corresponding mixed fractions.

Example 5.3: Investigation of Silylated Dibenzofurans as Intermediates Towards C—O Bond Cleavage: Cleavage Attempts with KOt-Bu

A

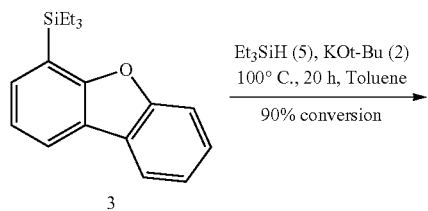

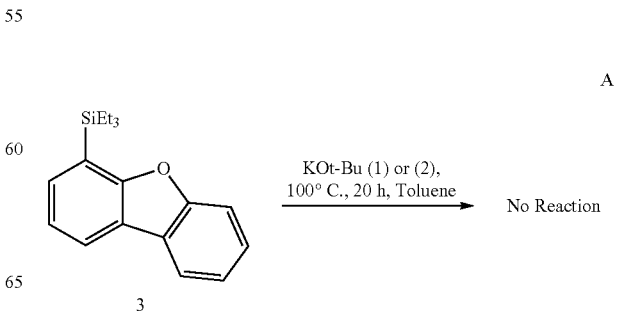

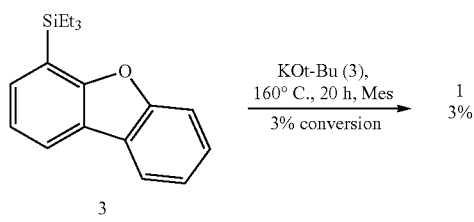
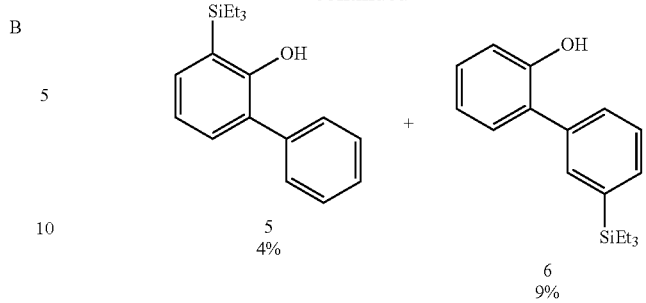

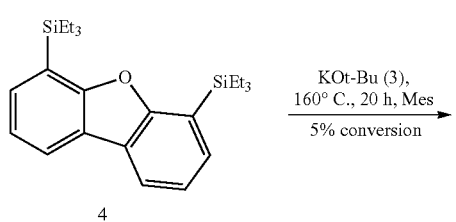

Starting material 3 (14.1 mg, 0.05 mmol, 1 equiv.) was heated with KOt-Bu (5.6 mg or 11.2 mg, 1 or 2 equiv., respectively) in 0.8 ml d-toluene at 100° C. for 20 hours in a J. Young tube under nitrogen. Monitoring the reaction progress by H NMR showed no conversion of 3 in both cases. Likewise, starting materials 3 (28.2 mg, 0.1 mmol, 1 equiv.) or 4 (39.6 mg 0.1 mmol, 1 equiv.) were heated with KOt-Bu (36.6 mg) in 0.3 mL of mesitylene at 160° C. for 20 hours. Subsequent analysis of the crude reaction mixtures by GC-FID or 1H NMR revealed 3% conversion to 1 in case of 3 and 5% conversion to 3 from 4.

Example 5.4: Cleavage of 4,6-Bis(triethylsilyl)dibenzofuran

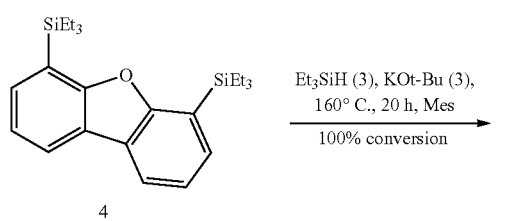

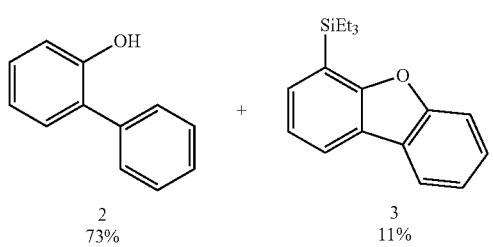

The reaction was conducted according to the General Procedure by heating 2-(3'-triethylsilylphenyl)phenol (4, 39.6 mg, 0.1 mmol, 1 equiv.), KOt-Bu (33.6 mg, 0.3 mmol, 3 equiv.) and Et₃SiH (48 microliters, 0.3 mmol, 3 equiv.) in 0.2 ml of mesitylene for 20 hours at 160° C. After acidic aqueous work up, internal standard was added and the crude reaction mixture was analyzed by GC-FID.

Example 5.5: Reactions of 4-(Methoxy)dibenzofuran at Elevated Temperature

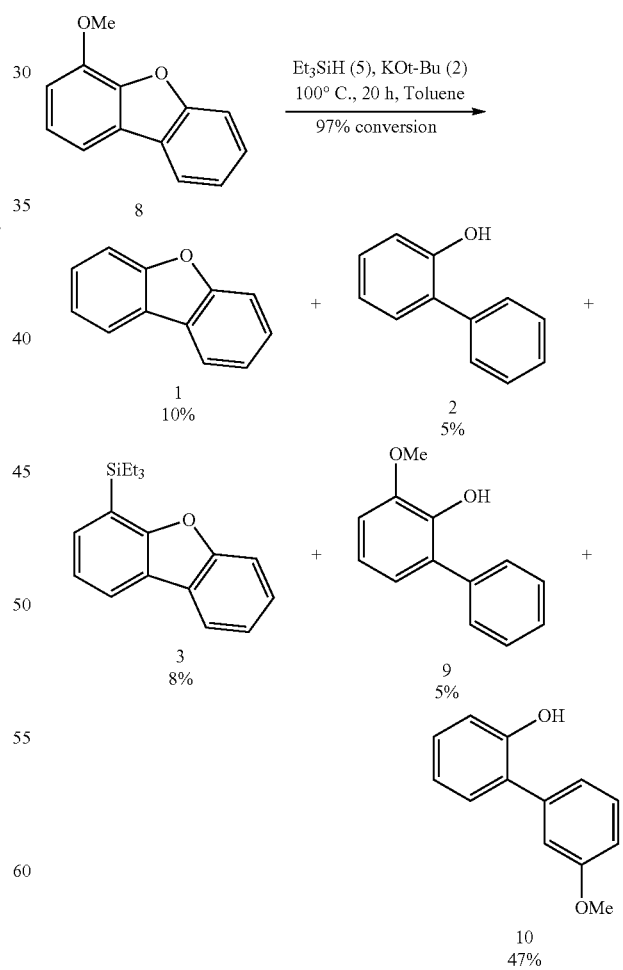

The reaction was conducted according to the General Procedure by heating 4-MeO-dibenzofuran (8, 89 mg, 0.5 mmol, 1 equiv.), KOt-Bu (112 mg, 1 mmol, 2 equiv.) and Et₃SiH (401 microliters, 2.5 mmol, 5 equiv.) in 2 ml of toluene for 20 hours at 100° C. After aqueous work up, the crude reaction mixture was purified by chromatography on silica using hexanes and hexanes-ether to recover unconsumed starting material 8 (3 mg, 0.015 mmol, 3%) and isolate dibenzofuran (1, 8.4 mg, 0.05 mmol, 10%; since fractions of 1 contained small amounts of starting 8, quantification was done by ¹H-NMR with CH₂Br₂ as an internal standard), 1,1'-biphenyl-2-ol (2, 4.3 mg, 0.025 mmol, 5%), 4-Et₃Si-dibenzofuran (3, 11 mg, 0.039 mmol, 8%), 2-methoxy-6-phenyl-phenol (9, mg, 0.025 mmol, 5%), 2-(3'-methoxyphenyl)phenol (10, 47 mg, 0.235 mmol, 47%). Note: only compounds with the yield exceeding 2% were characterized. ¹H and ¹³C NMR spectral assignments of 9 and 10 were consistent with literature reports.

Example 5.6: Synthesis of 4,6-Di(methyl)dibenzofuran

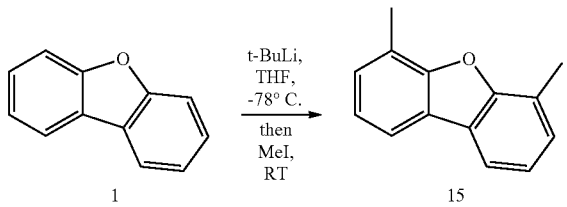

To a solution of dibenzofuran (2.00 g, 11.9 mmol, 1 equiv.) and tetramethylethylenediamine (11.1 mL, 29.7 mmol, 2.5 equiv.) in diethyl ether (50 ml) t-butyllithium (17.5 mL of 1.7 M solution in pentane, 29.8 mmol, 2.5 equiv.) was slowly added at minus 78° C. under argon. The mixture was allowed to reach ambient temperature and stirring was continued for 4 h prior to addition of methyl iodide (3.7 mL, 60 mmol, 5 equiv.). The resulting mixture was stirred at ambient temperature for another 16 h. After quenching the reaction with the saturated ammonium chloride solution (40 mL) and extraction with diethyl ether (3×30 mL), the combined organic layers were dried over anhydrous sodium sulfate, filtered and the filtrate concentrated in vacuo. Crude reaction mixture was purified by chromatography on silica (hexanes) and product obtained was recrystallized from methanol to afford 4,6-dimethyl-dibenzofuran (480 mg, 2.45 mmol, 21%) as a colorless solid. Data for (15): 1H-NMR (300 MHz, CDCl₃): δ 7.75 (dd, J=1.0, 6.0 Hz, 2H$_{ar}$), 7.24-7.20 (m, 4H$_{ar}$), 2.61 (s, 6H, 2CH₃). ¹³C NMR (75 MHz, CDCl₃): δ 155.07, 128.00, 124.17, 122.60, 122.02, 118.2, 15.41. HRMS: [C₁₄H₁₂O] calculated 196.0888; measured 196.0884.

Example 5.7: Cleavage of 4,6-Di(methyl)dibenzofuran

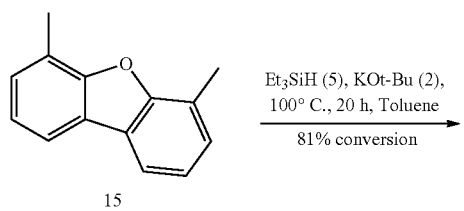

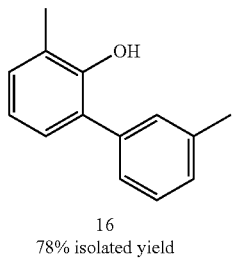

16
78% isolated yield

The reaction was conducted according to the General Procedure by heating 4,6-di(methyl)dibenzofuran (15, 98 mg, 0.5 mmol, 1 equiv.), KOt-Bu (112 mg, 1 mmol, 2 equiv.) and Et₃SiH (401 microliters, 2.5 mmol, 5 equiv.) in 2 ml of toluene for 20 hours at 100° C. After aqueous work up, the crude reaction mixture was purified by chromatography on silica using hexanes-ether 4:1 to obtain 77 mg of product 16 as yellow oil. Data for (16): ¹H-NMR (500 MHz, CDCl₃): δ 7.35 (t, J=7.5 Hz, 1H$_{ar}$), 7.25-7.22 (m, 2H$_{ar}$), 7.20-7.18 (m, 1H$_{ar}$), 7.11 (d-like, J=10 Hz, 1H$_{ar}$), 7.05 (d-like, J=7.5 Hz, 1H$_{ar}$), 6.87 (t, J=7.5 Hz 1H$_{ar}$), 5.31 (s, 1H, OH), 2.39 (s, 3H, CH₃), 2.30 (s, 3H, CH₃). ¹³C-NMR (126 MHz, CDCl₃): δ 150.68, 139.26, 137.36, 130.51, 129.93, 129.39, 128.73, 127.83, 127.76, 126.20, 124.70, 120.25, 21.60, 16.33. HRMS: [C₁₄H₁₄O] calculated 198.1045, measured 198.1046.

Repeating this experiment in mesitylene, at 165° C. for 20 hours resulted in 100% conversion of the starting material 15, with 96% yield of 16.

While comprehensive mechanistic studies are still required before the underlying reaction pathways can be reliably established, having observed no conversion of 3 (4-(Triethylsilyl)dibenzofuran) under basic conditions and smooth reductive cleavage of 4,6-Dimethyldibenzofuran 15 into the Corresponding Biphenyl-2-Ol 16, the Intermediacy of Benzynes, as the presence of ortho-silylated aromatic ethers might have initially suggested, seems unlikely.

Example 5.8: EPR Experiments

Figure 2:
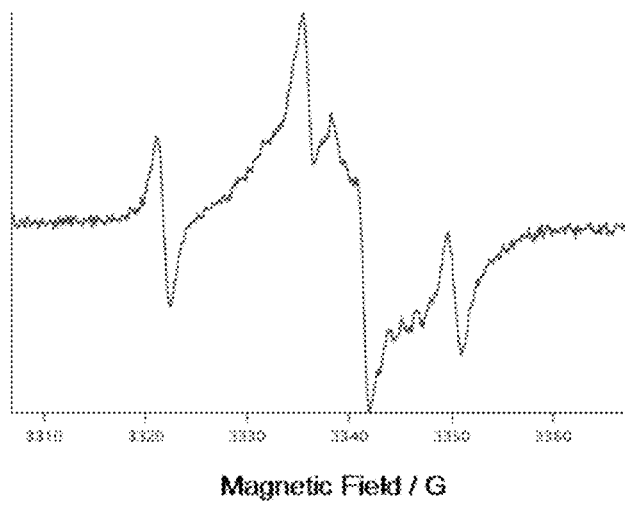
FIG. 2 shows the EPR spectrum of dibenzofuran, Et$_3$SiH and KOt-Bu reaction mixture in toluene, as described in Example 5.8. The same signal is observed without dibenzofuran added.
Figure 3A:
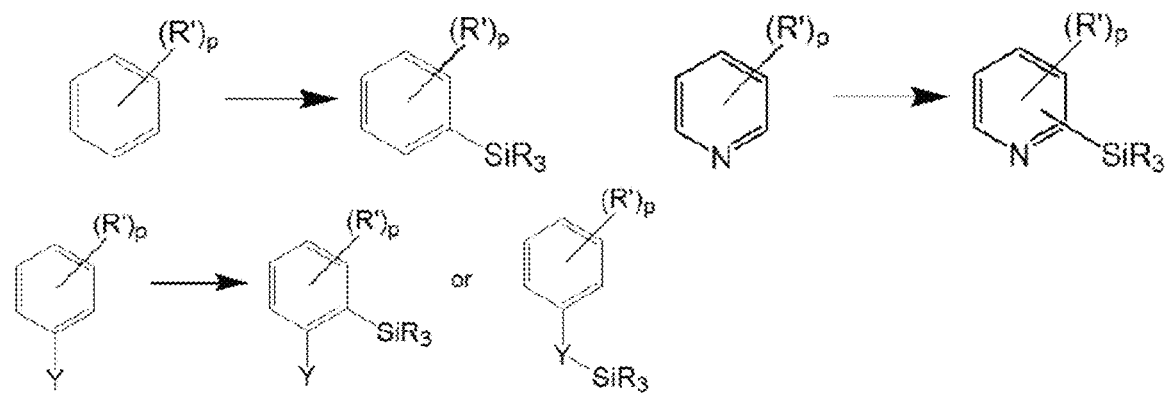
FIGS. 3A and 3B illustrate examples of some of the reactions available by the methods described herein.
Figure 3B:
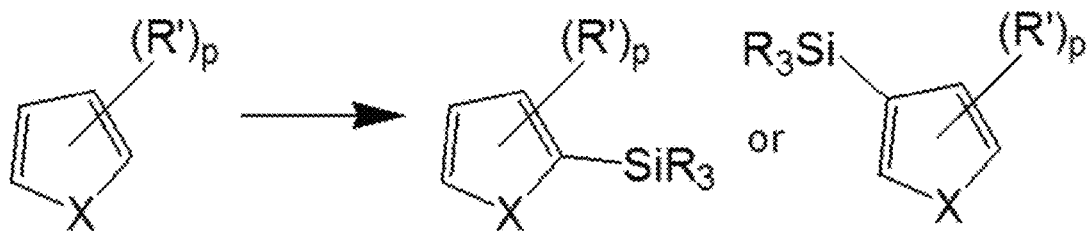
Figure 4A:
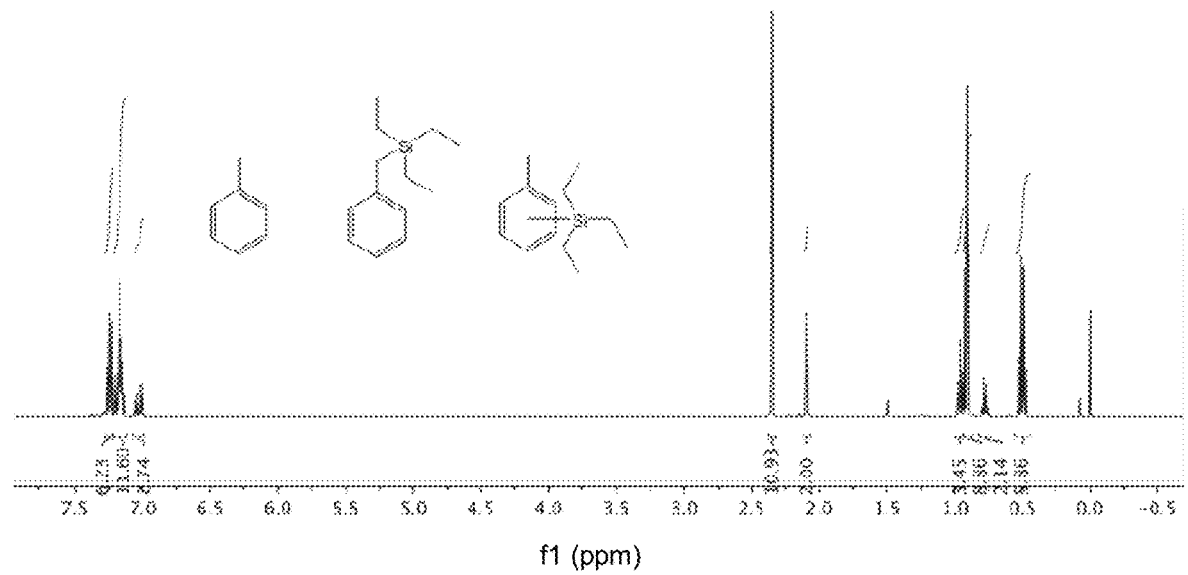
Figure 4B:
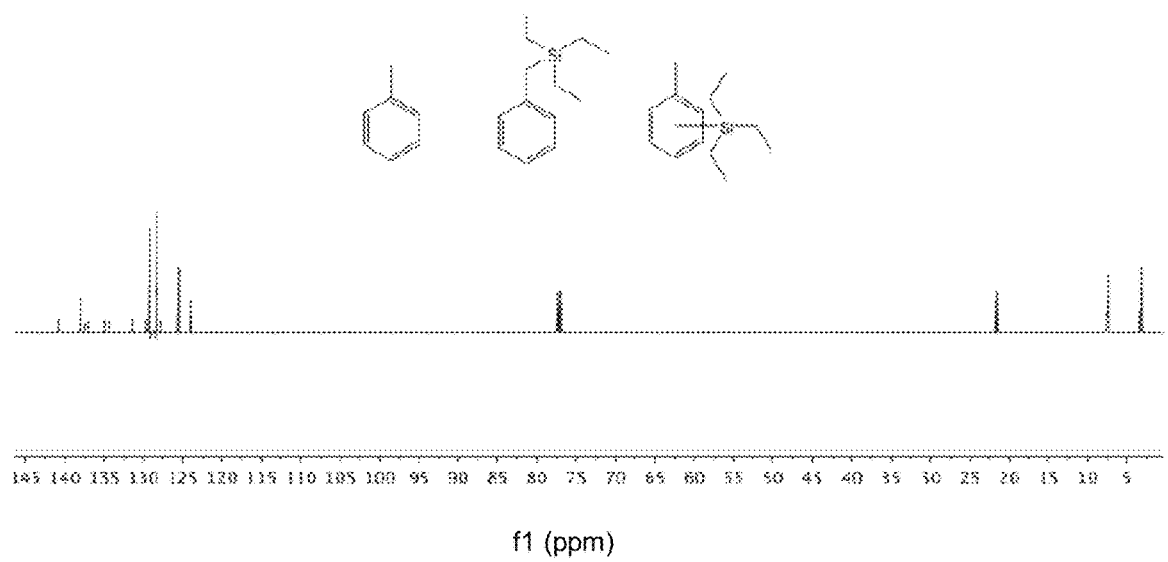
Figure 5A:
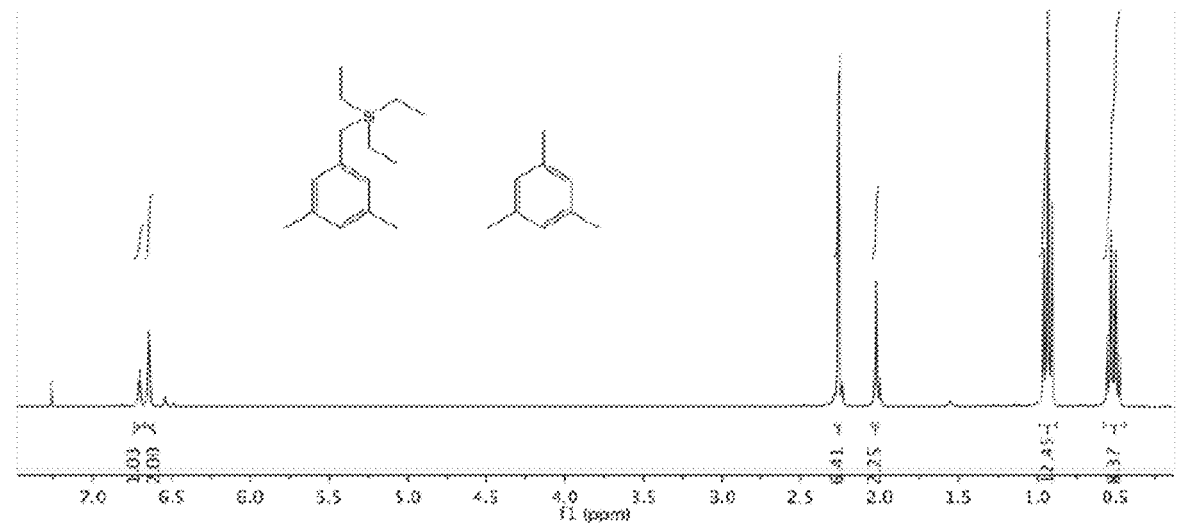
Figure 5B:
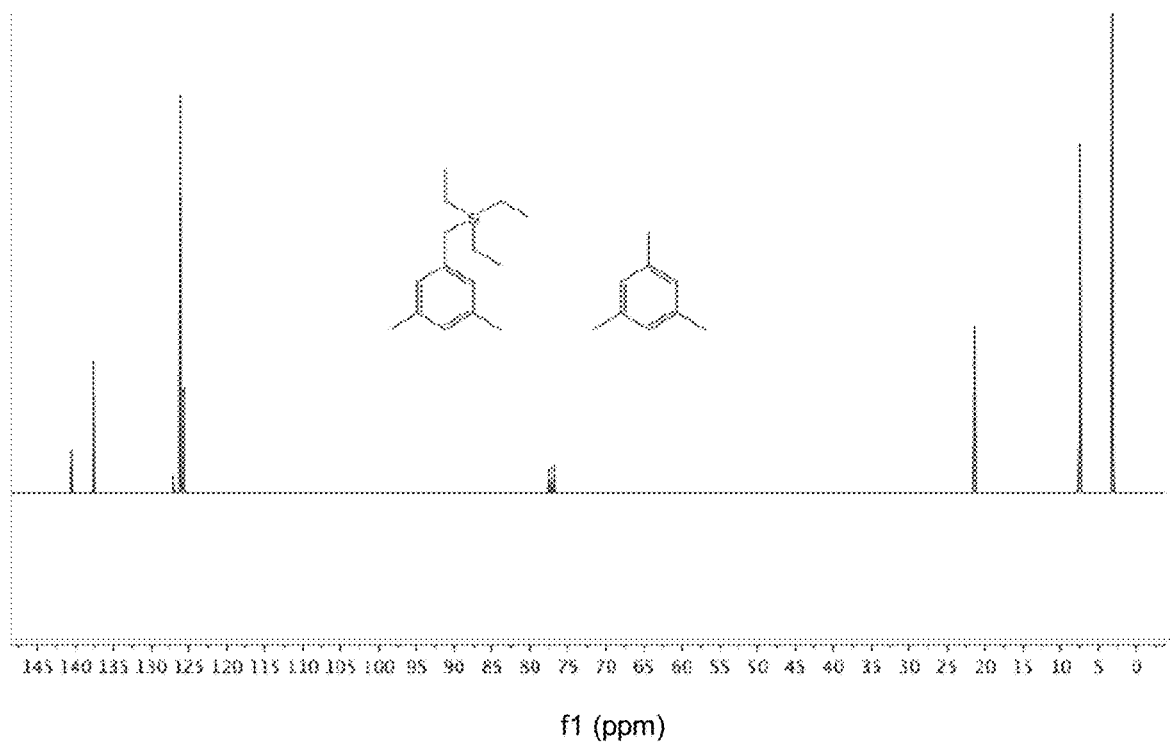
Figure 6A:
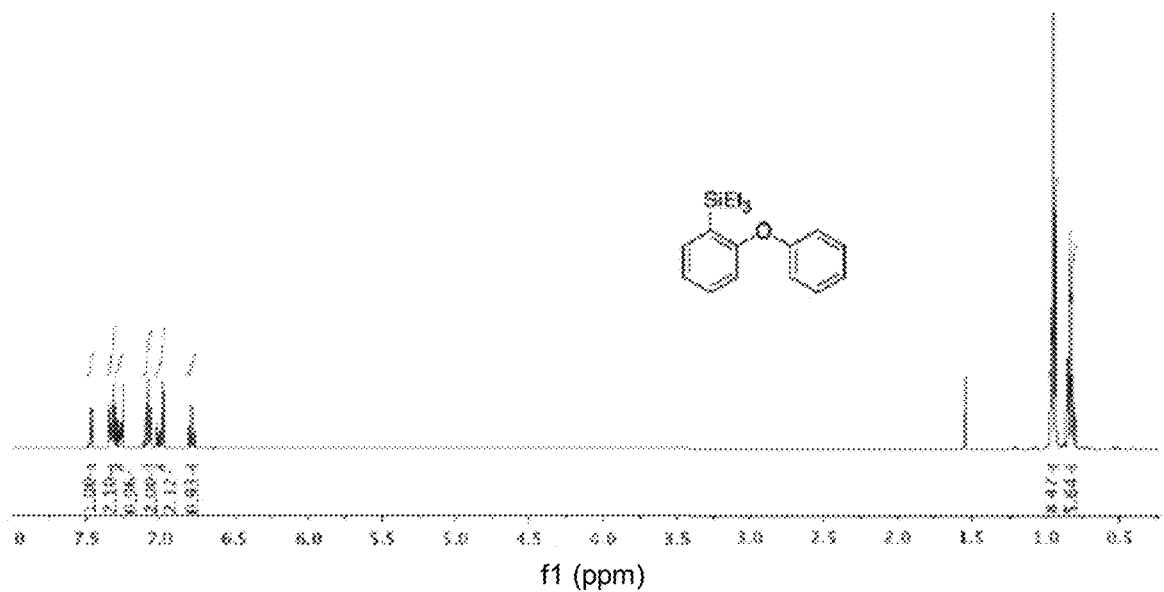
Figure 6B:
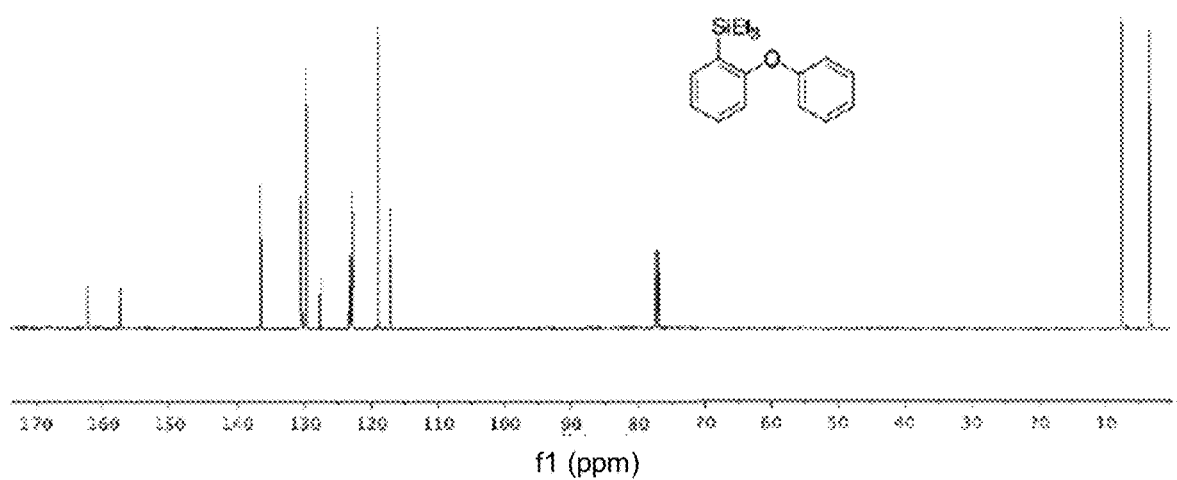

Dibenzofuran (1, 16.8 mg, 0.1 mmol, 1 equiv.), KOt-Bu (22.5 mg, 0.2 mmol, 2 equiv.) and Et₃SiH (80 microliters, 0.5 mmol, 5 equiv.) were heated in 0.4 ml of toluene for 1 hour at 100° C. inside the glovebox. After this time reaction mixture was diluted with 0.8 ml of toluene and filtered into an EPR tube. The reaction mixture was found to be EPR active and the spectrum was recorded within 20 min after filtration (FIG. 2). In a control experiment recorded without dibenzofuran, the same signal was observed albeit with lower intensity. These results are consistent with reactive radicals that have been documented for homolytic aromatic substitution reactions. The addition of 1, 10-phenanthroline in conjunction with KOt-Bu was found to be detrimental since no conversion of 1 was observed.

Example 5.9: Optimization Details for the Cleavage of Dibenzofuran

Experiments were conducted using the General Methods described in Examples 1 and 3, unless otherwise indicated. Yields were reproducible within ±2. It is noteworthy here that low levels of base, especially substoichiometric amounts of base relative to the substrate, even at these elevated temperatures, resulted in the highest yields of silylated products, relative to cleavage products.

TABLE 2

Results of optimization for cleavage and silylations of dibenzofuran

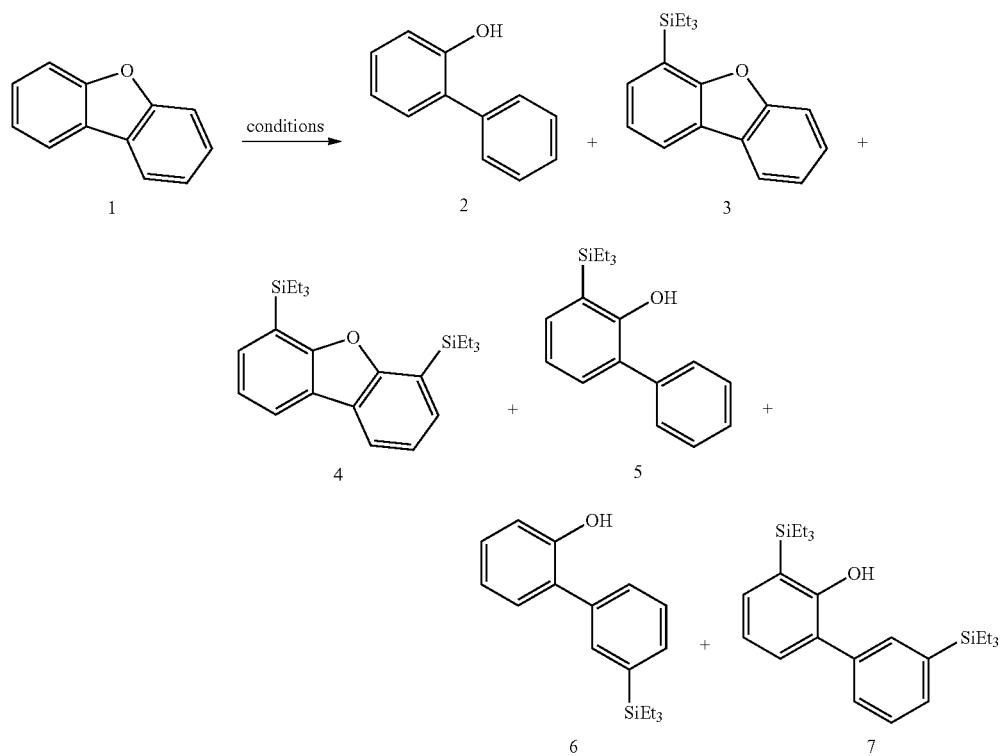

| Entry | Et₃SiH (equiv) | Base (equiv) | Solvent | T, °C. | Conv (%) [a] | 2 | 3 | 4 | 5 | 6 | 7 |
|---|---|---|---|---|---|---|---|---|---|---|---|
| 1 | 0 | KOt-Bu (2) | Toluene | 100 | 0 | — | — | — | — | — | — |
| 2 | 5 | None | Toluene | 100 | 0 | — | — | — | — | — | — |
| 3[a] | 5 | KOt-Bu (2) | Toluene | 100 | 70 | 34 | 28 | 4 | — | — | — |
| 4[b] | 5 | KOt-Bu | Toluene | 100 | 98 | 38 | 16 | 10 | 21 | 2 | 7 |
| 5[c] | 5 | KOt-Bu (2) | Toluene | 100 | 98 | 5 | 28 | 46 | — | — | — |
| 6 | 4 | KOt-Bu (2) | Toluene | 100 | 100 | 41 | 17 | 15 | 12 | 1 | 9 |
| 7 | 3 | KOt-Bu (2) | Toluene | 100 | 96 | 42 | 20 | 9 | 13 | 1 | 4 |
| 8 | 2 | KOt-Bu (2) | Toluene | 100 | 87 | 34 | 30 | 10 | 6 | 1 | 3 |
| 9 | 1 | KOt-Bu (2) | Toluene | 100 | 56 | 19 | 29 | 1 | 2 | — | 1 |
| 10 | 5 | KOt-Bu (0.5) | Toluene | 100 | 89 | 12 | 48 | 20 | 9 | — | 1 |
| 11 | 2 | KOt-Bu (5) | Toluene | 100 | 66 | 9 | 43 | 8 | 2 | — | — |
| 12 | 3 | KOt-Bu (2) | Toluene | 100 | 97 | 63 | 10 | 1 | 22 | — | 2 |
| 13 | 5 | KH (1) | Dioxane | 100 | 49 | 1 | 43 | 5 | — | — | — |
| 14 | 5 | KOt-Bu (2) | Dioxane | 100 | 70 | 25 | 28 | 10 | 4 | 1 | 1 |
| 15[d] | — | KOt-Bu (2) | Et₃SiH | 100 | 99 | 26 | 13 | 25 | 11 | 1 | 21 |
| 16 | 5 | KOt-Bu (2) | Toluene | 80 | 98 | 29 | 18 | 26 | 9 | — | 7 |
| 17 | 3 | KOt-Bu (3) | Mesitylene | 165 | 100 | 85 | 3 | — | 5 | 2 | — |
| 18[e] | 3 | KOt-Bu (3) | Mesitylene | 165 | 100 | 95 | — | — | — | — | — |
| 19 | 2 | KOt-Bu (2) | Mesitylene | 165 | 100 | 62 | 8 | 1 | 12 | 1 | — |
| 20 | 3 | KOt-Bu (2) | Mesitylene | 165 | 97 | 52 | 17 | 5 | 16 | 1 | 2 |
| 21 | 1 | KOt-Bu (1) | Mesitylene | 165 | 57 | 30 | 21 | — | — | — | — |
| 22 | 3 | KOt-Bu (0.5) | Mesitylene | 165 | 85 | 29 | 35 | 15 | 4 | — | 2 |
| 23 | 5 | KOt-Bu (5) | Mesitylene | 165 | 100 | 77 | 3 | 0 | 3 | 8 | — |
| 24 | 3 | KH (3) | Mesitylene | 165 | 100 | 66 | 3 | 0 | 5 | 11 | — |
| 25 | 3 | KOEt (3) | Mesitylene | 165 | 100 | 85 | 4 | 0 | 1 | 8 | — |
| 26 | 3 | KOEt (3) | Mesitylene | 165 | 95 | 77 | 10 | 11 | — | — | — |
| 27 | 3 | KOEt (3) | Toluene | 100 | 40 | 19 | 19 | 2 | — | — | — |
| 28 | 3 | KOMe (3) | Mesitylene | 165 | 64 | 31 | 27 | 2 | 3 | 1 | — |
| 29 | 3 | NaOt-Bu (3) | Mesitylene | 165 | 0 | — | — | — | — | — | — |
| 30 | 3 | LiOt-Bu (3) | Mesitylene | 165 | 0 | — | — | — | — | — | — |
| 31 | 3 | NaOEt (3) | Mesitylene | 165 | 0 | — | — | — | — | — | — |
| 32[f] | 3 | CsOR (2) | Toluene | 100 | 89 | 75 | 3 | 11 | — | — | — |
| 33 | 3 | KOt-Bu (3) | Benzene | 85 | 96 | 37 | 20 | 13 | 12 | — | 9 |
| 34 | 5 | KOt-Bu (2) | DMF | 100 | 0 | — | — | — | — | — | — |
| 35 | 5 | KOt-Bu (2) | DMA | 100 | 0 | — | — | — | — | — | — |
| 36 | 5 | KOt-Bu (2) | Diglyme | 100 | 0 | — | — | — | — | — | — |
| 37 | 5 | KOt-Bu (2) | t-BuOH | 100 | 0 | — | — | — | — | — | — |
| 38 | 5 | KOt-Bu (2) | Diisopropyl carbonol | 100 | 0 | — | — | — | — | — | — |

TABLE 2-continued

| 39 | 3 | KOt-Bu (3) | Methyl cyclohexane | 160 | 100 | 82 | — | — | 13 |
| 40[g] | PMHS (10) | KOt-Bu (3) | Methyl cyclohexane | 85 | 5-7 | — | — | — | — | — | — |

[a]GC yields and conversions are reported using tridecane as the standard
[b]the reaction was performed in 0.05M solution.
[c]reaction conducted open to an Ar line
[d]the reaction was performed in neat Et₃SiH.
[e]with 1,4-cyclohexadiene (100 equivalent) co-solvent
[f]R = 2-ethylhexyl.
[g]using polymethylhydrosiloxane (PMHS) instead of Et₃SiH as organosilane Example 5.10: Reductive Cleavage of Diaryl Ethers In order to explore the cleavage of aryl ether C—O bonds in unstrained substrates and probe if it proceeds without undesired over reduction of the resulting aromatic fragments, diphenyl ether was subjected to the additives-free optimized reaction conditions described above. This substrate provided benzene and phenol in moderate yields (Table 3, Entry 1) with the rest of the mass balance being attributed principally to silylated as well as other unidentified products. With this result in hand, the reactivity of more complex diaryl ethers was evaluated. Both symmetrical and unsymmetrical diaryl ethers were shown to be competent substrates and underwent C—O cleavage with good to excellent efficiencies (Entries 2-7). Many of the evaluated diaryl ethers proved more reactive as compared to diphenyl ether and allowed for the use of milder reaction conditions. In the case of 1-naphthyl phenyl ether (Entry 5), bond cleavage occurred regiospecifically at the naphthyl C—O bond to furnish naphthalene and phenol in 70% and 91% yield respectively, with no 1-naphthol or benzene detected. With the unsymmetrical dinaphthyl ether (Entry 5), C—O bond reduction occurred regioselectively to provide 2-naphthol and 1-naphthol in good combined yield with approximately a 4:1 ratio of the two isomers, respectively. The unsymmetrical para-phenyl substituted diphenyl ether (Entry 7) reacts with good overall yield and with moderate regioselectivity for reduction of the slightly more electron rich C—O bond indicating the apparent influence of electronic effects in site selectivity of C—O bond cleavage. This factor becomes determining for the selectivity of cleavage of 4-O—5 lignin models that contain strong methoxy donors adjacent to the C-0 bond being broken (vide infra, Scheme 2). Such selectivity is complementary to that reported by other for homogeneous Ni catalyzed reduction with dihydrogen wherein unsymmetrical diaryl ethers were preferentially cleaved at the side of the more electron-deficient aryl ring.

TABLE 3

Reductive cleavage of diaryl ethers[a]

$$Ar_1-O-Ar_2 \xrightarrow[165°C., 20\,h, Mes]{Et_3SiH\,(3);\,KOt\text{-}Bu\,(3)} Ar_{1,2}-H + Ar_{1,2}-OH$$

| Entry | Diaryl ether | Conv. (%) | Ar₁—H Ar₂—H | Ar₁—OH Ar₂—OH |
|---|---|---|---|---|
| 1 | Ph—O—Ph | 96 | 64 | 65 |
| 2 | (4-tBu-C₆H₄)—O—(4-tBu-C₆H₄) | 190 | 76 | 98 |
| 3 | (4-Me-C₆H₄)—O—(4-Me-C₆H₄) | 100 | 52 | 84 |
| 4[b] | (2-naphthyl)—O—(2-naphthyl) | 100 | 50 | 88 |

TABLE 3-continued

Reductive cleavage of diaryl ethers[a]

$$Ar_1\text{—}O\text{—}Ar_2 \xrightarrow[165°\text{ C., 20 h, Mes}]{Et_3SiH\ (3);\ KOt\text{-}Bu\ (3)} Ar_{1,2}\text{—}H\ +\ Ar_{1,2}\text{—}OH$$

| Entry | Diaryl ether | Conv. (%) | $Ar_1$—H $Ar_2$—H | $Ar_1$—OH $Ar_2$—OH |
|---|---|---|---|---|
| 5[c] | 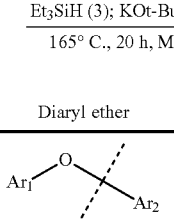 $Ar_1$ = phenyl $Ar_2$ = 1-naphthyl | 100 | — 70 | 91 — |
| 6[d] | 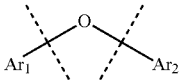 1:4 $Ar_1$ = 2-naphthyl $Ar_2$ = 1-naphthyl | 100 | 57 | 58 15 |
| 7[d] | 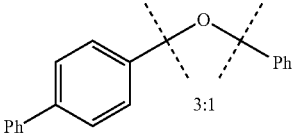 3:1 $Ar_1$ = 4-Ph-Ph $Ar_2$ = Ph | 100 | 41 19 | 21 65 |

[a]GC yields and conversions are reported using tridecane as a standard.
[b]Trace amount of 1,2,3,4-tetrahydronaphthalene was detected.
[c]Reaction was run at 100° C. for 20 h in toluene with 2 equiv. each of Et₃SiH and KOt-Bu.
[d]Reaction was run at 75° C. for 40 h in toluene.

Example 5.11: Reductive Cleavage and Silylations of Aryl Alkyl Ethers

Reductions and silylations of aryl alkyl ethers were conducted under the optimized conditions applied to diaryl ethers to probe the cleavage selectivity of sp2 versus sp3 C—O bond. The reaction of 2-methoxynaphthalene gave 2-naphthol as the major product in moderate yield (Scheme 1). GC-MS analysis of the crude reaction mixture indicated the presence of trace amounts of naphthalene along with 2-methylnaphthalene and further reduced species, including products of partial aromatic reduction. Compounds presumably derived from 2-naphthol silylation were also detected. Likewise, cleavage of 2-ethoxynapthalene under the same conditions gave 2-naphthol in slightly higher yield, but with the same or analogous side products. Sterically bulkier ethers were investigated to probe the versatility and possible mechanism of the C—O bond cleavage. Despite the large alkyl substituent adjacent to the ether oxygen, reaction of 2-neopentyloxynaphthalene provided 2-naphthol in approximately the same yield as with the less bulky substrates. Even 2-tert-butyloxynapthalene was cleaved to give the expected naphthol in 55% yield (Scheme 1). Control experiments performed at identical conditions but without triethylsilane provided 2-naphthol in cases of 2-ethoxy- and 2-tert-butyloxynapthalene albeit with substantially diminished yields. Since 2-methoxy- and 2-neopentyloxy-substrates remained intact in such silane-free cleavages, a b elimination mechanism is likely to be operative. When attempting to reduce 4-tert-butyl and 4-methyl anisoles under the standard conditions, the yields of the corresponding phenols were high, likely because of more challenging silylation of the substituted phenyl ring for the steric reasons (Scheme 2).

Scheme 1. Reductive Cleavage of Aryl Alkyl Ethers at Elevated Temperatures

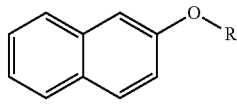

|  | R | A (%) | B (%) |
|---|---|---|---|
|  | Me | 58 | 0 |
|  | Et | 62 | 22 |
|  | t-Bu | 55 | 24 |
|  | neopentyl | 65 | 0 |

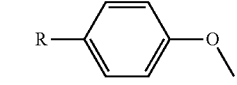

|  | R | A (%) |
|---|---|---|
|  | Me | 88 |
|  | t-Bu | 88 | method A: Et₃SiH (3), KOt-Bu (3), 165° C., 20 h, Mes
method B: KOt-Bu (2), 165° C., 20 h, Mes Overall, the selectivity for alkyl C—O bond scission contrasts with that observed in Ni- and borane catalyzed C—O cleavage reactions where aryl C—O reduction occurs. It is also notable that under these conditions only trace amounts of naphthalene ring hydrogenation products were observed, which contrasts with the results of silane-based ionic hydrogenations reported in the literature.

It is instructive to compare the cleavages of methoxysubstituted diaryl ethers 8 and 11 (Scheme 2) with the results presented above. While aryl alkyl ethers showed strong preference for the reduction of alkyl oxygen over aryl oxygen bonds, both methoxy substrates in Scheme 2 demonstrated a reversal of regioselectivity, furnishing almost exclusively aryl oxygen bond rupture products. While not intending to be bound by the correctness of this theory, this effect may be attributed to the presence of a donor oxygen atom ortho to the C—O bond undergoing rupture. Supporting this inference is the high selectivity of the reductive ring-opening of dibenzofuran derivative 8 that mainly leads to 10. Likewise, preferred formation of phenol and anisole was observed with similar selectivity over phenols 12 and 13 in the cleavage of lignin model 11. One may speculate, without being bound to the correctness of the theory, that such an effect can be rationalized by the oxygen atom resonance stabilization of the positive charge build up during electrophilic activation of the C—O bond that is being broken. In order to test this hypothesis, compound 3 was subject to the reaction conditions and isolated the ring opened phenols 5 and 6 along with the desilylated products 1 and 2 (Scheme 2, inset C). In the absence of resonance stabilization, the selectivity of cleavage was reversed in favor of isomer 5. It is also worth noting that, as formation of 1 and 2 demonstrated, the silylation reaction was thus reversible under the typical reaction conditions. After having illustrated the potential for the challenging 4-O—5 lignin models 8 and 11, this method was tested with an oligomeric ether 14 that contains six $C_{ar}$—O bonds (Scheme 2, inset D). Remarkably, at 165° C. in mesitylene quantitative conversion of 14 was achieved and gave phenol, benzene, resorcinol and other unidentified products with merely 0.5 equivalent of silane per aryl oxygen bond.

In Scheme 2, compounds 1 to 7 refer to the corresponding compounds described in Example 5.9.

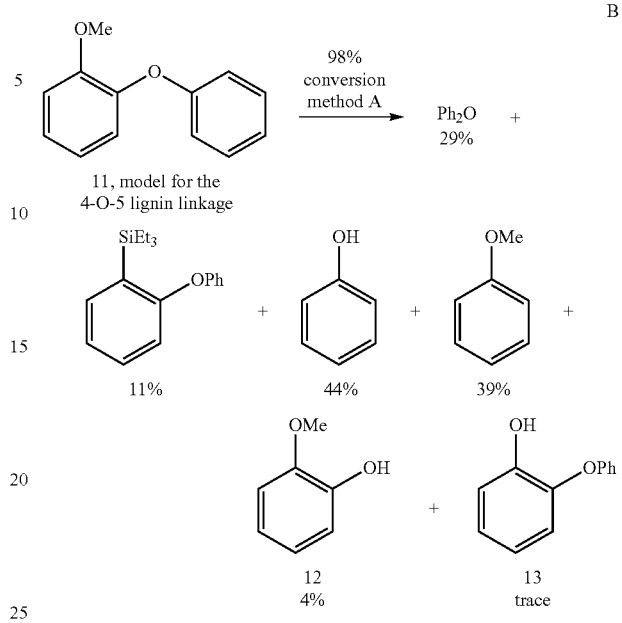

Scheme 2. Method A: Et₃SiH (5) KOt-Bu (2), 100° C., 20 hrs in toluene

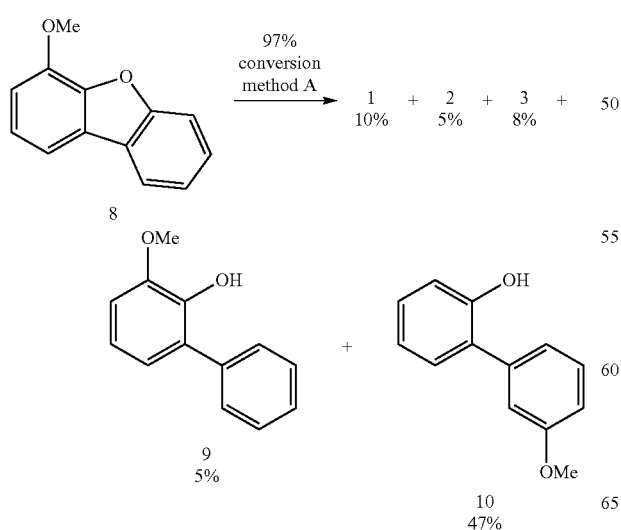

Scheme 2. Method B: Et₃SiH (3) KOt-Bu (3), 165° C., 20 hrs in mesitylene

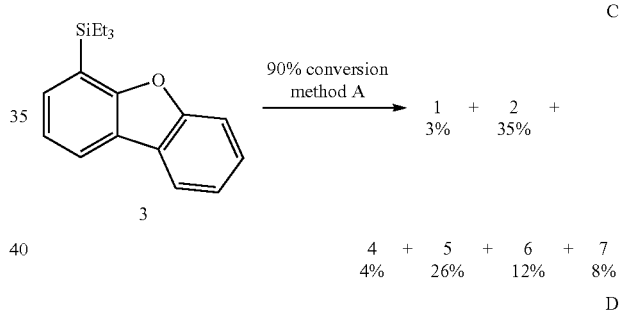

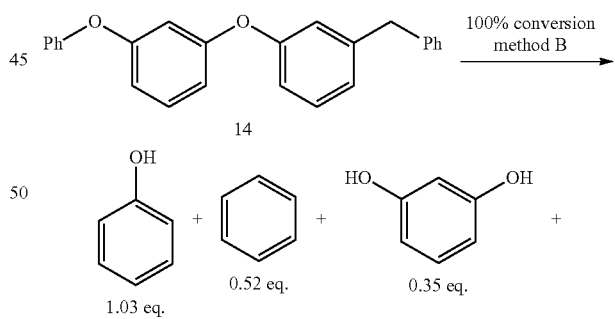

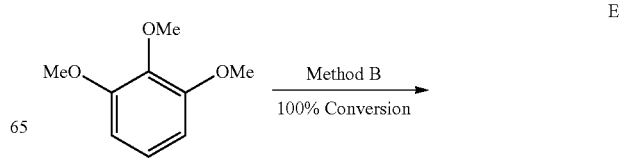

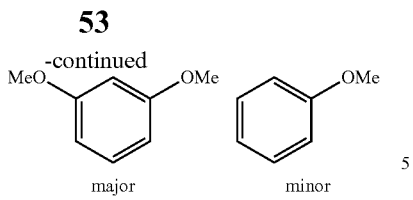

major     minor

Example 5.12: Experiments as to the Effects of Certain Additives on the Cleavage of Dibenzofuran In additional experiments, the reactivity of Et$_3$SiH was tested in the presence of various additives so as to attempt to elucidate a mechanism for the reaction. The results are shown in the following Table 4. None of products 2-7 were identified.

TABLE 4

Effects of additives on the cleavage of dibenzofuran

| Entry | Et$_3$SiH (equiv) | Base (equiv) | Additive | Solvent | T, °C. | Conversion (%) |
|---|---|---|---|---|---|---|
| 1 | 5 | KOt-Bu (2) | 1,10-phen[a] (2) | Toluene | 100 | 5 |
| 2 | 5 | KOt-Bu (2) | 18-crown-6 (2.5) | Toluene | 100 | 0 |
| 3 | 3 | — | KBH$_4$ (3) | Mesitylene | 165 | 0 |
| 4 | 3 | — | KCN (3) | Mesitylene | 165 | 0 |
| 5 | 3 | — | DIBAL[b] (3) | Mesitylene | 165 | 0 |
| 6 | 3 | — | LiAlH$_4$ (3) | Mesitylene | 165 | 0 |
| 7 | 3 | — | Bu$_3$SnH (3) | Mesitylene | 165 | 0 |
| 8 | 5 | — | Me$_4$NF (2) | Toluene | 100 | 0 |
| 9 | 5 | — | Bu$_4$NF (2) | Toluene | 100 | 0 |
| 10 | — | KOt-Bu (2) | KH(2) | Dioxane | 100 | 0 |

[a]1,10-phen is 1,10-phenanthroline.
[b]DIBAL is Diisobutylaluminium hydride

Example 5.13: Experiments with Benzyl Ethers

Experiments were conducted on benzylic ethers using the General Procedures described in Example 3. Surprisingly, the methods were shown to be capable of inducing complete deoxygenation of these lignin model substrates. This type of reactivity appears to be unprecedented in the state-of-the-art homogeneous systems, even at elevated temperatures.

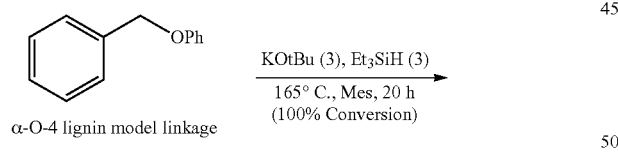

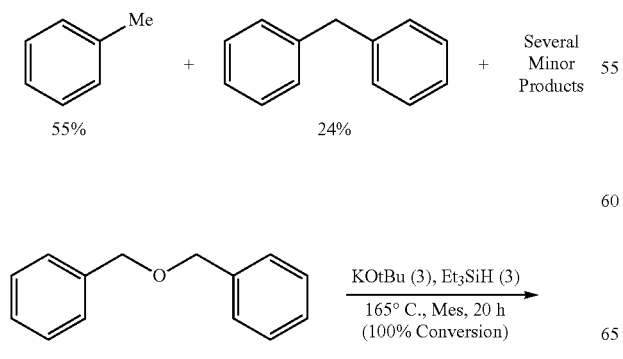

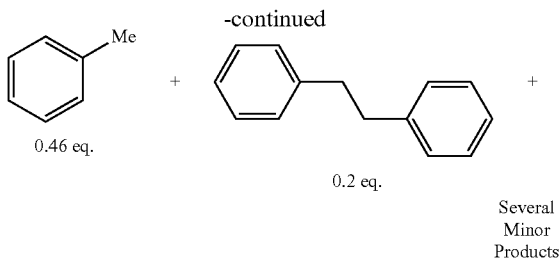

Example 5.14: Experiments with C—N and C—S Heteroaryl Compounds

Experiments were also conducted with C—N and C—S heteroaryl compounds. In the case of compounds comprising C—N bonds, reactivity appeared to be similar to that seen for C—O bonds, and it is reasonably expected that the wide ranging methods used for the latter would result in similar reactivity in the former:

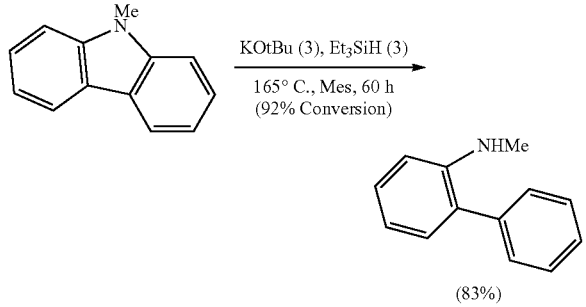

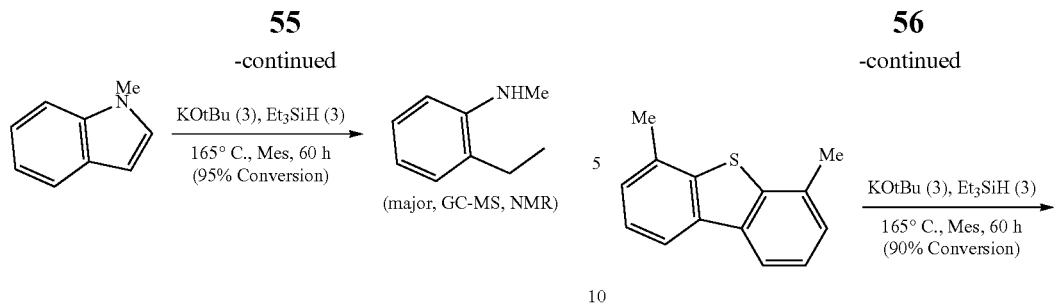

In the case of compounds comprising C—S compounds, the methods appear to generally result in complete desulfurization of the molecules. This difference in reactivities may reflect the differences in bond energies between the C—O, C—N, and C—S bonds (compare C—X bond dissociation energies in phenol (111), aniline (104), and thiophenol (85, all in kcal/mol). Of particular interest was the desulfurization of even hindered dibenzothiophenes under relatively mild conditions. In none of these conversions were single C—S products detected:

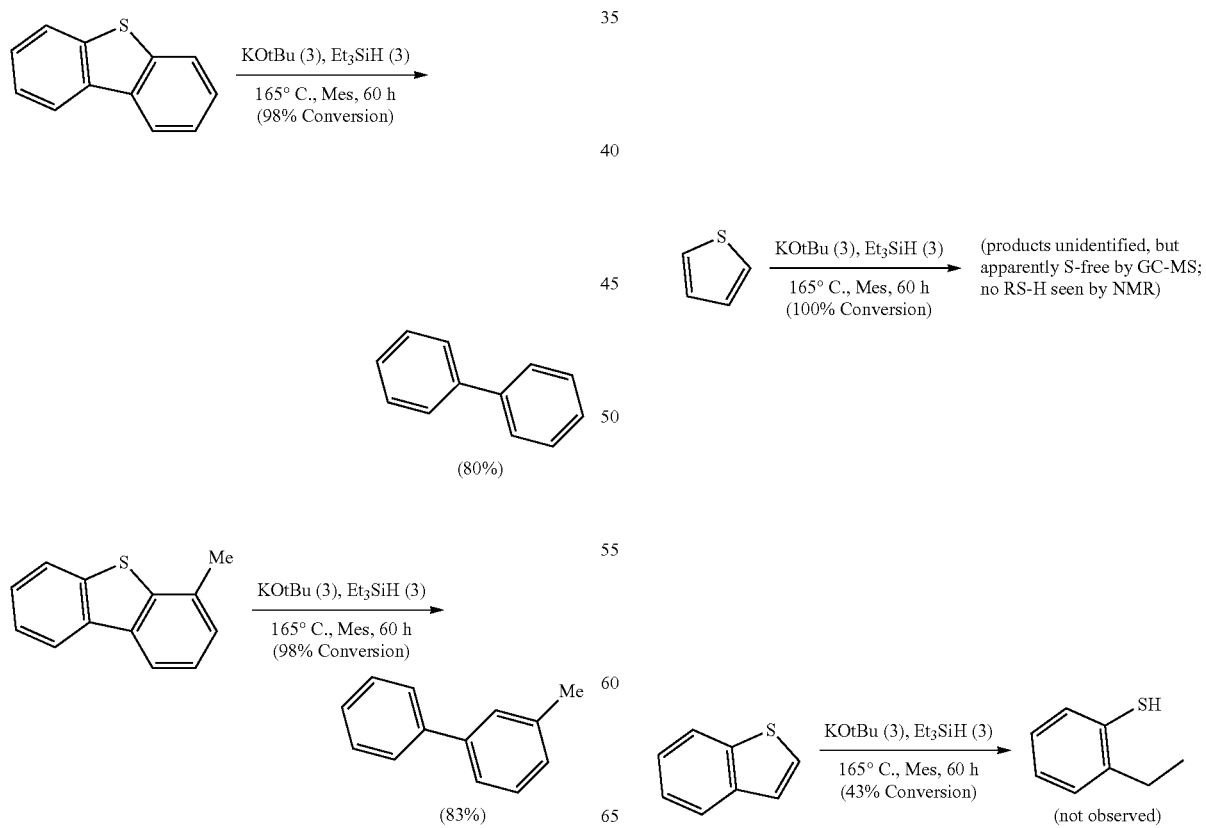

(Products unidentified, except no Ar—S observed by GC-MS; no RS-H by NMR)

Example 6. Exemplary Silylation Reactions

Example 6.1: Triethylsilylation of Arenes at Elevated Temperatures

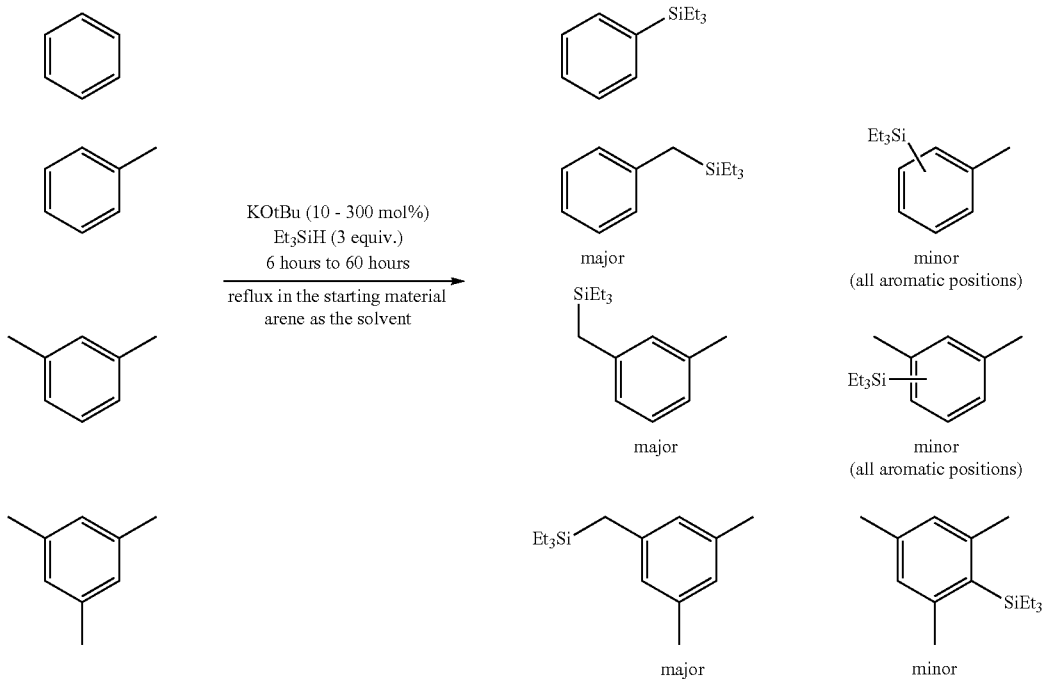

In many instances the formation of the solvent-derived silylated products was observed at elevated temperatures during experiments aimed at C—O, C—N, or C—S bond cleavage when using toluene or mesitylene as solvents at the elevated temperatures used in the reductive cleavage reactions. Since it was not possible to separate the resulting products from their respective parent solvents by column chromatography or distillation, at this point it was difficult to assess their yields, but they are tentatively estimated to be in 5-10% range based on Et$_3$SiH. In case of toluene, the identity of products was confirmed by comparison of the NMR spectra obtained with the literature data (Rychnovsky, et al. J. Org. Chem. 2003, 68, 10135.) Thus, it was concluded that the major product is benzyl triethylsilane (17), which is also consistent with the GC-MS analysis of fragmentation patterns of isomeric products. Likewise, it appeared that silylation of mesitylene proceeds predominantly into the benzylic (or alpha) position. HRMS [$C_{15}H_{26}Si$] calculated 234.1804, measured 234.1804).

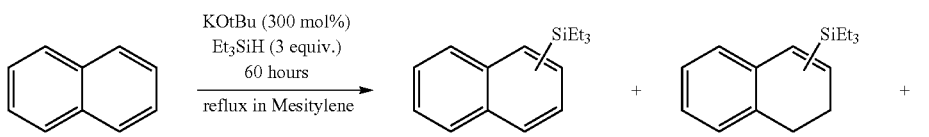

Aromatic amines are also amenable to silylation. In the following case, GC-MS identified the following scheme was operable under the conditions provided:

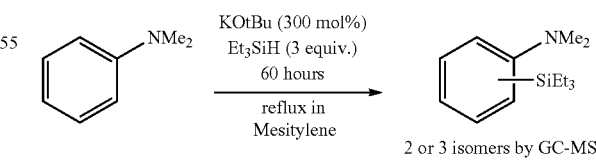

At lower temperatures, this reaction appeared to provide a mixture of product, with no single product identifiable. It is possible, though not confirmed, that the apparent normal proclivity to silylate ortho to the exocyclic amine was inhibited by the steric bulk associated with the two methyl groups.

Example 6.2: Silylation of Aryl Alkyl Ethers and Thioethers at Ambient Temperatures

Example 6.2.1: Triethyl(2-methoxyphenyl)silane

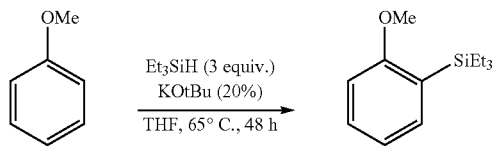

The reaction was conducted according to the General Procedure by heating anisole (54 mg, 0.5 mmol, 1 equiv.), KOt-Bu (11 mg, 0.1 mmol, 0.2 equiv) and Et$_3$SiH (239 microliters, 1.5 mmol, 3 equiv.) in 1 mL of tetrahydrofuran for 65 hours at 65° C. After aqueous work up, the crude reaction mixture was purified by chromatography on silica using hexanes (isochratic) to obtain 59 mg (54%) of the title compound as a colourless oil. $^1$H NMR (500 MHz, THF-d8) δ 7.40-7.17 (m, 2H), 7.01-6.81 (m, 2H), 3.77 (s, 3H), 1.02-0.85 (m, 9H), 0.87-0.74 (m, 6H). $^{13}$C NMR (126 MHz, THF-d8) δ 164.58, 135.52, 130.42, 123.92, 120.08, 109.23, 54.09, 6.93, 3.22.

Example 6.2.2: Triethyl(3-methoxynaphthalen-2-yl)silane

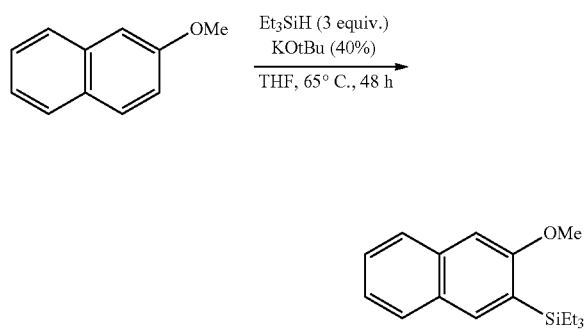

The reaction was conducted according to the General Procedure by heating 2-methoxynaphthalene (79 mg, 0.5 mmol, 1 equiv.), KOt-Bu (19.6 mg, 0.18 mmol, 0.35 equiv.) and Et$_3$SiH (319 microliters, 2.0 mmol, 4 equiv.) in 1 mL of tetrahydrofuran for 48 hours at 65° C. After aqueous work up, the crude reaction mixture was purified by chromatography on silica eluting with hexanes (isochratic) to obtain 79 mg (58%) of the title compound as colourless oil. $^1$H NMR (500 MHz, THF-d8) δ 7.84 (s, 1H), 7.78-7.73 (d, 1H), 7.73-7.68 (d, 1H), 7.38 (ddd, J=8.2, 6.8, 1.3 Hz, 1H), 7.27 (ddd, J=8.1, 6.8, 1.2 Hz, 1H), 7.15 (s, 1H), 3.90 (s, 3H), 1.01-0.90 (m, 9H), 0.68-0.53 (m, 6H). $^{13}$C NMR (126 MHz, THF-d$_8$) δ 163.03, 137.88, 136.83, 130.10, 128.58, 128.09, 127.29, 127.21, 124.03, 104.57, 55.25, 8.02, 7.48.

Figure 7A:
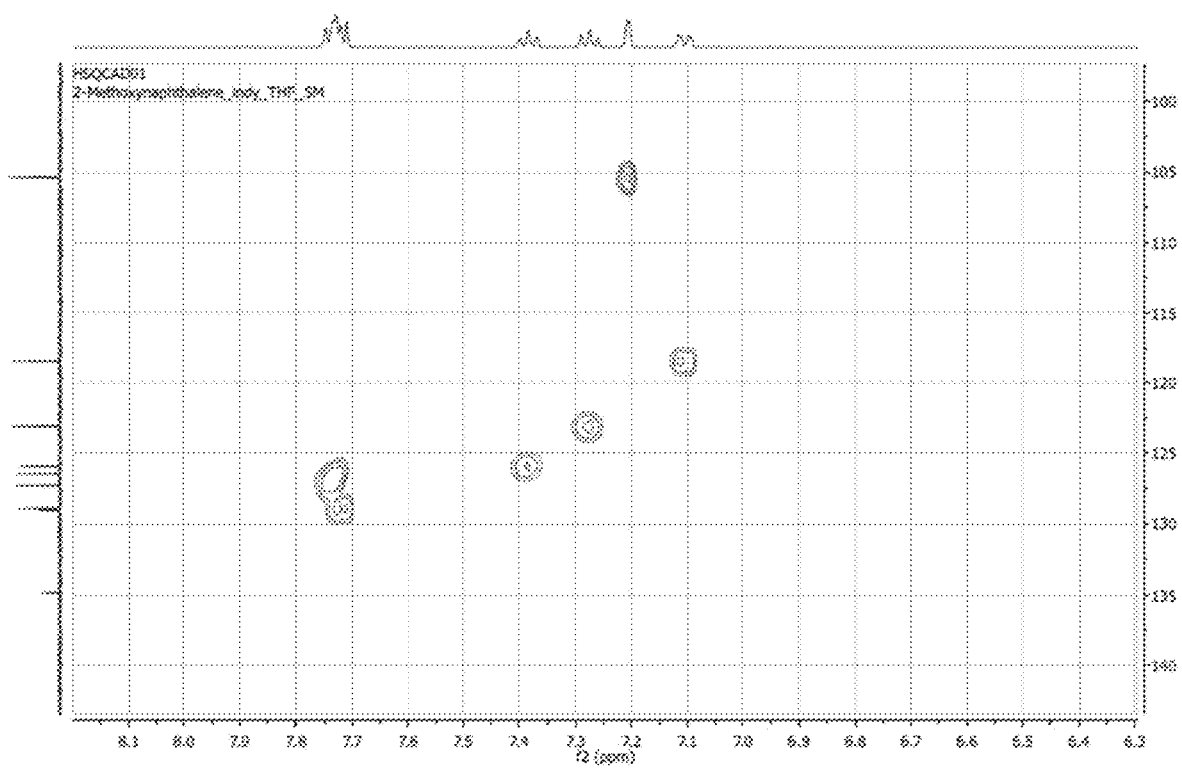
Figure 7B:
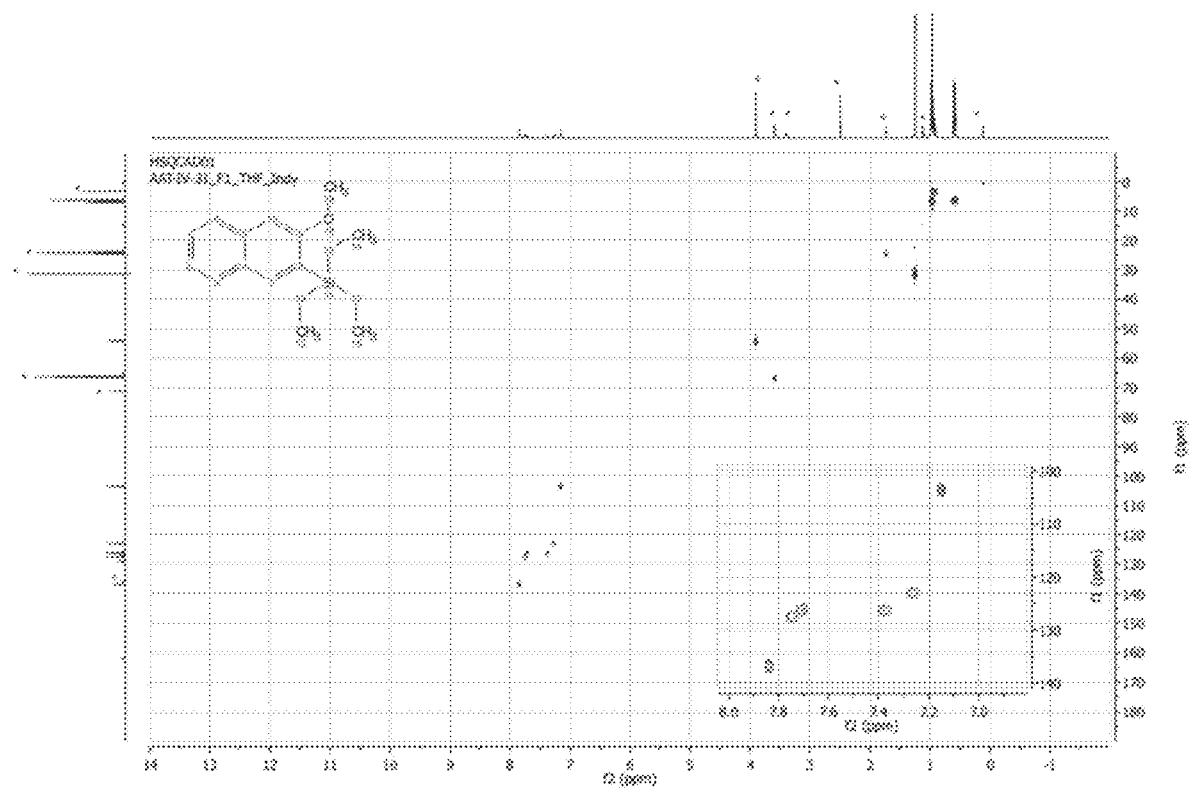

HRMS. [C$_{17}$H$_{24}$OSi] calculated 272.1608, measured 272.1596. The HSQC spectra of the 2-methoxynaphthalene and its reaction product are provided in FIG. 7.

Interestingly, the reaction starting with 1-methoxynaphthalene did not result in silylated product:

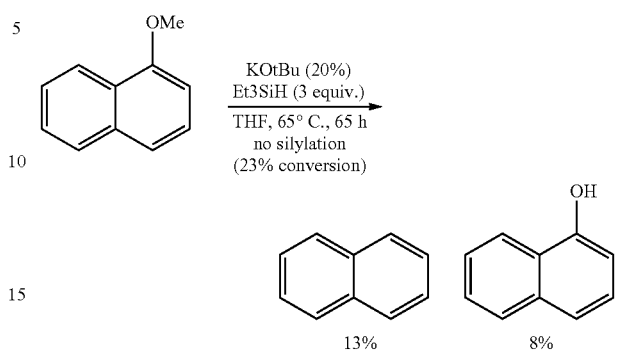

The reaction was conducted according to the General Procedure by heating 1-methoxynaphthalene (79 mg, 0.5 mmol, 1 equiv.), KOt-Bu (11.2 mg, 0.1 mmol, 0.1 equiv) and Et$_3$SiH (240 microliters, 1.5 mmol, 3 equiv.) in 1 mL of tetrahydrofuran for 65 hours at 65° C. The reaction was diluted with diethyl ether (1 mL), quenched with water (0.5 mL) and the organic phase was analyzed by GC-MS, GC-FID and 1H NMR analysis. Analysis by GC-MS and GC-FID (tridecane standard) revealed the formation of aryl C—O cleavage product naphthalene and alkyl C—O bond cleavage product naphthol in 13 and 8 percent yield respectively, notably to the complete exclusion of any silylated species.

Example 6.2.3 Silylation of Diphenyl Ether

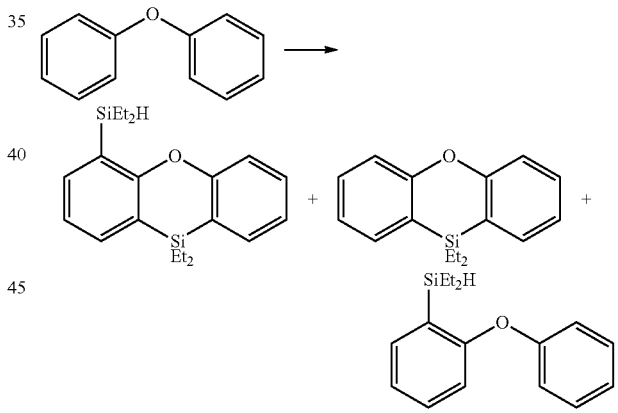

The reaction was conducted according to the General Procedure by heating phenyl ether (85 mg, 0.5 mmol, 1 equiv.), KOt-Bu (11 mg, 0.10 mmol, 0.2 equiv) and Et$_2$SiH$_2$ (194 microliters, 1.5 mmol, 3 equiv.) in 1 mL of tetrahydrofuran for 65 hours at 65° C. After aqueous work up, the crude reaction mixture was purified by chromatography on silica using an 80:2 mixture of hexanes: triethylamine to obtain 68 mg (20%) of the title compound as a colourless oily solid. $^1$H NMR (500 MHz, THF-d$_8$) δ 7.64-7.57 (m, 2H), 7.55 (dd, J=7.3, 1.8 Hz, 1H), 7.41 (ddd, J=8.3, 7.2, 1.8 Hz, 1H), 7.15 (dd, J=8.3, 1.0 Hz, 1H), 7.14-7.09 (m, 2H), 4.34 (Si—H) (p-like, J=1.2 Hz, 1H), 1.06-0.95 (m, 12H), 0.92-0.82 (m, 8H). 13C NMR (126 MHz, THF-d$_8$) δ 166.04, 161.43, 139.74, 137.00, 135.55, 135.05, 132.12, 130.19, 128.79, 123.56, 123.37, 118.41, 9.06, 7.93, 6.70, 4.83. HRMS: [C$_{20}$H$_{27}$OSi$_2$] calculated 339.1601, measured 339.1607.

Figure 8A:
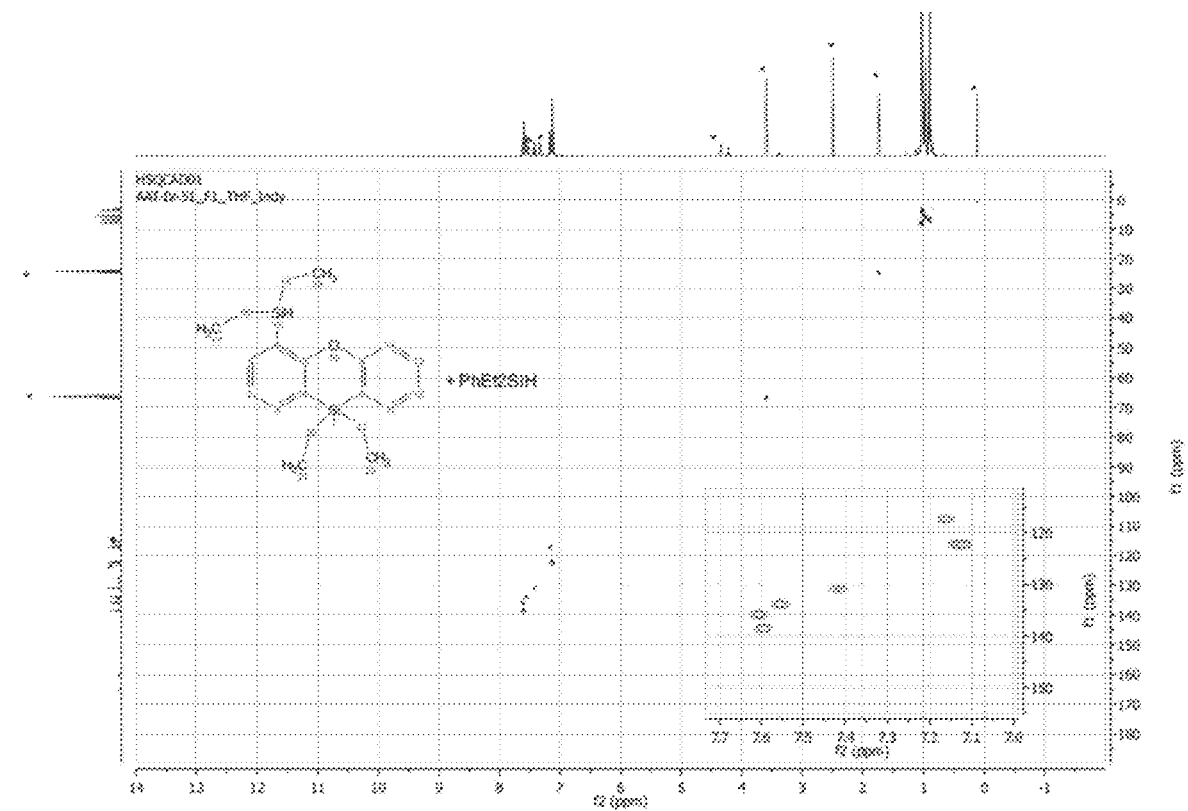
FIGS. 8A and B are the HSQC spectra of two of the products of the reaction between diphenyl ether and diethyl silane, as described in Example 6.2.3.
Figure 8B:
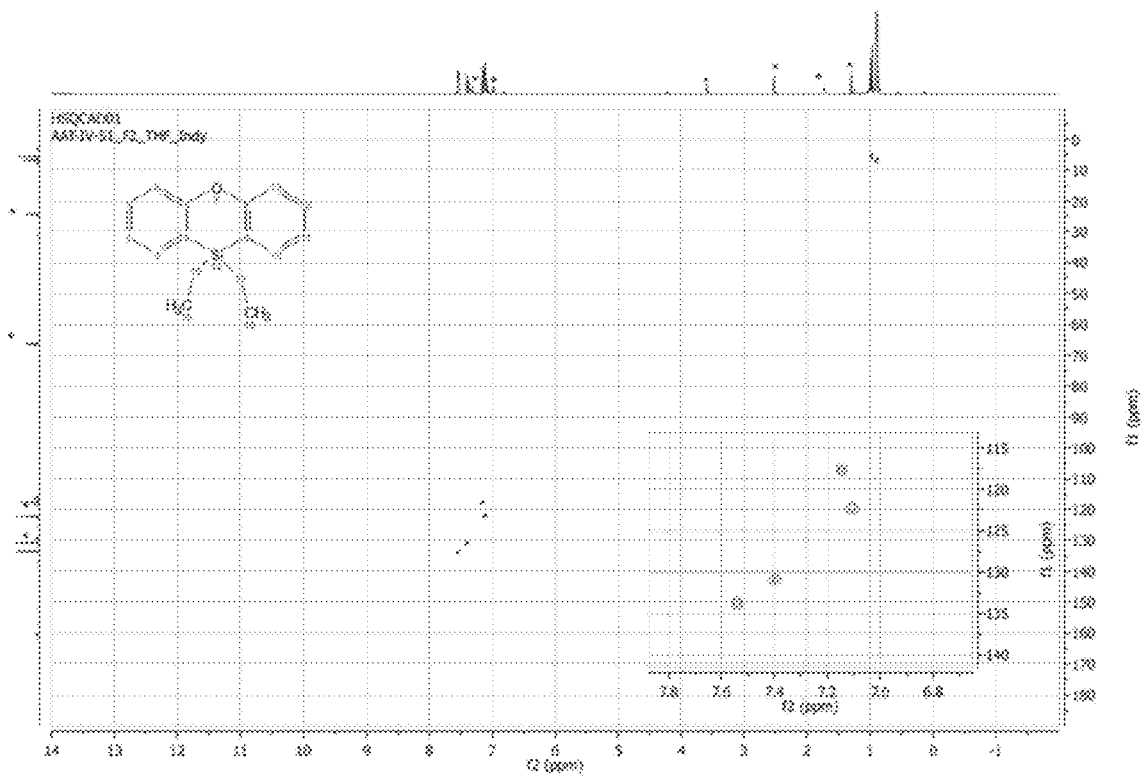

A second fraction of the reaction mixture yielded 34 mg (39%) of the cyclized derivative. ¹H NMR (500 MHz, THF-d₈) δ 7.57-7.50 (m, 2H), 7.40 (ddd, J=8.3, 7.2, 1.8 Hz, 2H), 7.15 (dd, J=8.6, 0.7 Hz, 2H), 7.11 (td, J=7.2, 1.0 Hz, 2H), 0.99-0.95 (m, 4H), 0.92-0.86 (m, 6H). ¹³C NMR (126 MHz, THF-d₈) δ 161.54, 134.96, 132.07, 123.41, 118.80, 117.39, 7.95, 6.72. HRMS: [C₁₆H₁₉OSi] calculated 255.1205, measured 255.1206. The HSQC spectra of these reaction products are provided in FIGS. 8A and 8B.

A third fraction was obtained, containing a product in low yield (ca. 7%) whose spectral characteristics appear to be consistent with the structure of the monosilylated product shown above.

Example 6.2.4: Triethyl((phenylthio)methyl)silane

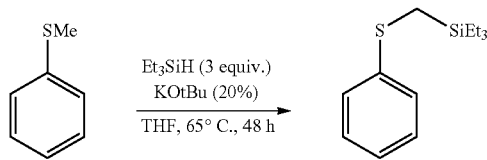

Figure 9A:
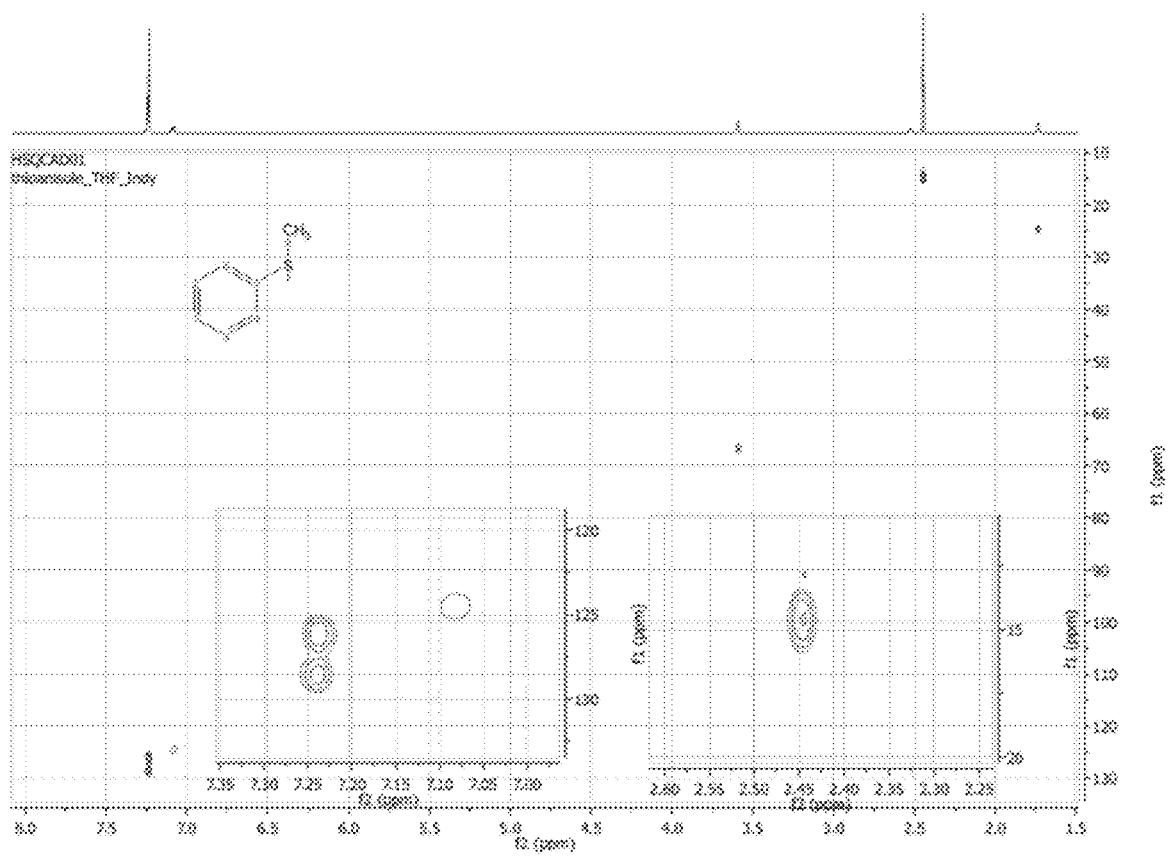
Figure 9B:
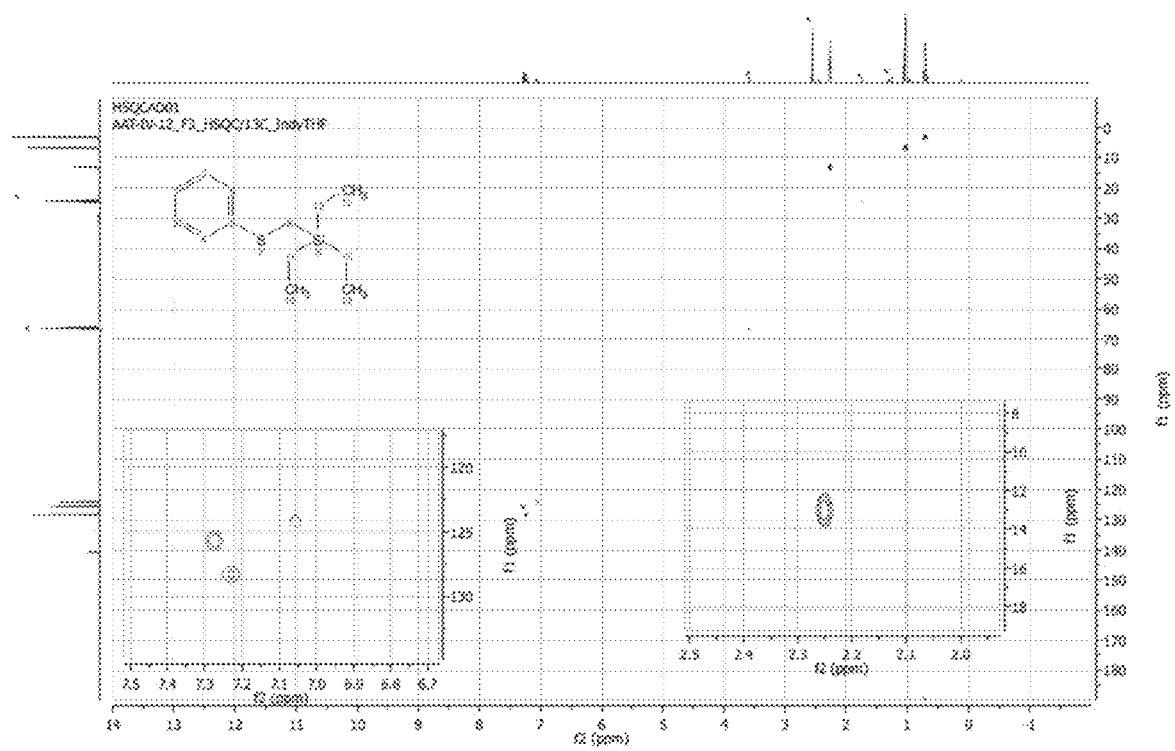

The reaction was conducted according to the General Procedure by heating thioanisole (62 mg, 0.5 mmol, 1 equiv.), KOt-Bu (11 mg, 0.1 mmol, 0.2 equiv) and Et₃SiH (239 microliters, 1.5 mmol, 3 equiv.) in 1 mL of tetrahydrofuran for 65 hours at 65° C. After aqueous work up, the crude reaction mixture was purified by chromatography on silica using hexanes (isochratic) to obtain 81 mg (68%) of the title compound as a colourless oil. ¹H NMR (500 MHz, THF-d8) δ 7.31-7.26 (m, 2H), 7.25-7.19 (m, 2H), 7.11-7.01 (m, 1H), 1.03 (t, J=7.9 Hz, 9H), 0.78-0.60 (m, 6H). ¹³C NMR (126 MHz, THF-d8) δ 140.73, 128.31, 125.69, 124.19, 13.01, 6.62, 3.06. HRMS: [C₁₃H₂₁SSi] calculated 237.1140, measured 237.1133. The HSQC spectra of the thioanisole and its reaction product as provided in FIGS. 9A and 9B.

Example 6.3: Experiments with Heteroaryl Compounds at Ambient Temperatures

A series of experiments were done at ambient (65° C. or below) to test the regioselectivity of several of the more reactive heteroaryl compounds. The test conditions and results are shown below. Yields for all reactions are either by isolation (chromatography on silica gel, or bul-to-bulb distillation) or by GC-FID or NMR analysis using internal standard for quantification. Note that C-3 silylated heteroarenes were found in some cases to be prone to protodelilylation on silica gel. In these cases, bulb-to-bulb distillation was used or, alternatively, silica gel chromatography with ca. 3% triethyl amine added to the eluent, or a combination of both methods. Products were identified as indicated by interpreting available ¹H, ¹³C NMR, and Heteronuclear Single Quantum Coherence (HSQC) spectroscopy, or GC-MS, or a combination of these methods, where possible using comparisons with authentic samples.

Example 6.3.1: 1-methyl-2-(triethylsilyl)-1H-indole

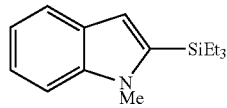

Figure 10:
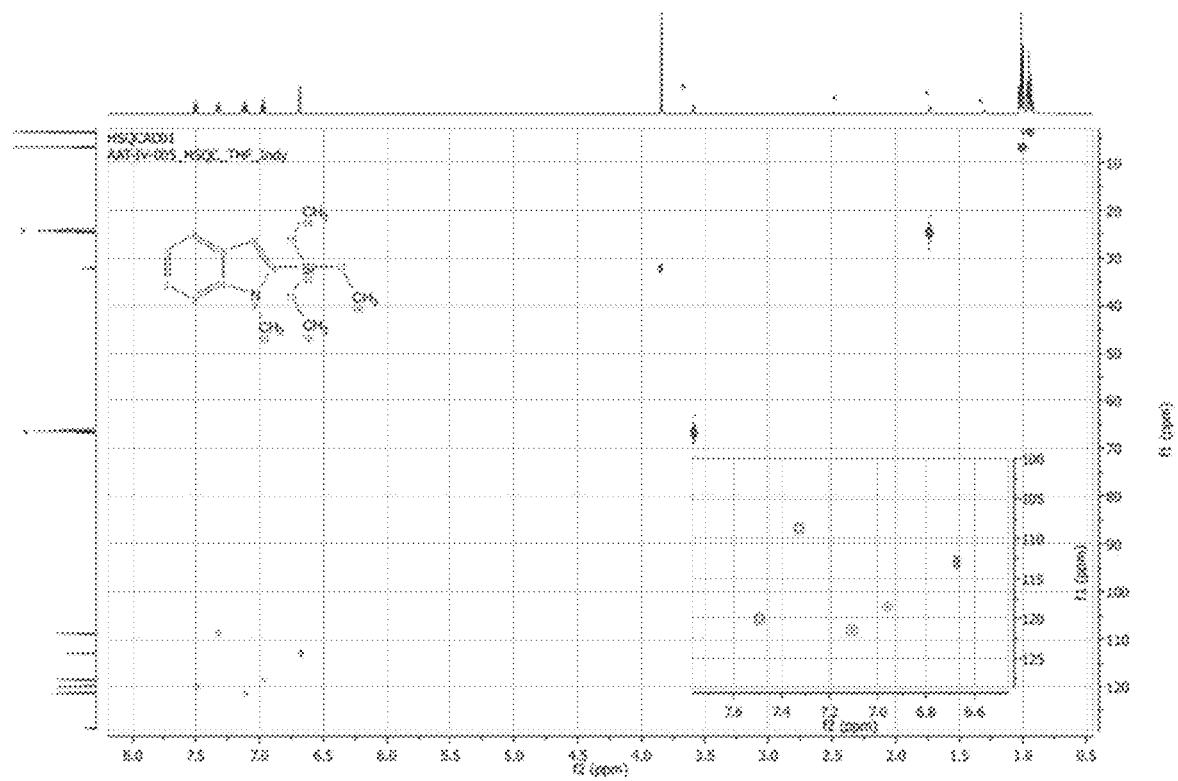

The reaction was conducted according to the General Procedure by heating N-methylindole (66 mg, 0.5 mmol, 1 equiv.), KOt-Bu (8.4 mg, 0.08 mmol, 0.15 equiv.) and Et₃SiH (239 microliters, 1.5 mmol, 3 equiv.) in 1 mL of tetrahydrofuran for 48 hours at 23° C. After aqueous work up, the crude reaction mixture was purified by chromatography on silica eluting with hexanes (isochratic) to obtain 88 mg (72%) of the title compound as a colourless oil. ¹H NMR (500 MHz, THF-d8) δ 7.50 (dt, J=7.9, 1.0 Hz, 1H), 7.32 (dq, J=8.3, 0.9 Hz, 1H), 7.11 (ddd, J=8.2, 6.9, 1.2 Hz, 1H), 6.97 (ddd, J=7.9, 7.0, 0.9 Hz, 1H), 6.68 (d, J=0.9 Hz, 1H), 3.84 (s, 3H), 1.06-0.98 (m, 9H), 0.98-0.92 (m, 6H). ¹³C NMR (126 MHz, THF-d8) δ 140.48, 136.86, 128.70, 121.44, 120.05, 118.51, 112.96, 108.71, 32.18, 6.83, 3.63. The structural characterization of this reaction product is based, in part, on an interpretation of the HSQC spectrum of this reaction product as provided in FIG. 10.

Example 6.3.2: 1-methyl-3-(triethylsilyl)-1H-indole

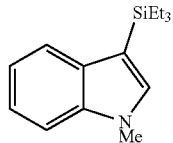

Figure 11:
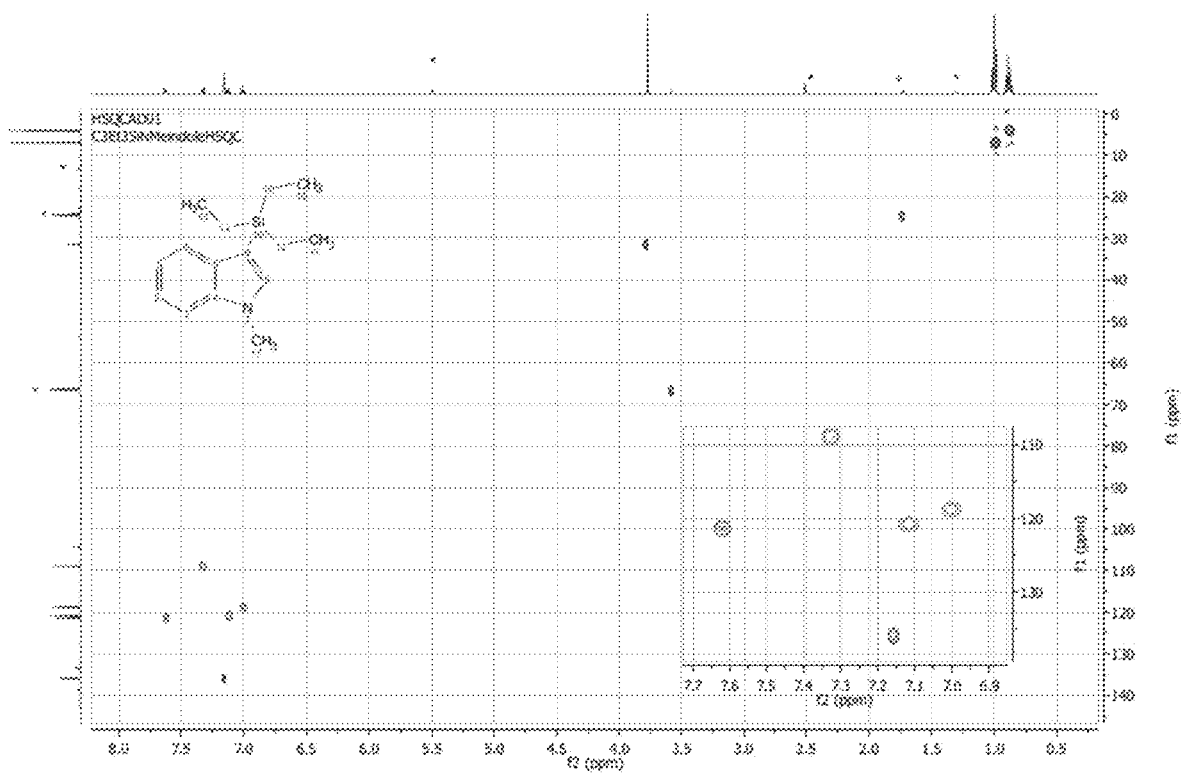

The reaction was conducted according to the General Procedure by heating N-methylindole (66 mg, 0.5 mmol, 1 equiv.), KOt-Bu (56 mg, 0.5 mmol, 1 equiv.) and Et₃SiH (88 microliters, 0.55 mmol, 1.1 equiv.) in 1 mL of tetrahydrofuran for 312 hours at 23° C. After aqueous work up, the crude reaction mixture was purified by chromatography on silica eluting with 95:5 hexanes:NEt₃ (isochratic) to obtain 103 mg (84%) of the title compound as a colourless oil. ¹H NMR (500 MHz, THF-d8) δ 7.63 (dt, J=7.9, 1.0 Hz, 1H), 7.32 (dt, J=8.2, 0.9 Hz, 1H), 7.15 (s, 1H), 7.12 (ddd, J=8.2, 7.0, 1.1 Hz, 1H), 7.01 (ddd, J=8.0, 7.0, 1.1 Hz, 1H), 3.78 (s, 3H), 1.06-0.95 (m, 9H), 0.95-0.83 (m, 6H). ¹³C NMR (126 MHz, THF-d8) δ 138.63, 135.94, 133.37, 121.44, 120.88, 118.79, 108.96, 104.39, 31.61, 7.04, 4.11. The structural characterization of this reaction product is based, in part, on an interpretation of the HSQC spectrum of this reaction product as provided in FIG. 11.

Example 6.3.3: 2-(ethyldimethylsilyl)-1-methyl-1H-indole

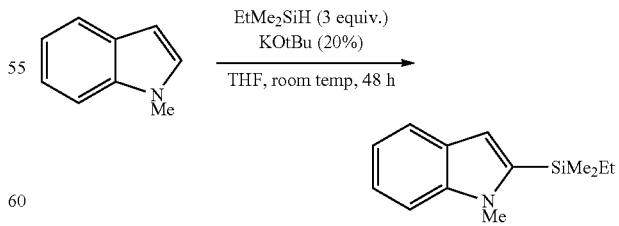

The reaction was conducted according to the General Procedure by heating N-methylindole (62 mg, 0.5 mmol, 1 equiv.), KOt-Bu (11 mg, 0.1 mmol, 0.2 equiv) and EtMe₂SiH (198 microliters, 1.5 mmol, 3 equiv.) in 1 mL of tetrahydrofuran for 48 hours at 23° C. After aqueous work up, the crude reaction mixture was purified by chromatography on silica using hexanes (isochratic) to obtain 80 mg (74%) of the title compound as a colourless oil. $^1$H NMR (500 MHz, THF-d8) δ 7.48 (d, J=7.9 Hz, 1H), 7.31 (dd, J=8.4, 1.0 Hz, 1H), 7.10 (ddd, J=8.2, 6.9, 1.2 Hz, 1H), 6.95 (ddd, J=7.9, 6.9, 0.9 Hz, 1H), 6.64 (d, J=0.9 Hz, 1H), 3.84 (s, 3H), 1.05-0.95 (m, 3H), 0.89 (d, J=7.9 Hz, 2H), 0.38 (s, 6H). $^{13}$C NMR (126 MHz, THF-d8) δ 140.45, 138.94, 128.58, 121.45, 120.10, 118.51, 113.53, 111.90, 108.67, 32.17, 7.37, 6.77, −3.67. HRMS. [$C_{13}H_{19}NSi$] calculated 217.1280; measured 217.1287.

Example 6.3.4: 1-benzyl-2-(triethylsilyl)-1H-indole

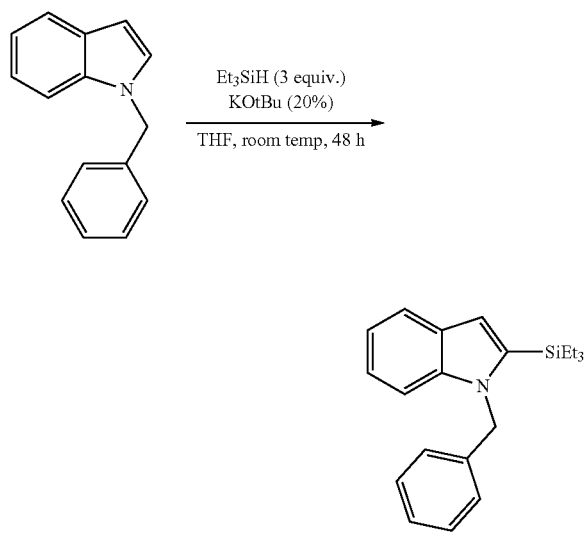

The reaction was conducted according to the General Procedure by heating 1-benzylindole (62 mg, 0.5 mmol, 1 equiv.), KOt-Bu (11 mg, 0.1 mmol, 0.2 equiv) and Et$_3$SiH (239 microliters, 1.5 mmol, 3 equiv.) in 1 mL of tetrahydrofuran for 48 hours at 23° C. After aqueous work up, the crude reaction mixture was purified by chromatography on silica using hexanes (isochratic) to obtain 50 mg (31%) of the title compound as a colourless oily solid. $^1$H NMR (500 MHz, THF-d8) δ 7.56 (ddd, J=7.7, 1.3, 0.7 Hz, 1H), 7.25-7.07 (m, 4H), 7.02 (ddd, J=8.2, 6.9, 1.3 Hz, 1H), 6.98 (ddd, J=7.9, 6.9, 1.1 Hz, 1H), 6.92-6.86 (m, 2H), 6.80 (d, J=0.9 Hz, 1H), 5.52 (s, 2H), 1.06-0.88 (m, 9H), 0.85-0.69 (m, 6H).

Example 6.3.5: 1-benzyl-2-(ethyldimethylsilyl)-1H-indole

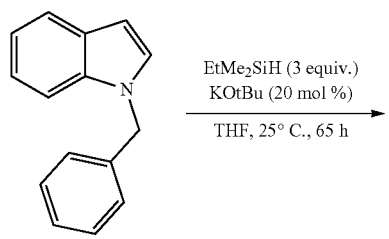

-continued

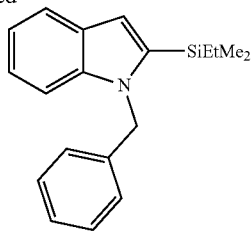

The reaction was conducted according to the General Procedure by heating 1-benzylindole (104 mg, 0.5 mmol, 1 equiv.), KOt-Bu (17 mg, 0.15 mmol, 0.3 equiv) and EtMe$_2$SiH (198 microliters, 1.5 mmol, 3 equiv.) in 1 mL of tetrahydrofuran for 65 hours at 25° C. After aqueous work up, the crude reaction mixture was purified by chromatography on silica using an 80:1:4 mixture of hexanes:diethyl ether:triethylamine respectively to obtain 107 mg (73%) of the title compound as a colourless oil. $^1$H NMR (500 MHz, THF-d$_8$) δ 7.55 (ddd, J=7.7, 1.4, 0.8 Hz, 1H), 7.22-7.16 (m, 2H), 7.16-7.09 (m, 2H), 7.02 (ddd, J=8.2, 6.9, 1.4 Hz, 1H), 6.97 (ddd, J=8.0, 6.9, 1.2 Hz, 1H), 6.86 (ddd, J=7.2, 1.3, 0.7 Hz, 2H), 6.78 (d, J=0.9 Hz, 1H), 5.51 (d, J=1.1 Hz, 2H), 0.95-0.90 (m, 3H), 0.24 (s, 6H). $^{13}$C NMR (126 MHz, THF-d8) δ 141.31, 140.50, 139.94, 130.09, 129.39, 127.90, 126.71, 122.96, 121.45, 120.10, 113.93, 110.81, 50.62, 8.50, 7.93, −2.40. HRMS: [$C_{19}H_{23}NSi$] calculated 293.1600, measured 293.1590.

Example 6.3.6: 1-methyl-2-(triethylsilyl)-1H-pyrrolo[2,3-b]pyridine

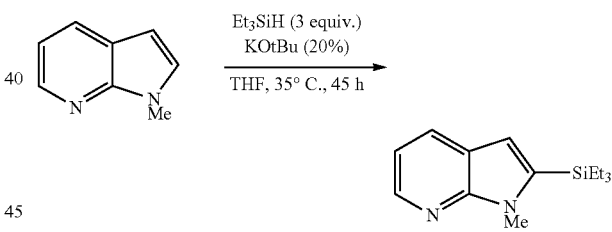

Figure 12:
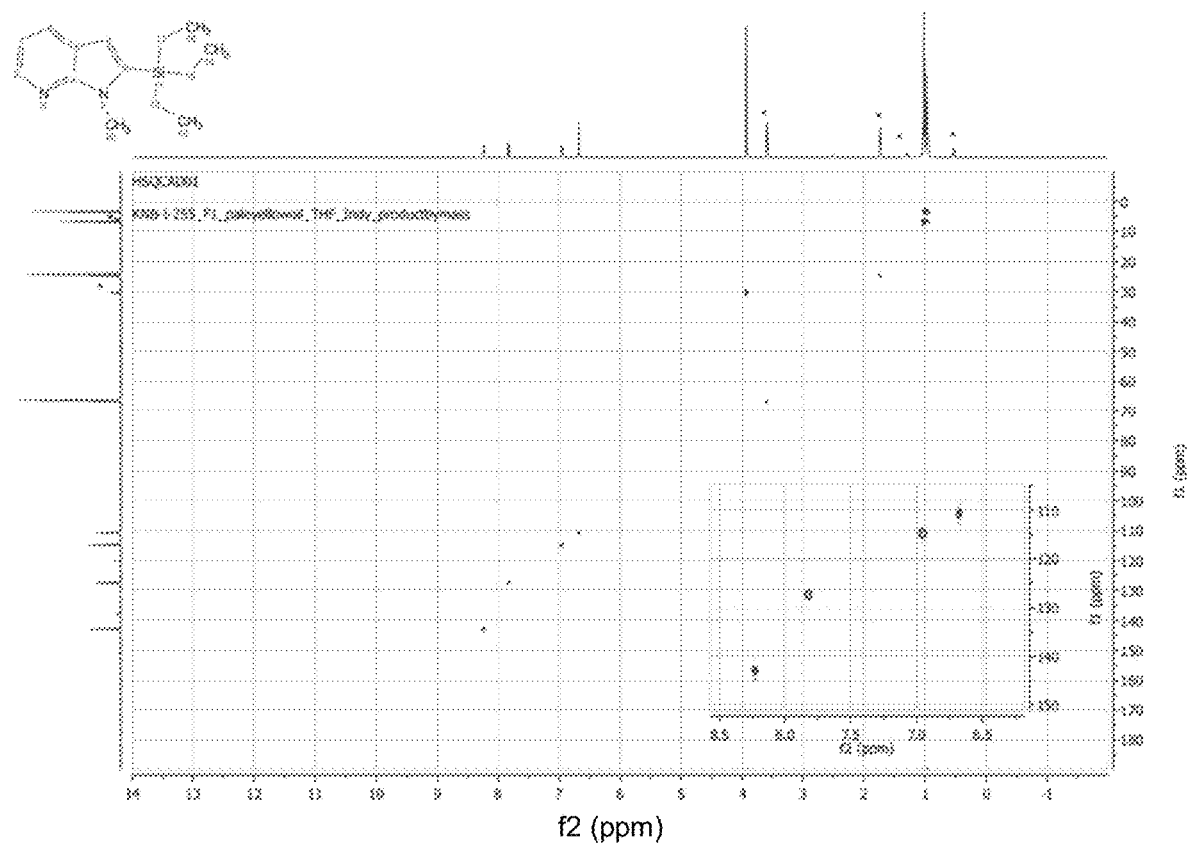

The reaction was conducted according to the General Procedure by heating N-methyl-1H-pyrrolo[2,3-b]pyridine (66 mg, 0.5 mmol, 1 equiv.), KOt-Bu (11 mg, 0.1 mmol, 0.2 equiv.) and Et$_3$SiH (239 microliters, 1.5 mmol, 3 equiv.) in 1 mL of tetrahydrofuran for 45 hours at 35° C. After aqueous work up, the crude reaction mixture was purified by chromatography on silica using step gradient elution (starting with 100% hexanes and increasing the polarity of the eluent stepwise to 30% EtOAc in Hexanes) to obtain 89 mg (73%) of the title compound as a pale yellow oil. $^1$H NMR (500 MHz, THF-d8) δ 8.45-7.95 (m, 1H), 7.97-7.66 (m, 1H), 6.95 (dd, J=7.7, 4.6 Hz, 1H), 6.68 (s, 1H), 3.94 (s, 2H), 1.05-1.00 (m, 9H), 0.97 (td, J=7.1, 1.7 Hz, 6H). $^{13}$C NMR (126 MHz, THF-d8) δ 150.95, 142.87, 137.82, 127.38, 120.13, 114.79, 110.76, 30.27, 6.74, 3.31. HRMS: [$C_{14}H_{23}N_2Si$] calculated 247.1642, measured 247.1631. The structural characterization of this reaction product is based, in part, on an interpretation of the HSQC spectrum of this reaction product as provided in FIG. 12.

Example 6.3.7: Silylation of N-methyl-2-methylindole

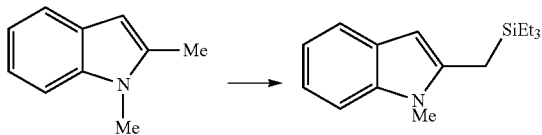

Figure 13:
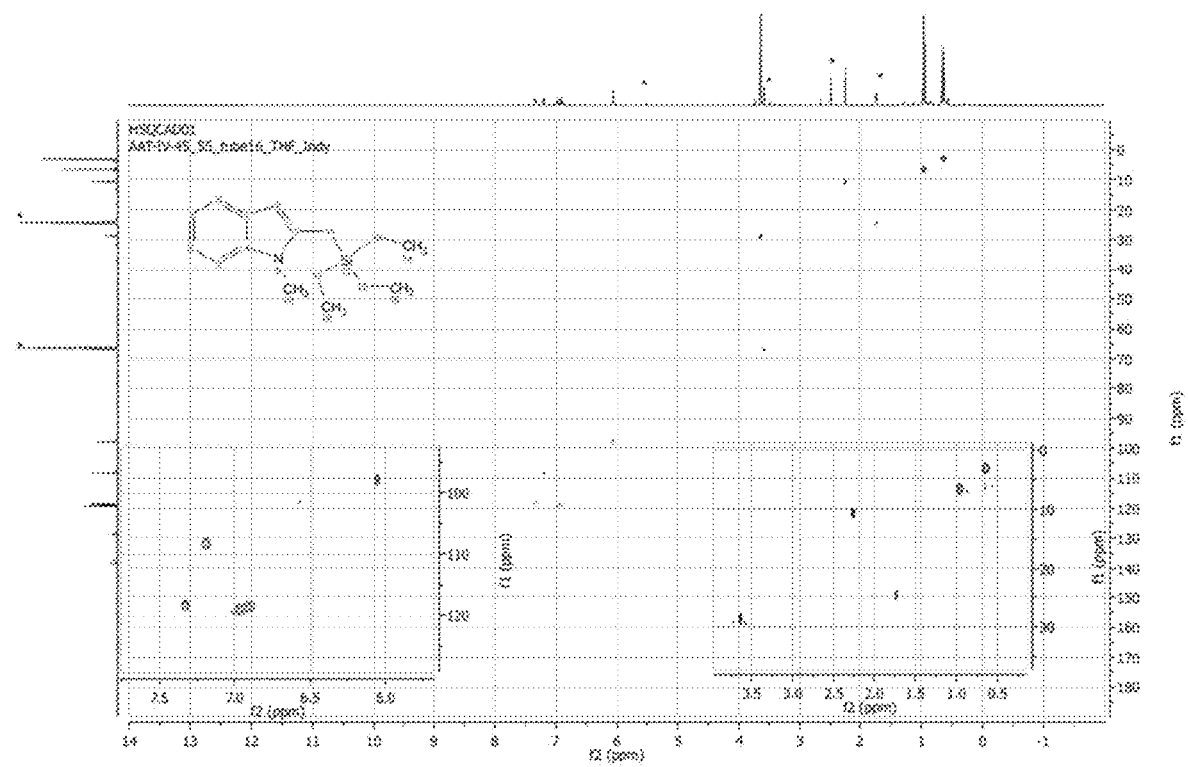

The reaction was conducted according to the General Procedure by heating 1,2-dimethylindole (73 mg, 0.5 mmol, 1 equiv.), KOt-Bu (17 mg, 0.15 mmol, 0.3 equiv) and Et$_3$SiH (319 microliters, 2.0 mmol, 4 equiv.) in 1 mL of tetrahydrofuran for 65 hours at 65° C. After aqueous work up, the crude reaction mixture was purified by chromatography on silica using an 80:1:4 mixture of hexanes:diethyl ether:triethylamine respectively to obtain 74 mg (57%) of the title compound as a colourless oil. $^1$H NMR (500 MHz, THF-d$_8$) δ 7.35-7.29 (m, 1H), 7.19 (dd, J=8.1, 0.9 Hz, 1H), 6.97 (ddd, J=8.2, 7.1, 1.2 Hz, 1H), 6.90 (ddd, J=8.0, 7.1, 1.1 Hz, 1H), 6.06 (d, J=0.8 Hz, 1H), 3.64 (s, 3H), 2.25 (d, J=0.7 Hz, 2H), 0.96 (t, J=7.9 Hz, 9H), 0.71-0.58 (m, 6H). $^{13}$C NMR (126 MHz, THF-d$_8$) δ 139.50, 138.30, 129.69, 120.24, 119.70, 119.47, 109.27, 98.96, 29.75, 11.73, 7.62, 4.16. HRMS: [C$_{16}$H$_{25}$NSi] calculated 259.1756, measured 259.1754. The structural characterization of this reaction product is based, in part, on an interpretation of the HSQC spectrum of this reaction product as provided in FIG. 13.

Example 6.3.8: Silylation of N-methyl pyrrole

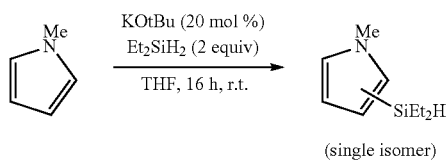

(single isomer)

Example 6.3.9: 9,9-diethyl-9H-benzo[d]pyrrolo[1,2-a][1,3]azasilole

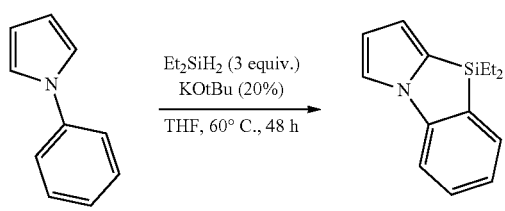

Figure 14:
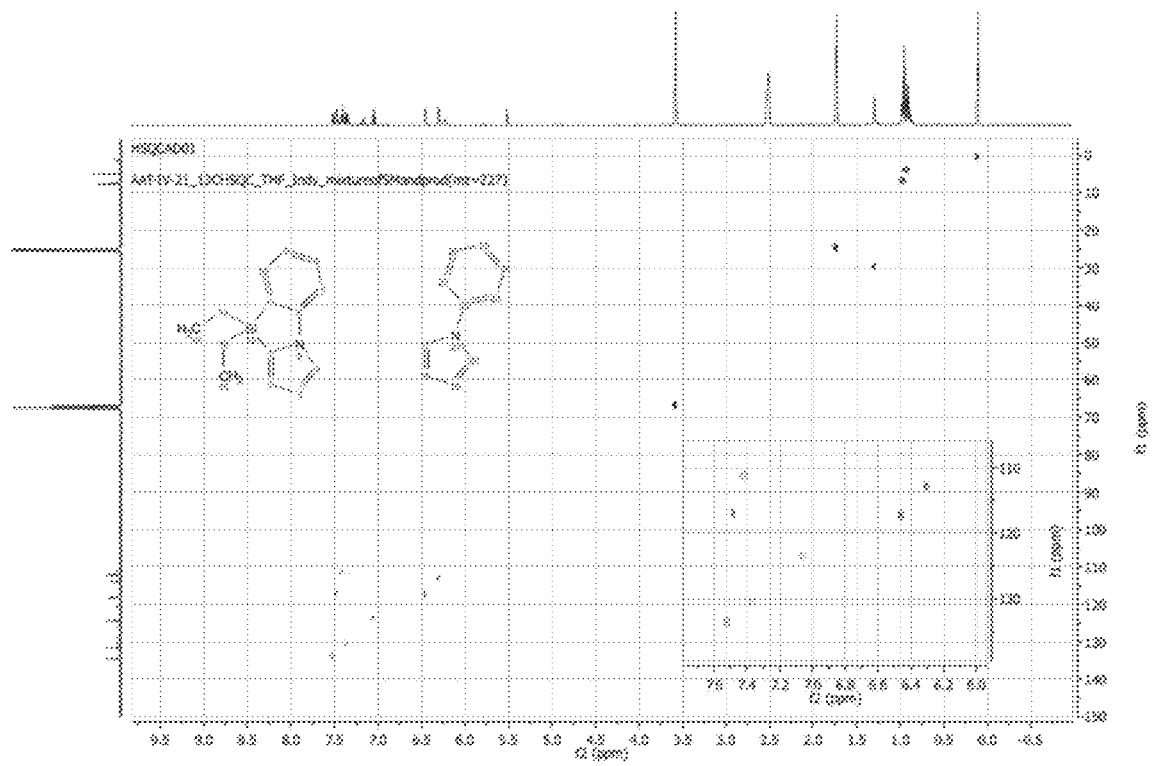

The reaction was conducted according to the General Procedure by heating 1-phenylpyrrole (161 mg, 0.5 mmol, 1 equiv.), KOt-Bu (11 mg, 0.1 mmol, 0.2 equiv) and Et$_2$SiH$_2$ (194 microliters, 1.5 mmol, 3 equiv.) in 1 mL of tetrahydrofuran for 65 hours at 60° C. After aqueous work up, the crude reaction mixture was purified by chromatography on silica using hexanes (isochratic) to obtain 97 mg (85%) of a mixture containing approximately a 7:1 mixture of the title compound and the starting material as a colourless oily solid. $^1$H NMR (500 MHz, THF-d8) δ 7.51 (ddd, J=7.1, 1.5, 0.6 Hz, 1H), 7.47 (dd, J=2.6, 1.1 Hz, 1H), 7.43-7.39 (m, 1H), 7.38-7.33 (m, 1H), 7.04 (td, J=7.2, 1.0 Hz, 1H), 6.45 (dd, J=3.2, 1.1 Hz, 1H), 6.29 (t, J=2.9 Hz, 1H), 1.00-0.94 (m, 6H), 0.94-0.86 (m, 4H). $^{13}$C NMR (126 MHz, THF-d$_8$) δ 134.81, 131.71, 130.28, 124.66, 120.80, 118.47, 118.18, 114.05, 112.42, 111.28, 7.91, 5.18. HRMS: [C$_{14}$H$_{18}$NSi] calculated 228.1213, measured 228.1208. The structural characterization of this reaction product is based, in part, on an interpretation of the HSQC spectrum of this reaction product as provided in FIG. 14.

Example 6.3.10: Benzofuran-2-yltriethylsilane

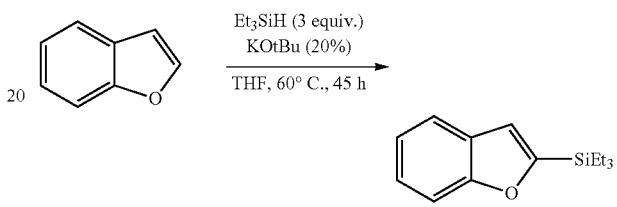

Figure 15:
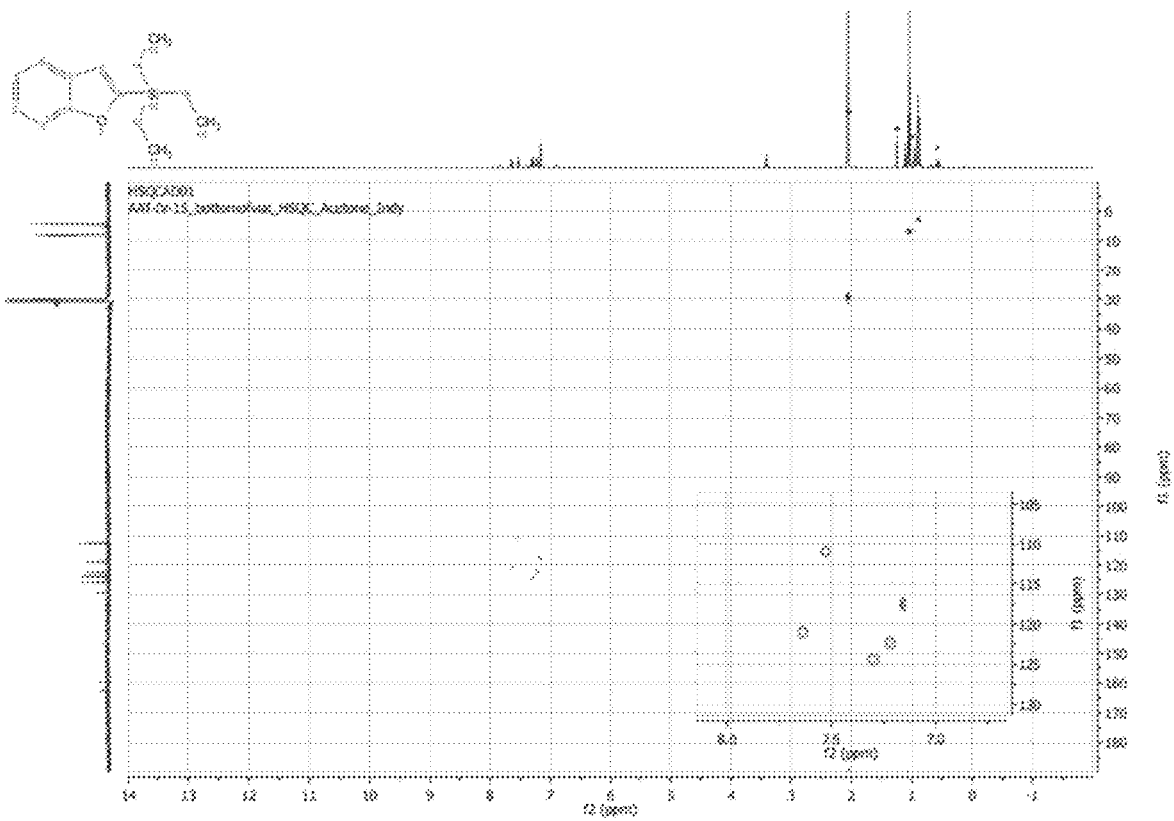

The reaction was conducted according to the General Procedure by heating benzofuran (59 mg, 0.5 mmol, 1 equiv.), KOt-Bu (19.6 mg, 0.18 mmol, 0.35 equiv.) and Et$_3$SiH (239 microliters, 1.5 mmol, 3 equiv.) in 1 mL of tetrahydrofuran for 45 hours at 60° C. After aqueous work up, the crude reaction mixture was purified by chromatography on silica eluting with hexanes (isochratic) to obtain 44 mg (38%) of the title compound as a colourless oil. $^1$H NMR (500 MHz, Acetone-d6) δ 7.64 (ddd, J=7.7, 1.3, 0.7 Hz, 1H), 7.53 (dd, J=8.2, 0.9 Hz, 1H), 7.30 (ddd, J=8.3, 7.2, 1.3 Hz, 1H), 7.22 (ddd, J=7.7, 7.2, 1.0 Hz, 1H), 7.16 (d, J=1.0 Hz, 1H), 1.09-0.98 (m, 9H), 0.92-0.84 (m, 6H). The structural characterization of this reaction product is based, in part, on an interpretation of the HSQC spectrum of this reaction product as provided in FIG. 15.

Example 6.3.11: Benzo[b]thiophen-2-yltriethylsilane

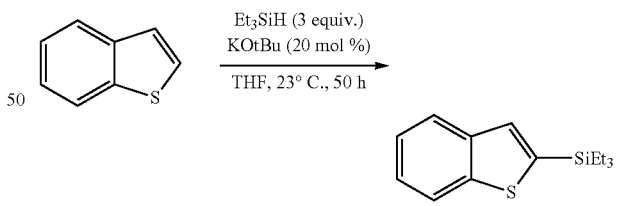

Figure 16A:
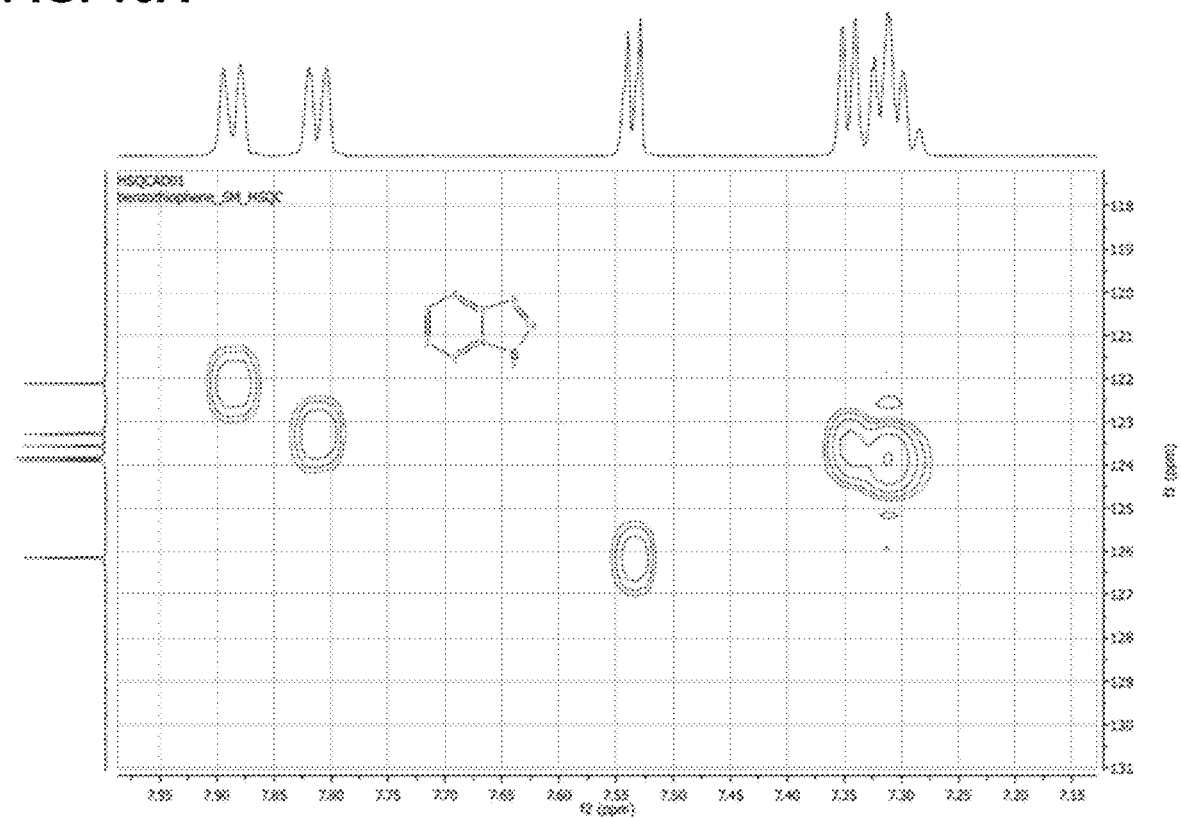
FIG. 16A-B are the HSQC spectra of (A) benzothiophene and (B) the product of its reaction with triethylsilane, as described in Example 6.3.11, characterized as benzo[b]thiophen-3-yltriethylsilane.
Figure 16B:
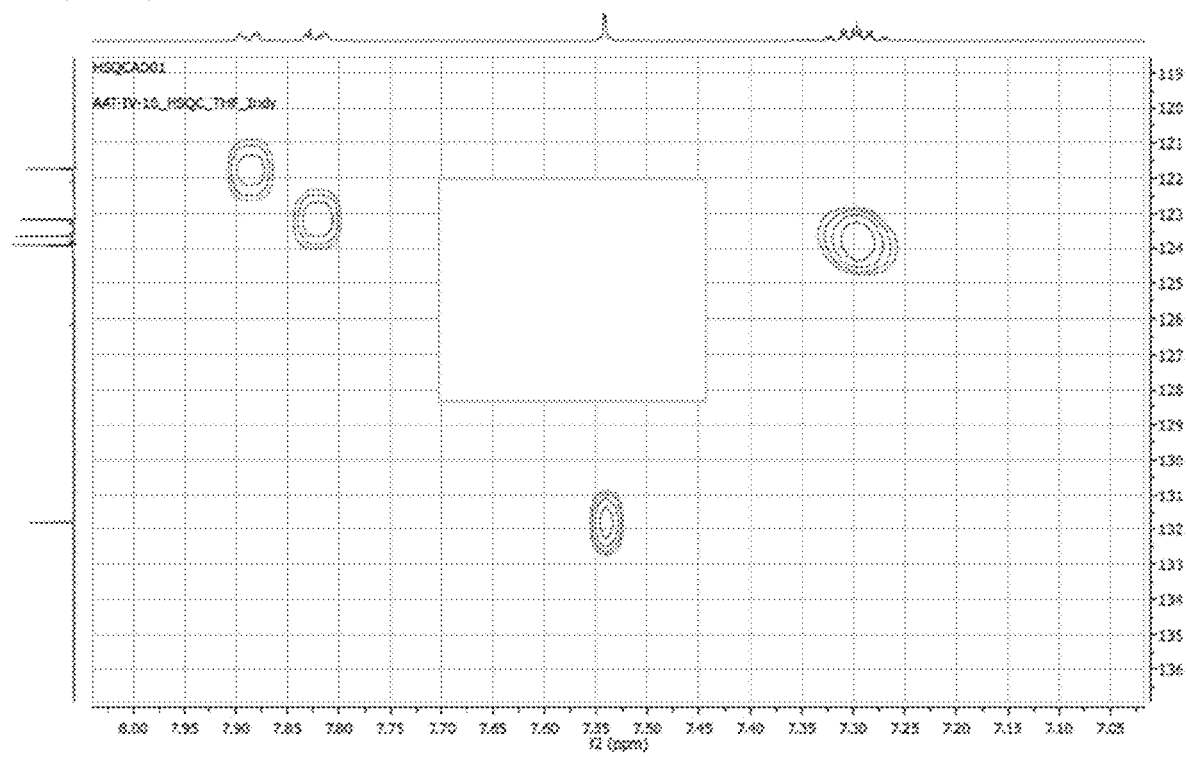

The reaction was conducted according to the General Procedure by heating thianaphthene (66 mg, 0.5 mmol, 1 equiv.), KOt-Bu (8.4 mg, 0.08 mmol, 0.15 equiv.) and Et$_3$SiH (239 microliters, 1.5 mmol, 3 equiv.) in 1 mL of tetrahydrofuran for 50 hours at 23° C. After aqueous work up, the crude reaction mixture was purified by chromatography on silica eluting with 80:2 hexanes:triethylamine to obtain 103 mg (83%) of the title compound as a colourless oil. $^1$H NMR (500 MHz, THF-d8) δ 7.90-7.85 (m, 1H), 7.84-7.76 (m, 1H), 7.53 (d, J=0.8 Hz, 1H), 7.34-7.20 (m, 2H), 1.08-0.99 (m, 9H), 0.95-0.80 (m, 6H). $^{13}$C NMR (126 MHz, THF-d8) δ 144.78, 142.34, 139.12, 132.97, 125.10, 124.84, 124.34, 122.91, 7.84, 5.10. HRMS: [C$_{14}$H$_{20}$SSi] calculated 248.1051, measured 248.1055. The structural characterization of this reaction product is based, in part, on an interpretation of the HSQC spectrum of this reaction product as provided in FIG. 16(B).

Example 6.3.12: Benzo[b]thiophen-2-yldimethyl (phenyl)silane

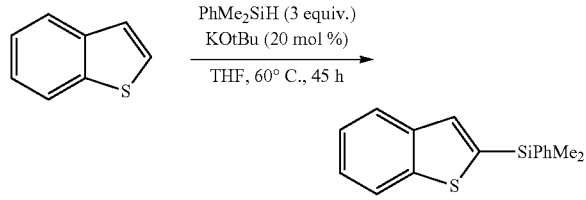

The reaction was conducted according to the General Procedure by heating thianaphthene (66 mg, 0.5 mmol, 1 equiv.), KOt-Bu (8.4 mg, 0.08 mmol, 0.15 equiv.) and PhMe$_2$SiH (239 microliters, 1.5 mmol, 3 equiv.) in 1 mL of tetrahydrofuran for 48 hours at 65° C. After aqueous work up, the crude reaction mixture was purified by chromatography on silica eluting with hexanes (isochratic) to obtain 102 mg (76%) of the title compound as a pale yellow oily solid. $^1$H NMR (500 MHz, CDCl$_3$) δ 7.94-7.87 (m, 1H), 7.85-7.78 (m, 1H), 7.71-7.58 (m, 2H), 7.51 (d, J=0.8 Hz, 1H), 7.46-7.39 (m, 3H), 7.38-7.30 (m, 2H), 0.69 (s, 6H). $^{13}$C NMR (126 MHz, CDCl$_3$) δ 144.01, 141.12, 140.18, 137.29, 134.13, 132.41, 129.70, 128.09, 124.45, 124.18, 123.69, 122.33, −1.42. HRMS: [C$_{16}$H$_{16}$SSi] calculated 268.0743, measured 268.0742.

Example 6.3.13: Silylation of Dibenzothiophene

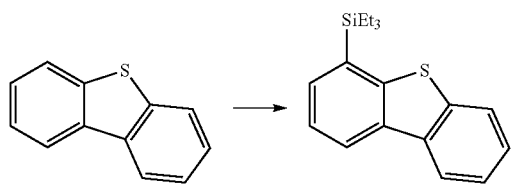

Figure 17:
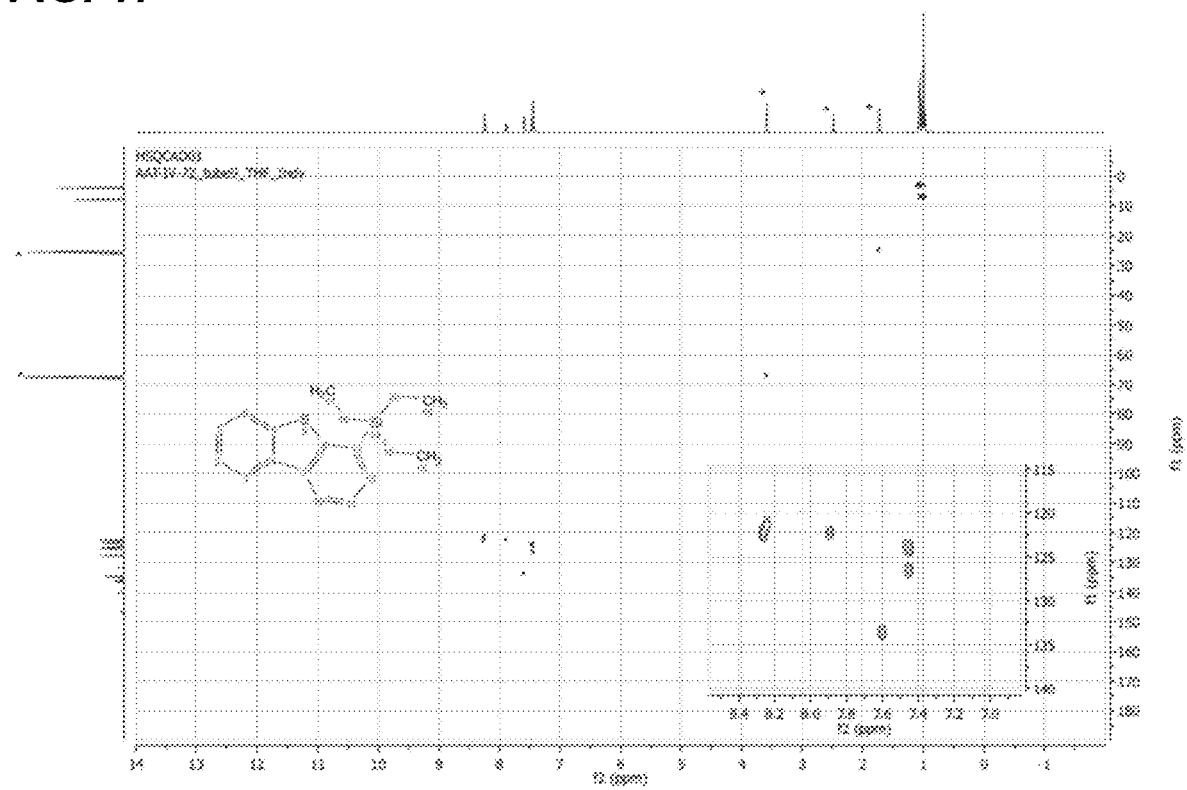

The reaction was conducted according to the General Procedure by heating dibenzothiophene (92 mg, 0.5 mmol, 1 equiv.), KOt-Bu (5.6 mg, 0.05 mmol, 0.1 equiv) and Et$_3$SiH (160 microliters, 1.0 mmol, 2 equiv.) in 1 mL of 1,4-dioxane for 14 hours at 75° C. After aqueous work up, the crude reaction mixture was purified by chromatography on silica using an 80:2 mixture of hexanes:triethylamine to obtain 51 mg (34%) of the title compound as a colourless oil. $^1$H NMR (500 MHz, THF-d$_8$) δ 8.26-8.22 (m, 2H), 7.90-7.86 (m, 1H), 7.59 (dd, J=7.1, 1.3 Hz, 1H), 7.47-7.41 (m, 3H), 1.11-1.02 (m, 6H), 1.02-0.95 (m, 9H). $^{13}$C NMR (126 MHz, THF-d$_8$) δ 146.49, 140.15, 136.57, 136.06, 134.74, 131.79, 127.63, 125.30, 124.86, 123.53, 123.39, 122.48, 7.94, 3.98. HRMS: [C$_{18}$H$_{22}$SSi] calculated 255.1205, measured 255.1206, The structural characterization of this reaction product is based, in part, on an interpretation of the HSQC spectrum of this reaction product as provided in FIG. 17.

Example 6.3.14: Silylation of 2,5-dimethyl thiophene

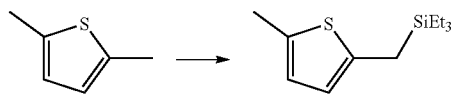

The reaction was conducted according to the General Procedure by heating 2,5,dimethyl thiophene (56 mg, 0.5 mmol, 1 equiv.), KOt-Bu (11.2 mg, 0.1 mmol, 0.2 equiv.) and Et$_3$SiH (3 equiv.) in tetrahydrofuran for 45 hours at 65° C. GC-MS of the crude product mixture yielded a mass peak associated with the monosilated derivative. $^1$H NMR data were consistent with formation of 2-methyl-5-(triethylsilyl-methyl)thiophene. $^1$H NMR (500 MHz, THF-d8) δ 6.52-6.42 (m, 1H), 6.41-6.29 (m, 1H), 2.35 (s, 3H), 2.23 (s, 2H), 1.00-0.92 (m, 9H), 0.63-0.53 (m, 6H). $^{13}$C NMR (126 MHz, THF-d8) δ 140.78, 136.28, 125.96, 124.03, 15.73, 15.45, 7.97, 4.08. HRMS: [C$_{12}$H$_{22}$SSi] calculated 226.1212, measured 226.1220.

Example 6.3.15: Silylation of Pyridine

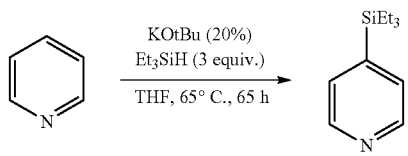

The reaction was conducted according to the General Procedure by heating pyridine (40 mg, 0.5 mmol, 1 equiv.), KOt-Bu (17 mg, 0.15 mmol, 0.3 equiv) and Et$_3$SiH (240 microliters, 1.5 mmol, 3 equiv.) in 1 mL of tetrahydrofuran for 65 hours at 65° C. After aqueous work up, the crude reaction mixture was purified by chromatography on silica using an 80:1:4 mixture of hexanes:diethyl ether:triethylamine respectively to obtain 14 mg (15%) of the title compound as a colourless oily solid. $^1$H NMR (500 MHz, THF-d$_8$) δ 8.99-8.16 (m, 2H), 7.62-7.07 (m, 2H), 1.01-0.93 (m, 6H), 0.91-0.79 (m, 4H). $^{13}$C NMR (126 MHz, THF-d$_8$) δ 149.88, 129.76, 129.29, 7.70, 3.66. HRMS: [C$_{11}$H$_{20}$NSi] calculated 194.1365, measured 194.1367.

Example 6.3.16: Attempted Silylation of 4-Methoxypyridine

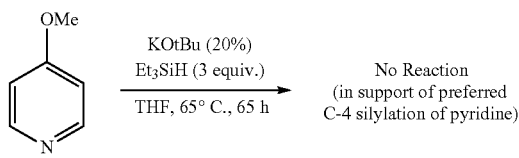

The reaction was conducted according to the General Procedure by heating 4-methoxypyridine (55 mg, 0.5 mmol, 1 equiv.), KOt-Bu (17 mg, 0.15 mmol, 0.3 equiv) and Et$_3$SiH (240 microliters, 1.5 mmol, 3 equiv.) in 1 mL of tetrahydrofuran for 65 hours at 65° C. The reaction was diluted with diethyl ether (1 mL), quenched with water (0.5 mL) and the organic phase was analyzed by GC-MS, GC-FID and 1H NMR analysis and revealed no apparent conversion of the starting material to silylated products.

Example 6.3.17: Attempted Silylation of 2,6 dimethoxypyridine

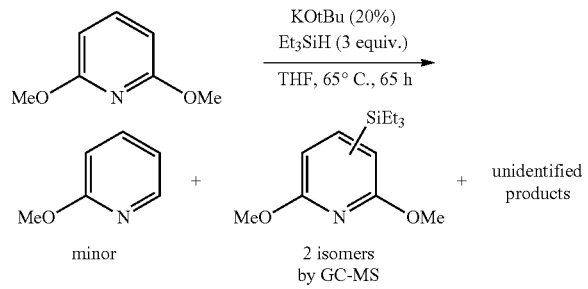

The reaction was conducted according to the General Procedure by heating 2,6-dimethoxypyridine (70 mg, 0.5 mmol, 1 equiv.), KOt-Bu (17 mg, 0.15 mmol, 0.3 equiv) and Et$_3$SiH (240 microliters, 1.5 mmol, 3 equiv.) in 1 mL of tetrahydrofuran for 65 hours at 65° C. The reaction was diluted with diethyl ether (1 mL), quenched with water (0.5 mL) and the organic phase was analyzed by GC-MS, GC-FID and 1H NMR analysis. GC-MS analysis revealed major mass peaks corresponding to the formation of 2 silylated product isomers as well as several unidentified products.

Example 7. Evaluation of Basic Activators in Silylation Reactions

The effects of various bases were evaluated under the following nominal conditions, with the results provided in Table 3:

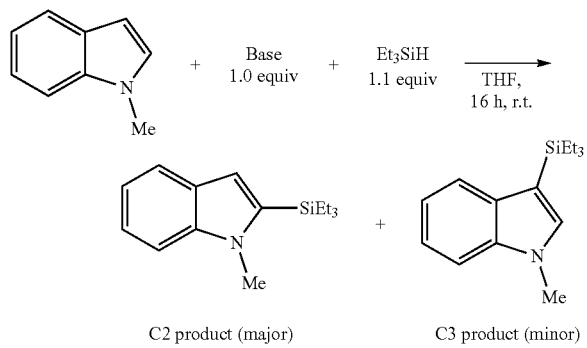

TABLE 3

Effect of bases on the silylation of N-methyl indole at ambient conditions

| Base | Yield C2 (%) | Selectivity |
|---|---|---|
| KOtBu | 66.7 | >95% |
| DABCO | 0 | — |
| KHMDS | 44 | >95% |
| LiOtBu | 0 | — |
| NaOtBu | 0 | — |
| NaOEt | 0 | — |
| KOEt | 14.2 | >95% |
| NaOAc | 0 | — |
| KOAc | 0 | — |
| KOMe | 4.6 | >95% |
| Cs$_2$CO$_3$ | 0 | — |
| KH | 0.1 | — |
| KOH | 0 | — |
| TBAF | 0 | — |
| KF | 0 | — |
| CsF | 0 | — |
| NaF | 0 | — |
| Me$_4$NF | 0 | — |
| KOtBu + 18-crown-6 (1:1) | 0 | — |

Yields and selectivities calculated using GC-FID analysis with mesitylene added as a standard for quantification. C2 selectivity defined as (yield C2 product)/(yield C2 + C3 product) × 100%

As can be seen from Table 3, typical silicon activators such as fluoride salts are not competent in catalyzing the reactions described herein. TBAF, KF, CsF, Me$_4$NF, NaF all give no conversion of the substrate.

Interestingly, while KOR salts appear to be excellent catalysts for the silylation transformation (with KOtBu being superior to all others, and with efficiency of other potassium alkoxides correlating loosely with basicity), NaOR and LiOR where R is Me, Et, iPr, tBu all give 0% conversion. This demonstrates the critical, albeit unknown, role of the potassium cation in this reaction.

Notably, the addition of 18-crown-6 as a potassium chelator in an equimolar amount to KOtBu gives 0% conversion of the substrate under standard conditions, thus lending further support for a critical role of the potassium cation. Interestingly, other potential chelants did not inhibit, and in many cases, improved both yield and selectivity of the systems. This effect is not well understood. Without being bound by the correctness of this or any other theory, it is possible that these ligands chelated the potassium cation is proposed. Bipyridine-based ligand scaffolds as well as TMEDA (not shown) were demonstrated to be most effective in promoting high selectivity and efficiency in the silylation reaction. This is supported by the reaction with 1,7-phen, which is unable to chelate potassium, giving a lower product yield.

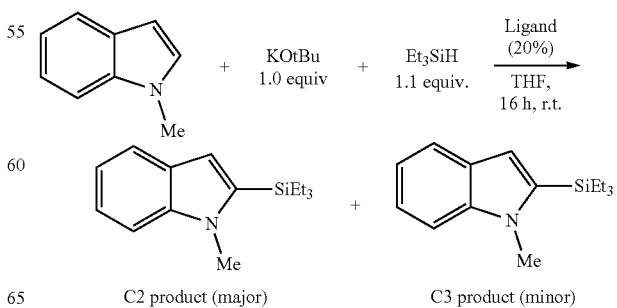

TABLE 4

Effect of bases on the silylation of N-methyl indole at ambient conditions

| Ligand | Yield C2 | Selectivity |
|---|---|---|
| 1,10-phenanthroline | 20.7 | >95% |
| 1,7-phenanthroline | 11.4 | >95% |
| bathophenanthroline | 33.7 | >95% |
| bipyridine | 64.8 | >95% |
| 4,4'-di-t-Bu bipyridine | 60 | >95% |

Yields and selectivities calculated using GC-FID analysis with mesitylene added as a standard for quantification. C2 selectivity defined as yield (C2 product/yield C2 + C3 products) × 100%.

The activity of the inventive systems and methods were remarkably tolerant of different base loadings. In the N-methylindole model system, for example, decreasing base loading only mildly decreased efficiency. Remarkably, KOtBu even down to 1 mol % was effective and gave the major C2 product in 65% yield and a corresponding 89% C2 selectivity. This loading is even lower or equal to that required for the state-of-the-art transition-metal-based aromatic C—H silylation systems.

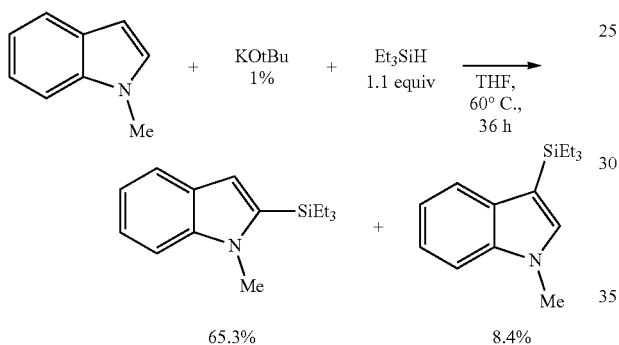

As those skilled in the art will appreciate, numerous modifications and variations of the present disclosure are possible in light of these teachings, and all such are contemplated hereby. For example, in addition to the embodiments described herein, the present disclosure contemplates and claims those inventions resulting from the combination of features of the disclosure cited herein and those of the cited prior art references which complement the features of the present disclosure. Similarly, it will be appreciated that any described material, feature, or article may be used in combination with any other material, feature, or article, and such combinations are considered within the scope of this disclosure.

The disclosures of each patent, patent application, and publication cited or described in this document are hereby incorporated herein by reference, each in its entirety, for all purposes.

The invention claimed is:

1. A method of preparing silylated compound comprising a moiety of Formula (I) or Formula (II):

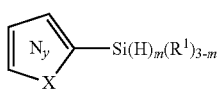 (I)

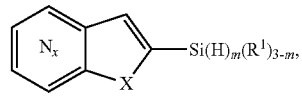 (II)

the method comprising:
contacting a substrate containing a

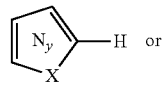 (III)

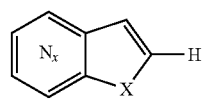 (IV)

moiety with (a) a hydrosilane of formula $(R^1)_{3-m}Si(H)_{m+1}$ and (b) at least one strong base comprising an alkali metal alkoxide, an alkali metal hydride, an alkaline earth metal hydride, or potassium bis(trimethylsilyl) amide, under conditions to form the silylated compound, the method resulting in the formation of the silylated compound comprising the moiety of Formula (I) or Formula (II);
wherein
m is 0, 1, or 2;
$R^1$ is independently optionally substituted $C_{1-12}$ alkyl, $C_{1-12}$ heteroalkyl, or an optionally substituted 5- or 6-membered aryl or heteroaryl, and, if substituted, the substituents are independently alkyl, alkenyl, aryl, heteroaryl, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, amino, optionally protected carboxyl, carboxylato, cyano, halo, phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amido, imino, nitro, nitroso, mercapto, optionally protected formyl, $C_1$-$C_{20}$ thioester, cyanato, thiocyanato, isocyanate, thioisocyanate, carbamoyl, epoxy, styrenyl, silyl, silyloxy, silanyl, siloxazanyl, boronato, or boryl;
X is $NR^2$, O, or S;
$R^2$ is an amine protecting group, an optionally substituted alkyl, optionally substituted aryl, optionally substituted heteroaryl, optionally substituted alkaryl or optionally substituted alk-heteroaryl;

is a heteroaromatic moiety containing y additional nitrogens in the ring structure, where y=0 or 1 when X is O or S, or y=0, 1, or 2 when X is $NR^2$; and

is an aromatic moiety containing x nitrogen atoms in the ring structure, wherein x is 0, 1, or 2.

2. The method of claim 1, wherein the moiety of formula (I) or (III) is a furan, pyrrole, thiophene, pyrazole, imidazole, triazole, isoxazole, oxazole, thiazole, isothiazole, or oxadiazole.

3. The method of claim 1, resulting in the formation of the silylated compound comprising the moiety of Formula (I) having a structure of:

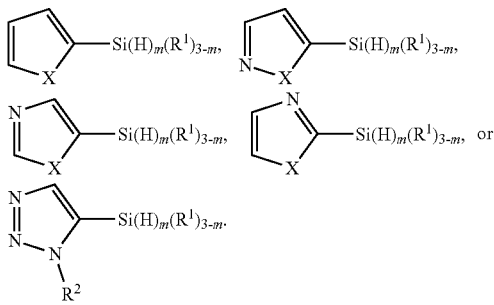

4. The method of claim 1, resulting in the formation of the silylated compound comprising the moiety of Formula (I) having a structure of:

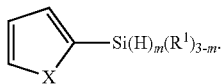

5. The method of claim 1, resulting in the formation of the silylated compound comprising the moiety of Formula (I) having a structure of:

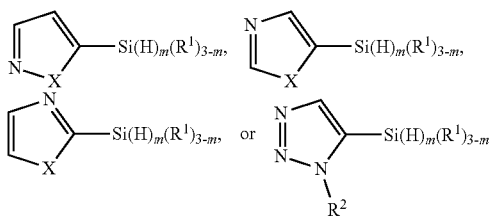

6. The method of claim 1, resulting in the formation of the silylated compound comprising the moiety of Formula (II) having a structure of:

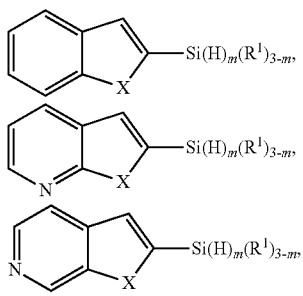

-continued

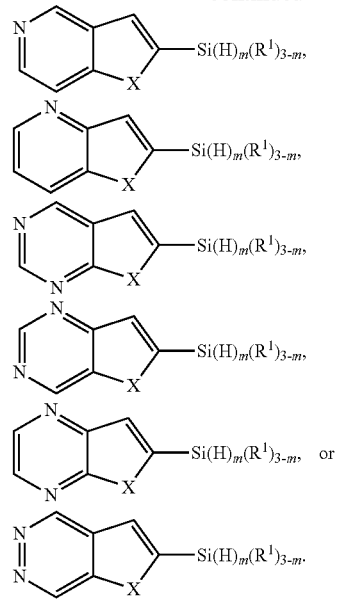

7. The method of claim 1, resulting in the formation of the silylated compound comprising the moiety of Formula (II) having a structure of:

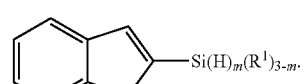

8. The method of claim 1, resulting in the formation of the silylated compound comprising the moiety of Formula (II) having a structure of:

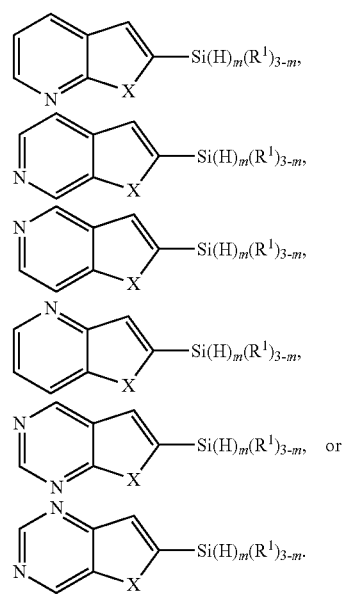

9. The method of claim 1, wherein the at least one strong base comprises the alkali metal alkoxide.

10. The method of claim 9, wherein the alkali metal alkoxide comprises a potassium alkoxide or a cesium alkoxide.

11. The method of claim 10, wherein the potassium alkoxide or cesium alkoxide comprises a $C_{1-12}$ linear or branched alkyl moiety or a $C_{5-10}$ aryl or heteroaryl moiety.

12. The method of claim 9, wherein the alkali metal alkoxide comprises potassium methoxide, potassium ethoxide, a potassium propoxide or a potassium butoxide.

13. The method of claim 9, wherein the alkali metal alkoxide comprises potassium tert-butoxide.

14. The method of claim 1, wherein the at least one strong base comprises an alkali metal hydride or an alkaline earth metal hydride.

15. The method of claim 1, wherein:
(a) the hydrosilane and the at least one strong base are present together at a molar ratio, with respect to one another, in a range of from 20:1 to 1:1; and/or
(b) the at least one strong base and organic substrate are present together at a molar ratio, with respect to one another, in a range of from 0.01:1 to 0.9:1.

16. The method of claim 1, wherein m=0.

17. The method of claim 1, wherein m=1, optionally wherein $R^1$ is independently tert-butyl, —$C(CH_3)_2(CN)$, pyridine, or an alkyl substituted heterocycloalkyl.

18. The method of claim 3, wherein m=1, optionally wherein $R^1$ is independently tert-butyl, —$C(CH_3)_2(CN)$, pyridine, or an alkyl substituted heterocycloalkyl.

19. The method of claim 6, wherein m=1, optionally wherein $R^1$ is independently tert-butyl, —$C(CH_3)_2(CN)$, pyridine, or an alkyl substituted heterocycloalkyl.

20. The method of claim 1, wherein m=2.

21. The method of claim 1, wherein $R^1$ is independently optionally substituted $C_{1-12}$ alkyl, optionally substituted heteroaryl or optionally substituted $C_{2-12}$ heterocycloalkyl.

22. The method of claim 3, wherein $R^1$ is independently optionally substituted $C_{1-12}$ alkyl, optionally substituted heteroaryl or optionally substituted $C_{2-12}$ heterocycloalkyl.

23. The method of claim 6, wherein $R^1$ is independently optionally substituted $C_{1-12}$ alkyl, optionally substituted heteroaryl or optionally substituted $C_{2-12}$ heterocycloalkyl.

24. The method of claim 1 where $R^1$ is independently optionally substituted cyclic alkyl or branched alkyl or cyclic or branched heteroalkyl.

25. The method of claim 3, wherein $R^1$ is independently optionally substituted cyclic alkyl or branched alkyl or cyclic or branched heteroalkyl.

26. The method of claim 6, wherein $R^1$ is independently optionally substituted cyclic alkyl or branched alkyl or cyclic or branched heteroalkyl.

27. The method of claim 1, wherein $R^1$ is independently tert-alkyl.

28. The method of claim 3, wherein $R^1$ is independently tert-alkyl.

29. The method of claim 6, wherein $R^1$ is independently tert-alkyl.

30. The method of claim 17, wherein R is independently tert-butyl, —$C(CH_3)_2(CN)$, pyridine, or an alkyl substituted heterocycloalkyl.

31. The method of claim 18, wherein R is independently tert-butyl, —$C(CH_3)_2(CN)$, pyridine, or an alkyl substituted heterocycloalkyl.

32. The method of claim 19, wherein R is independently tert-butyl, —$C(CH_3)_2(CN)$, pyridine, or an alkyl substituted heterocycloalkyl.

33. The method of claim 1, wherein X is $NR^2$.

34. The method of claim 1, wherein X is O.

35. The method of claim 1, wherein X is S.

36. The method of claim 1, resulting in the formation of the silylated compound comprising the moiety of Formula (I) having a structure of:

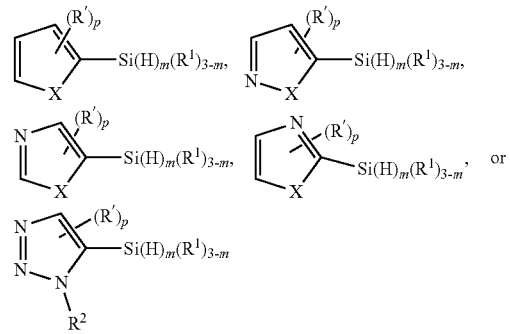

or of the silylated compound comprising the moiety of Formula (II) having a structure of:

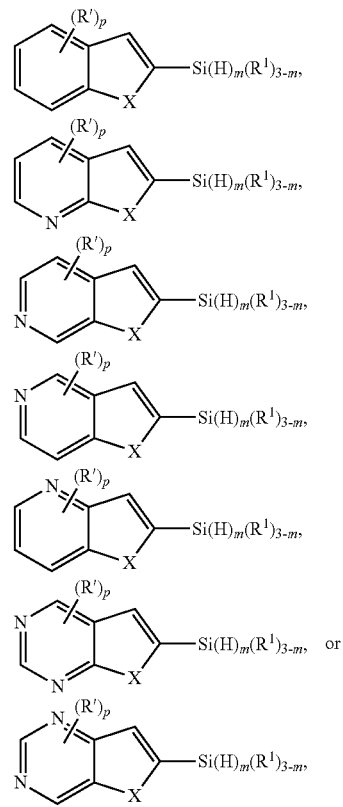

where R' is halo, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, $C_1$-$C_{24}$ alkylcarbonyl (—CO-alkyl), $C_6$-$C_{24}$ arylcarbonyl (—CO-aryl)), $C_2$-$C_{24}$ alkylcarbonyloxy (—O—CO-alkyl), $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—$NH_2$), mono-(C$_1$-C$_{24}$ alkyl)-substituted carbamoyl (—(CO)NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-(C$_1$-C$_{24}$ haloalkyl)-substituted carbamoyl (—(CO)—NH(C$_1$-C$_{24}$ alkyl)), di-(C$_1$-C$_{24}$ haloalkyl)-substituted carbamoyl (—(CO)—N(C$_1$-C$_{24}$ alkyl)$_2$), mono-(C$_5$-C$_{24}$ aryl)-substituted carbamoyl (—(CO)—NH-aryl), di-(C$_5$-C$_{24}$ aryl)substituted carbamoyl (—(CO)—N(C$_1$-C$_{24}$ aryl)$_2$), di-N—(C$_1$-C$_{24}$ alkyl), N—(C$_5$-C$_{24}$ aryl)-substituted carbamoyl, thiocarbamoyl (—(CS)—NH$_2$), mono-(C$_1$-C$_{24}$ alkyl)-substituted thiocarbamoyl (—(CO)—NH(C$_1$-C$_{24}$ alkyl)), di-(C$_1$-C$_{24}$ alkyl)-substituted thiocarbamoyl (—(CO)—N(C$_1$-C$_{24}$ alkyl)$_2$), mono-(C$_5$-C$_{24}$ aryl)substituted thiocarbamoyl (—(CO)—NH-aryl), di-(C$_5$-C$_{24}$ aryl)-substituted thiocarbamoyl (—(CO)—N(C$_5$-C$_{24}$ aryl)$_2$), di-N—(C$_1$-C$_{24}$ alkyl), N—(C$_5$-C$_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-(C$_1$-C$_{24}$ alkyl)-substituted amino, di-(C$_1$-C$_{24}$ alkyl)-substituted amino, mono-(C$_1$-C$_{24}$ aryl) substituted amino, di-(C$_5$-C$_{24}$ aryl)-substituted amino, C$_1$-C$_{24}$ alkylamido (—NH—(CO)-alkyl), C$_6$-C$_{24}$ arylamido (—NH—(CO)-aryl), imino (—CR═NH where R=hydrogen C$_1$-C$_{24}$ alkyl, C$_1$-C$_{24}$ aryl, C$_6$-C$_{24}$ alkaryl, C$_6$-C$_{24}$ aralkyl.), C$_2$-C$_{20}$ alkylimino (—CR═N(alkyl), where R=hydrogen, C$_1$-C$_{24}$ alkyl, C$_1$-C$_{24}$ aryl, C$_6$-C$_{24}$ alkaryl, C$_6$-C$_{24}$ aralkyl), arylimino (—CR═N(aryl), where R=hydrogen, C$_1$-C$_{20}$ alkyl, C$_1$-C$_{24}$ aryl, C$_6$-C$_{24}$ alkaryl, C$_6$-C$_{24}$ aralkyl), nitro (—NO$_2$), nitroso (—NO), sulfo (—SO$_2$OH), sulfonate(SO$_2$O—), C$_1$-C$_{24}$ alkylsulfanyl (—S-alkyl; also termed "alkylthio"), C$_5$-C$_{24}$ arylsulfanyl (—S-aryl; also termed "arylthio"), C$_1$-C$_{24}$ alkylsulfinyl (—(SO)-alkyl), C$_1$-C$_{24}$ arylsulfinyl (—(SO)-aryl), C$_1$-C$_{24}$ alkylsulfonyl (—SO$_2$-alkyl), C$_1$-C$_{24}$ monoalkylaminosulfonyl-SO$_2$—N(H) alkyl), C$_1$-C$_{24}$ dialkylaminosulfonyl-SO$_2$—N(alkyl)$_2$, C$_5$-C$_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—PO$_2$), phosphine (—PH$_2$), C$_1$-C$_{24}$ alkyl, C$_2$-C$_{24}$ alkenyl, C$_2$-C$_{24}$ alkynyl, C$_5$-C$_{24}$ aryl, C$_6$-C$_{24}$ alkaryl, and C$_6$-C$_{24}$ aralkyl; and p is 0, 1, 2, 3, or 4;
wherein the designation

refers to substitution of H on any ring position(s) of the respective moieties of Formula (I) or Formula (II).

37. The method of claim 36, resulting in the formation of the silylated compound comprising the moiety of Formula (I) having a structure of:

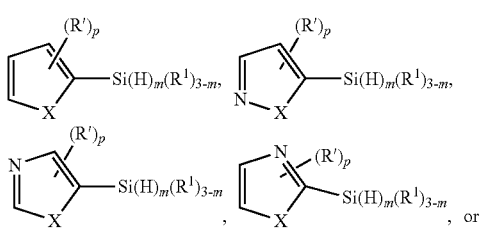

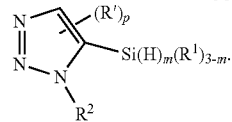

38. The method of claim 36, resulting in the formation of the silylated compound comprising the moiety of Formula (II) having a structure of:

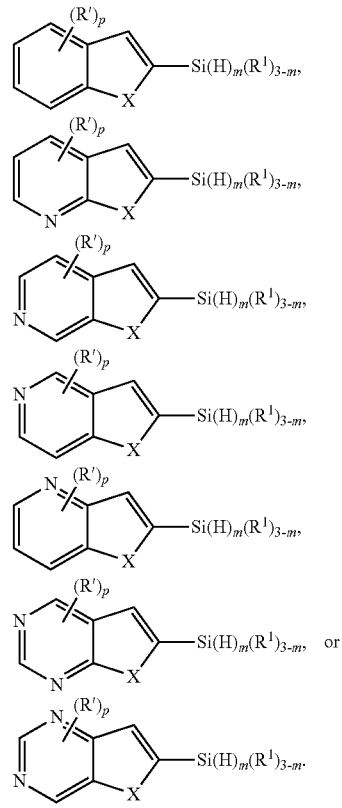

39. The method of claim 1, wherein the contacting is done in the absence of added transition-metal species.

40. A composition useful in the method of claim 1, the composition comprising:
(a) an organic substrate comprising an moiety of Formula (III) or (IV)

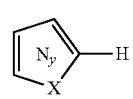

(III)

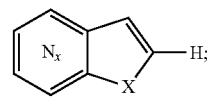

(IV)

(b) at least one hydroosilane of formula (R$^1$)$_{3-m}$Si(H)$_{m+1}$; and
(c) at least one strong base comprising an alkali metal alkoxide, an alkali metal hydride, an alkaline earth metal hydride, or potassium bis(trimethylsilyl)amide; and optionally (d) a silylated derivative of the organic substrate comprising a moiety of Formula (I) or Formula (II):

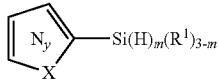
(I)

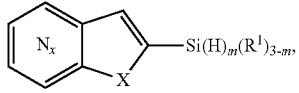
(II)

wherein m is 0, 1, or 2;

$R^1$ is independently optionally substituted $C_{1-12}$ alkyl, $C_{1-12}$ heteroalkyl, or an optionally substituted 5- or 6-membered aryl or heteroaryl, and, if substituted, the substituents are independently alkyl, alkenyl, aryl, heteroaryl, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, amino, optionally protected carboxyl, carboxylato, cyano, halo, phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amido, imino, nitro, nitroso, mercapto, optionally protected formyl, $C_1$-$C_{20}$ thioester, cyanato, thiocyanato, isocyanate, thioisocyanate, carbamoyl, epoxy, styrenyl, silyl, silyloxy, silanyl, siloxazanyl, boronato, or boryl;

X is $NR^2$, O, or S;

$R^2$ is an amine protecting group, an optionally substituted alkyl, optionally substituted aryl, optionally substituted heteroaryl, optionally substituted alkaryl or optionally substituted alk-heteroaryl;

is a heteroaromatic moiety containing y additional nitrogens in the ring structure, where y=0 or 1 when X is O or S, or y=0, 1, or 2 when X is $NR^2$; and

is an aromatic moiety containing x nitrogen atoms in the ring structure, wherein x is 0, 1, or 2.

* * * * *